United States Patent
Hubbell et al.

(10) Patent No.: US 11,207,444 B2
(45) Date of Patent: *Dec. 28, 2021

(54) CONFORMAL COATING OF CELLS FOR IMMUNOISOLATION

(71) Applicant: SERNOVA CORP., London (CA)

(72) Inventors: Jeffrey Hubbell, Preverenges (CH); Alice Tomei, Milan (IT)

(73) Assignee: SERNOVA CORP., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,220

(22) Filed: Apr. 13, 2020

(65) Prior Publication Data

US 2021/0030922 A1 Feb. 4, 2021

Related U.S. Application Data

(63) Continuation of application No. 14/114,690, filed as application No. PCT/US2012/035696 on Apr. 28, 2012, now Pat. No. 10,660,987.

(Continued)

(51) Int. Cl.
*A61L 27/34* (2006.01)
*A61K 47/10* (2017.01)
(Continued)

(52) U.S. Cl.
CPC .............. *A61L 27/34* (2013.01); *A61K 9/008* (2013.01); *A61K 9/0019* (2013.01);
(Continued)

(58) Field of Classification Search
None
See application file for complete search history.

(56) References Cited

U.S. PATENT DOCUMENTS

| 6,558,665 B1 | 5/2003 | Cohen |
| 6,716,246 B1 | 4/2004 | Gonzalez |

(Continued)

FOREIGN PATENT DOCUMENTS

| WO | WO1997016176 | 5/1997 |
| WO | WO2005103106 | 11/2005 |

OTHER PUBLICATIONS

Anna et al., "Formation of Dispersions Using 'Flow Focusing' in Microchannels," Applied Physics Letters, 82(3):364-366 (2003).
(Continued)

*Primary Examiner* — Nicole P Babson
(74) *Attorney, Agent, or Firm* — Haley Guiliano LLP; Karen Mangasarian

(57) ABSTRACT

Hydrodynamic methods for conformally coating non-uniform size cells and cell clusters for implantation, thus preventing immune rejection or inflammation or autoimmune destruction while preserving cell functionality. A method for conformally coating cells and c clusters with hydrogels that are biocompatible, mechanically and chemically stable and porous, with an appropriate pore cut-off size. The methods of the invention are advantageously reproducible and result in a relatively high yield of coated versus non-coated cell clusters, without compromising cell functionality. Conformal coating devices configured to perform the methods of the invention, methods of optimally utilizing said devices and purifying the coated islets, and coated biomaterials made by said methods.

11 Claims, 44 Drawing Sheets

Related U.S. Application Data

(60) Provisional application No. 61/480,513, filed on Apr. 29, 2011.

(51) Int. Cl.

| | | |
|---|---|---|
| *C12N 5/00* | (2006.01) | |
| *A61K 9/00* | (2006.01) | |
| *A61K 9/06* | (2006.01) | |
| *A61K 9/48* | (2006.01) | |
| *A61K 9/20* | (2006.01) | |
| *A61K 35/39* | (2015.01) | |
| *A61L 27/36* | (2006.01) | |

(52) U.S. Cl.
CPC ............ *A61K 9/0024* (2013.01); *A61K 9/06* (2013.01); *A61K 9/2018* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 35/39* (2013.01); *A61K 47/10* (2013.01); *A61L 27/3604* (2013.01); *A61L 27/3683* (2013.01); *C12N 5/0012* (2013.01); *A61L 2420/02* (2013.01)

(56) References Cited

U.S. PATENT DOCUMENTS

| | | | |
|---|---|---|---|
| 6,911,227 | B2 | 6/2005 | Hubbell |
| 2004/0195710 | A1 | 10/2004 | Hubbell |
| 2006/0024276 | A1 | 2/2006 | Ricordi |
| 2009/0014360 | A1 | 1/2009 | Toner |
| 2009/0175927 | A1 | 7/2009 | Gammelstaeter |
| 2011/0165219 | A1 | 7/2011 | Barkai |
| 2011/0285042 | A1 | 11/2011 | Viovy |
| 2017/0216489 | A1 | 8/2017 | Hubbell |

OTHER PUBLICATIONS

Barrero et al., "Micro- and Nanoparticles via Capillary Flows," Annual Review of Fluid Mechanics, 39(1):89-106 (2007).
Beck et al., "Islet encapsulation: Strategies to Enhance Islet Cell Functions," Tissue Engineering, 13(3):1-11 (2007).
Cellesi "New fully synthetic materials for cell encapsulation," Doctoral Thesis, ETH Zurich [online], 2003 [Retrieved on Jul. 2, 2012], pp. 1-130.
Chabert et al., "Microfluidic high-throughput encapsulation and hydrodynamic self-sorting of single cells," PNAS, 105:3191-3196 (2008).
Chang et al., "The in vivo delivery of heterologous proteins by microencapsulated recombinant cells," Trends in Biotechnology, 17:78-83 (1999).
Cohen et al., "Using selective withdrawal to coat microparticles," Science, 292:265-267 (2001).
De Groot et al., "Causes of limited survival of microencapsulated pancreatic islet grafts," Journal of Surgical Research, 121:141-150 (2004).
De Vos et al., "Treatment of diabetes with encapsulated islets," Advances in Experimental Medicine and Biology, 670:3853 (2010).
Eggleton et al., "Tip streaming from a drop in the presence of surfactants," Physical Review Letters, 87:048302 (2001).
Kim et al., "Synthesis and Characterization of Injectable Poly(N-isopropylacrylamide-co-acrylic acid) Hydrogels with Proteolytically Degradable Cross-Links," Biomacromolecules, 4(5):1214-1223 (2003).
Loscertales et al., "Micro/nano encapsulation via electrified coaxial liquid jets," Science, 295:1695-1698 (2002).
Minguez-Castellanos et al., "Carotid body autotransplantation in Parkinson disease: a clinical and positron emission tomography study," Journal of Neurology, Neurosurgery, and Psychiatry , 78(8):825831 (2007).
Rabanel et al., "Progress technology in microencapsulation methods for cell therapy," Biotechnology Progress, 25:946-963 (2009).
Rinsch et al., "Delivery of erythropoietin by encapsulated myoblasts in a genetic model of severe anemia," Kidney Intern, 62:1395-1401 (2002).
Robertson, "Update on transplanting beta cells for reversing type 1 diabetes," Endocrinology and Metabolism Clinics of North America, 39:655-667 (2010).
Temura et al., "Bioartificial pancreas-Microencapsulation and conformal coating of islet of Langerhans," Advanced Drug Delivery Reviews, 62:827-840 (2010).
Utada et al., "Absolute instability of a liquid jet in a coflowing stream, "Physical Review Letters, 100:014502 (2008).
Wyman et al., "Immunoisolating pancreatic islets by encapsulation with selective withdrawal," Small, 3:683-690 (2007).

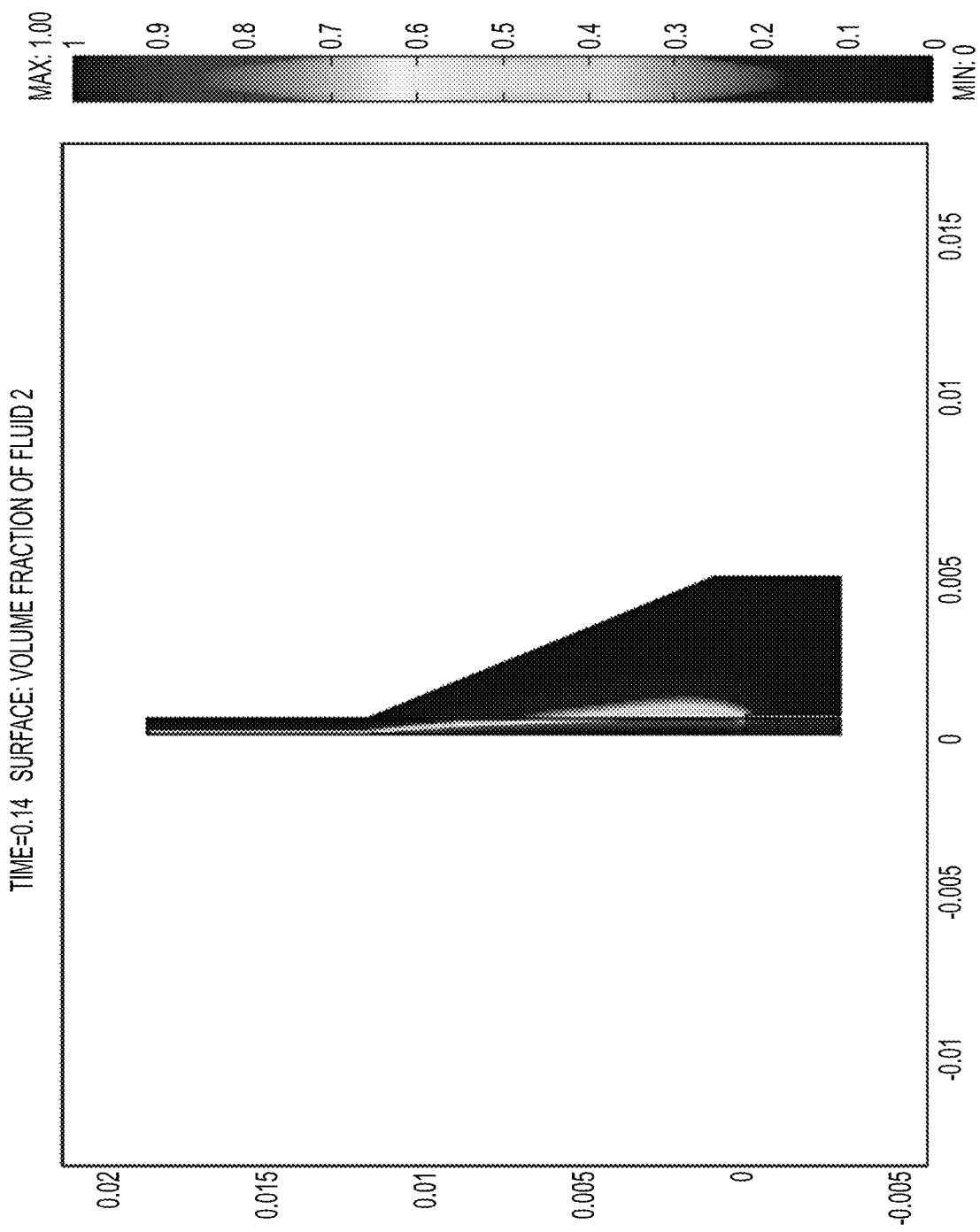

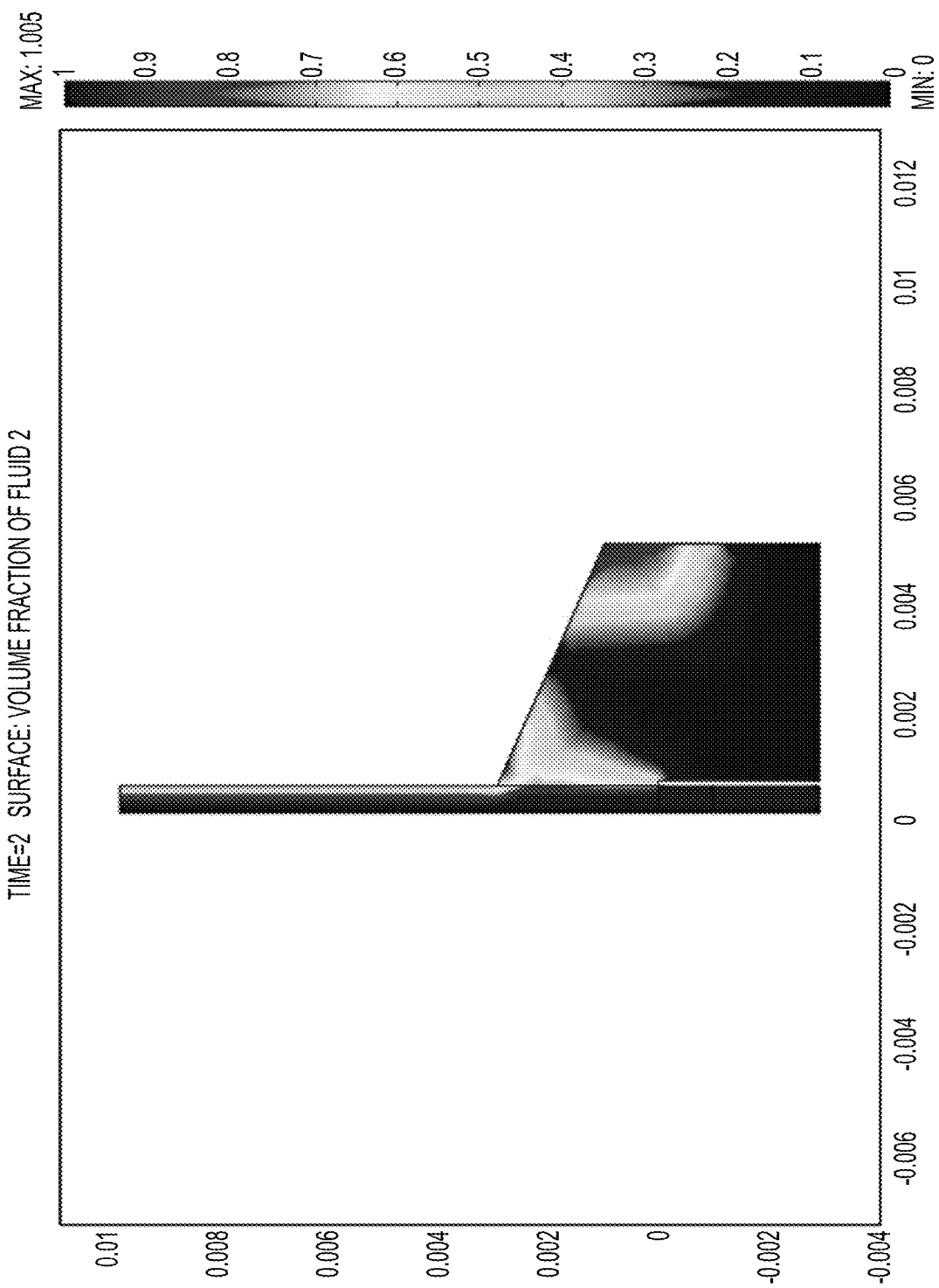

| ENCAPSULATION DEVICE | | |
|---|---|---|
| ITEM NO. | QTY | DESCRIPTION |
| 1 | 1 | LOCKING CAP |
| 2 | 1 | INNER CHAMBER |
| 3 | 1 | MAIN CHAMBER |
| 4 | 1 | GLASS TUBE RETENTION RING |
| 5 | 1 | HEAT-RESISTANT BOROSILICATE GLASS 6 mm OD X 1.2 mm ID, 12" LENGTH |
| 6 | 1 | 7/32" X 11/32" O-RING |
| 7 | 1 | 1/4" X 3/8" O-RING |
| 8 | 1 | BARB FITTING, 3/32" (2.4 mm) ID TUBING |
| 9 | 1 | BARB FITTING, 3/32" (2.4 mm) ID TUBING |
| 10 | 1 | MALE LUER INTEGRAL LOCK RING TO 200 SERIES BARB, 3/32" (2.4 mm) ID TUBING |
| 11 | 1 | SURFLASH IV CATHETER 1.70mm OD |

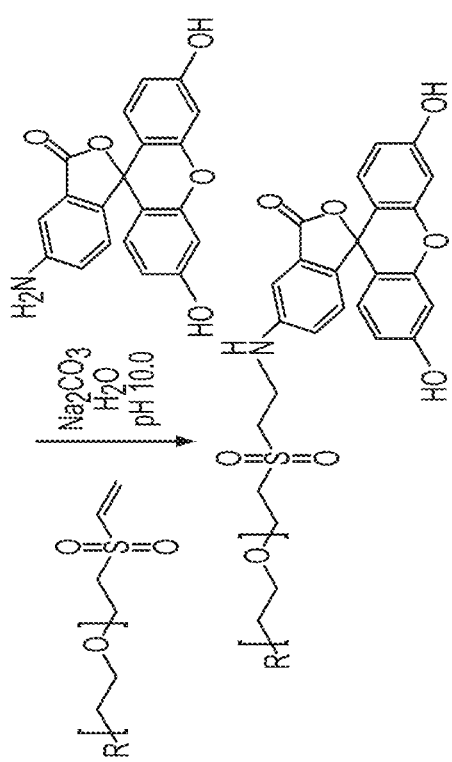
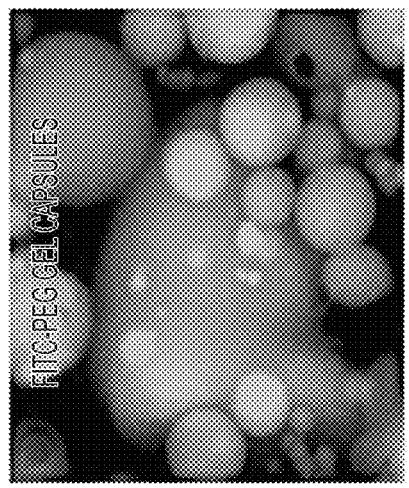
FIG. 14

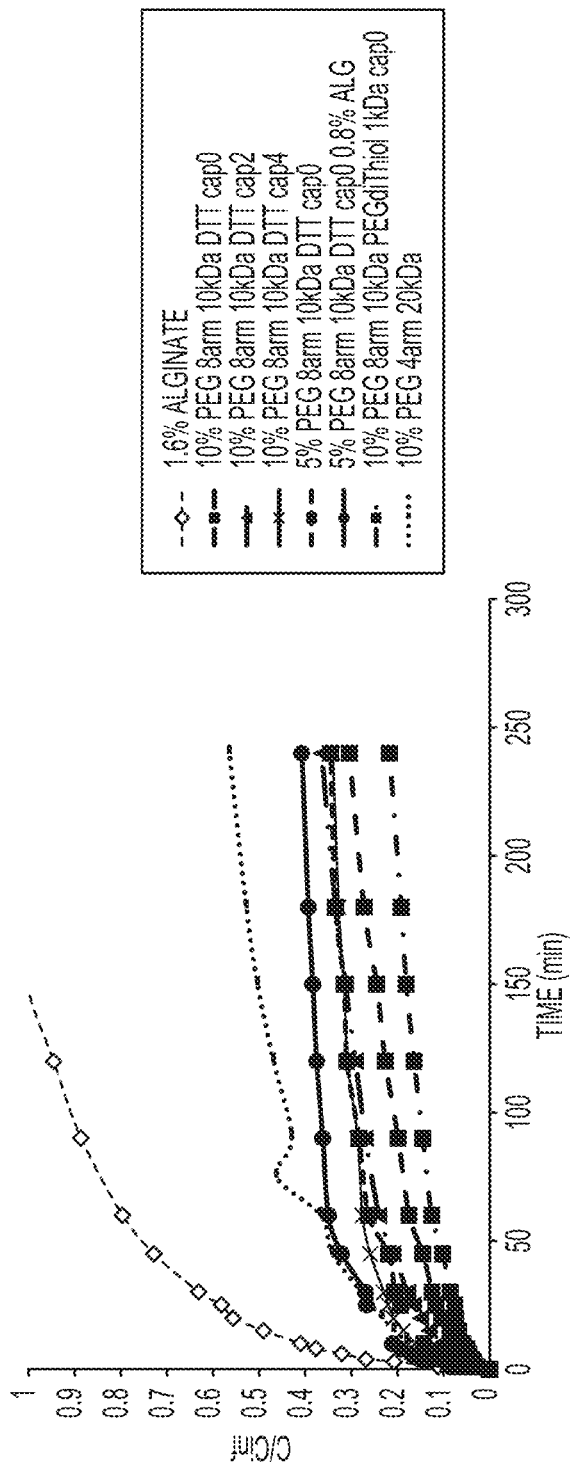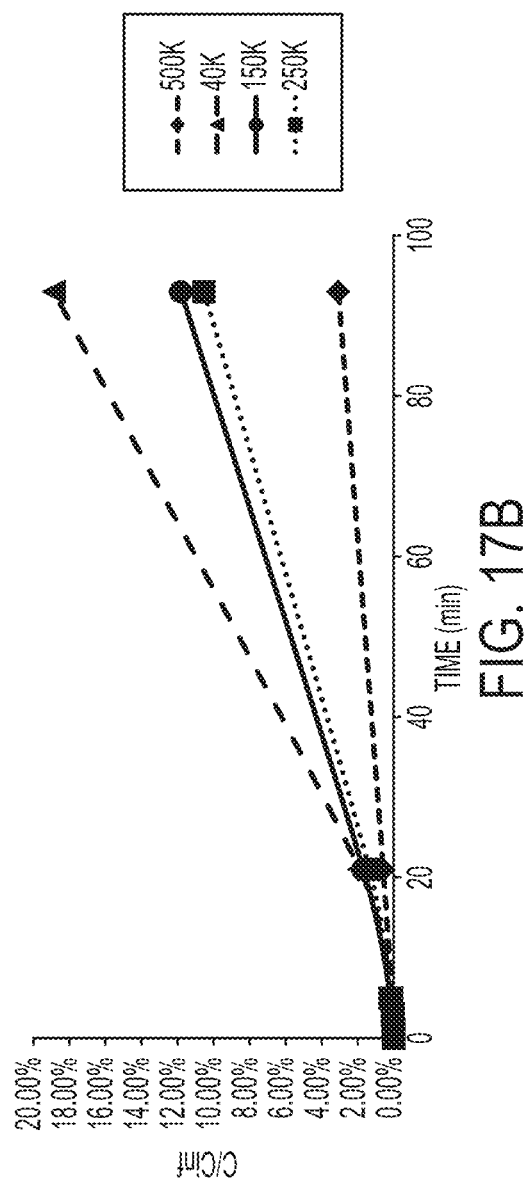

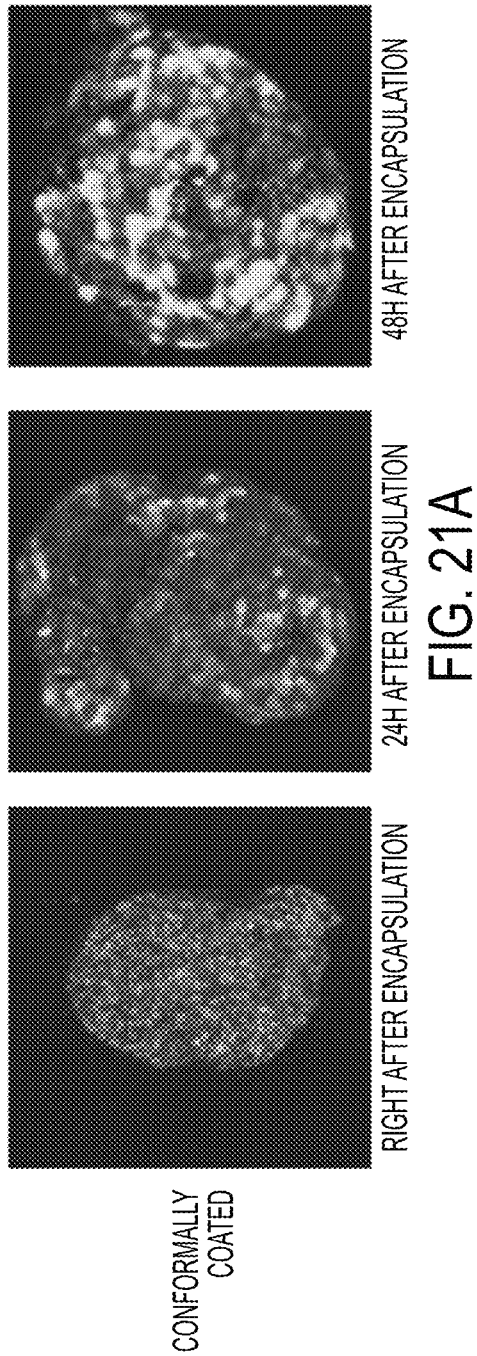
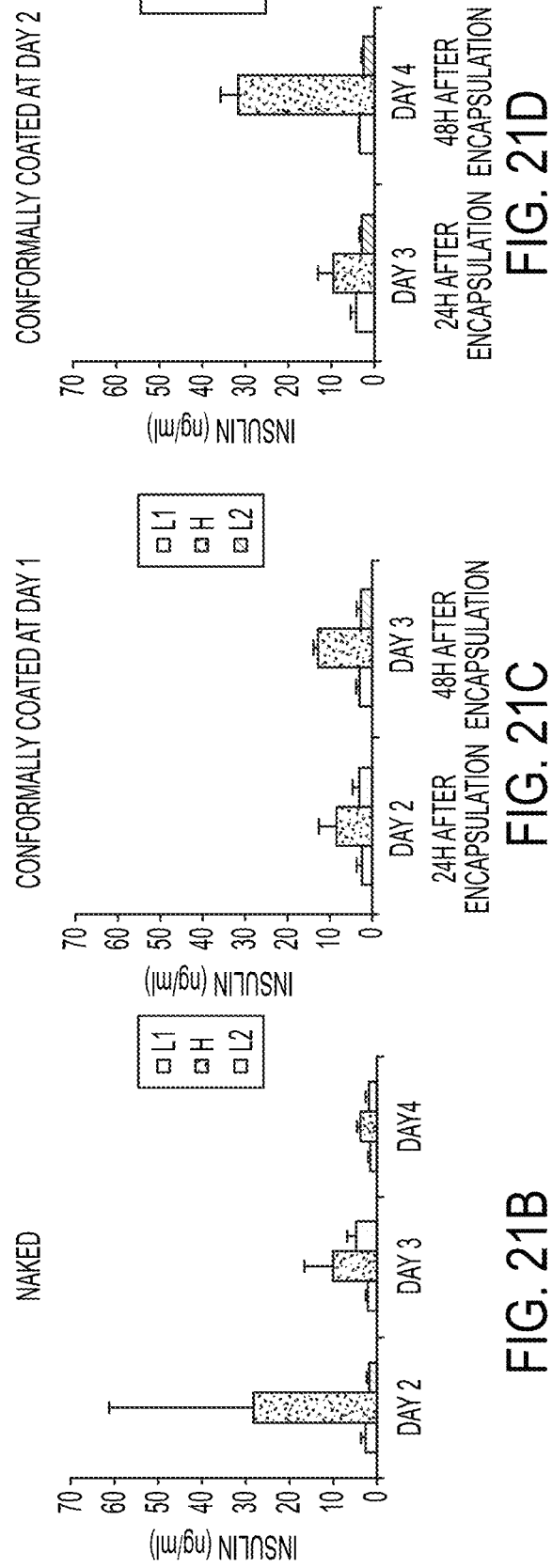
FIG. 21A
FIG. 21B
FIG. 21C
FIG. 21D

CONFORMAL COATING OF CELLS FOR IMMUNOISOLATION

RELATED APPLICATIONS

This application is a continuation application of U.S. patent application Ser. No. 14/114,690, filed Feb. 12, 2014 (now U.S. Pat. No. 10,660,987), which is a national stage application under 35 U.S.C. § 371 of International Patent Application No. PCT/US2012/035696, filed on Apr. 28, 2012, which claims the benefit of U.S. Provisional Patent Application No. 61/480,513, filed on Apr. 29, 2011. The disclosures of U.S. patent application Ser. No. 14/114,690, International Patent Application No. PCT/US2012/035696, and U.S. Provisional Patent Application No. 61/480,513 are hereby incorporated by reference in their entireties.

BACKGROUND

Cell encapsulation is a promising strategy for immunoisolating single cells and cell clusters and thus preventing any immune response that would compromise the functionality of the cells upon implantation. Bio-encapsulation has been extensively employed for novel therapeutic trials in the fields of diabetes, hemophilia, cancer and renal failure. However, most trials have not been fully successful for a combination of reasons:
- lack of reproducibility in encapsulation and cell isolation methods;
- lack of suitable encapsulation materials which should be biocompatible, mechanically and chemically stable, and have an appropriate pore cut-off size to allow nutrient and by-product flow in and out of the capsule while protecting encapsulated biomaterial from immune system effects;
- production of non-uniform or non-conformally coated capsules (affecting oxygen and nutrient diffusion through the capsule and therefore encapsulated cell viability);
- inability to scale up the encapsulation process from small animal studies to pre-clinical non-human primate studies; and
- choices of unfavorable transplantation sites.

Such challenges to encapsulation technology may be seen in the context of work in one of the most promising therapeutic fields for cell encapsulation: diabetes.

Diabetes results from the autoimmune destruction of pancreatic beta cells, one of the several cell types which make up the islets of Langherans. Over the course of their lifetimes, diabetic patients must frequently monitor and control blood glucose levels and administer insulin when they experience hyperglycemia, which has many collateral effects. Islet allo-transplantation is a very promising therapy to treat diabetic patients, but requires a lifetime of systemic immunosuppression to avoid allograft rejection.[1]

To avoid administration of immunosuppressive drugs at the systemic level, islet allografts can be immunoprotected by coating the cells for transplantation with a polymeric capsule that allows diffusion of oxygen, glucose and insulin while preventing cell-cell contact and diffusion of cytotoxic molecules, which otherwise would trigger the immune response against the graft and its ultimate rejection by the host.[2] Islets have a non-uniform size that varies from about 50 to 300 μm in diameter. Most coating procedures developed by others do not allow conformal coating of islets; capsule diameter is generally constant and independent of islet size, and is thus normally larger than 300 μm to guarantee coating of larger islets.[3] Because of the excess of cell-free coating material, the total volume of the islet implant is greatly increased such that the only appropriately-sized grafting site is the poorly-oxygenized abdominal cavity, which contributes to hypoxia of the encapsulated cells. Further, the thickness of the capsule increases the diffusion barrier to oxygen through the coating, also aggravating cell hypoxia, and delays glucose sensing and thus responsiveness of insulin secretion[4] (FIG. 1A). Most of these encapsulation methods are based on generation of droplets of the coating material mixed with islets through air-jet pump or electrostatic droplet generators.[5]

In contrast with encapsulation methods based on droplet generation, conformal coating of cell clusters of various diameters has been the focus of some recent investigations. Most of these methods are based on either (a) coating formation layer-by-layer directly onto cells (e.g., by chemical reaction or photo-polymerization) or (b) a purely hydrodynamic procedure, typically involving formation of particles by water in oil emulsion formation or by break-up of a water jet in oil by the fluid dynamic principle of Rayleigh-Plateau instability.[3,10] Using these methods, it is possible to generate water particles with a constant diameter uniquely dependent on the characteristics of the water and the oil phase, the surface tension between the two phases and the ratio of the hydrodynamic parameters of the two phases.[6,7,8,9] In the food and pharmaceutical industries, these methods have been extensively exploited to nano-encapsulate water-soluble drugs and other substances[8] and have only recently been extended to encapsulation of micron-size single cells and cell clusters, with some reported success, as described below.

Chabert M. and co-workers developed a microfluidic high-throughput system for encapsulating and self-sorting single cells based on the principle described above.[10] However, their system is designed for encapsulation and sorting of single cells (40 μm in diameter or less), and cannot be applied to cell clusters because of the micro-dimensions of their device, which would subject non-single cells to unaffordable shear stresses.

Garfinkel M. R. and co-workers developed another method to encapsulate islets by selectively withdrawing the islet-water phase from an external oil phase to create a thin coating on cell clusters. In this method, water phase jetting in the oil phase is achieved by suction of the water phase layer on top of the oil phase. In this design, turbulent flow is created in the water withdrawal area, ultimately leading to incomplete coating that necessitates a second round of encapsulation, increasing the amount of stress to which the cells are subjected and reducing the yield of the process.[11] Further, the gel polymerization is achieved through photo-polymerization, which may compromise long-term function of the coated cells.

Hubbell J. A. and co-workers developed an approach of coating by a chemical reaction directly on the cell surface, whereby a photosensitizer was adsorbed to the surface of islets, and the photosensitizer-treated islets were suspended in an aqueous solution of a photopolymerizable macromer (U.S. Pat. No. 6,911,227). Photoillumination of the islet suspension led to the polymerization and crosslinking of the macromer to create a conformal polymer gel bound to the surface of the islets.

In view of the above, there remains a need in the art for efficient, high-yield methods of conformally coating cells and cell clusters without compromising cell functionality.

SUMMARY OF THE INVENTION

The present invention relates to a method for conformally coating cells and cell clusters with hydrogels that are biocompatible, mechanically and chemically stable and porous, with an appropriate pore cut-off size. The methods of the invention are advantageously reproducible and result in a relatively high yield of coated versus non-coated cell clusters, without compromising cell functionality. The invention further provides conformal coating devices configured to perform the methods of the invention, methods of optimally utilizing said devices and purifying the coated islets, and coated biomaterials made by said methods.

Other advantages of the present invention include (1) overall decrease in encapsulated biomaterial graft volume, (2) minimal diffusion barriers for oxygen and nutrients through the capsules, (3) minimal delay in insulin responsiveness to glucose challenge, (4) minimal damage to the cell/cell cluster surface, allowing cell renewal and reorganization and (5) easy scale up from the bench to the clinic.

To achieve these and other effects, we exploited the purely hydrodynamic principle of Chabert et al., as described above. Specifically, in the absence of cells, a water phase is coaxially injected into an external oil phase and flowed through a focusing region such that the internal water phase can experience a transition from dripping to jetting within the oil phase and the water jet is elongated. The flow chamber that contains the two phases has a special focusing geometry that allows jet formation and acceleration (elongation) into a micrometer-size liquid jet. Jet dimension depends on the characteristics of the two phases and their fluid dynamic parameters. Surface tension between the water phase and the oil phase then triggers a Rayleigh-Plateau instability between the two phases that ultimately causes water jet break-up into microliter droplets with a constant size that depends on (a) the geometry of the device, (b) the ratio between the water and oil flow rates, (c) the ratio between the water and oil viscosities, and (d) the surface tension between the two phases.

When cell clusters are added to the inner water phase, they flow coaxially within the water jet (the water phase is flowing around the cluster since the system is axially symmetric). In the focusing regions, the elongation component of the flow allows for easy separation of the cell clusters. Once the jet breaks up, the cell clusters are coated with a thin water layer that is proportional to the size of the jet. Cell cluster-containing capsules thus have a diameter that is proportional to the cluster size and the thickness of the capsule depends only on the external fluid dynamic conditions.

Since cluster diameter is bigger than jet diameter and the water flow rate is constant, even if the cell density of the water phase is high, the clusters are separated from each other by the elongation component of the flow in the focusing region, which allows clusters to become individually aligned in the center of the jet prior to encapsulation. This allows encapsulation of individual cell clusters within single drops independent of cluster density.

There are several parameters which need to be controlled with this method in order to achieve conformal coating of biomaterials, such as cell clusters, with a precise thickness of coating: (1) water dripping to jetting transition, (2) jet break-up into microliter droplets (for cell cluster-free water phase) and into single cell cluster-containing droplets (for cell clusters in water phase), (3) internal polymerization of the coating material after jet break-up and before purification, and (4) efficient purification of coated cell clusters from the oil phase and from biomaterial-free coating material.

Each of these issues has been addressed using computational models and by experimental optimization, as described in more detail below.

BRIEF DESCRIPTION OF THE DRAWINGS

FIG. 1A. Schematic showing results of conformal coating by the methods of the invention (left) versus encapsulation by prior methods (right). The methods of the invention allow for coating of cells and cell clusters such that the size of the capsule is proportional to the size of the encapsulated cells/cell clusters. FIG. 1B. Schematic showing the procedure of conformal coating, in which the water phase containing the coating solution and the cell clusters is coaxially injected into an external oil phase and flowed through a focusing region such that the internal water phase can experience a transition from dripping to jetting within the oil phase and the water jet is elongated. Surface tension between the water phase and the oil phase then triggers a Rayleigh-Plateau instability between the two phases that ultimately causes water jet break-up into microliter droplets with a constant size, resulting in the coating of cell clusters with capsules that have a diameter proportional to cluster size. FIG. 1C. Computational model showing 2D axisymmetric geometry used with: "more focusing" (top left), "less focusing" (top middle), and different water injection points (top right). The mesh has been created by imposing a maximum size of the element in the central axis (r=0) equal to $10^{-5}$ m (bottom).

FIG. 2A, FIG. 2B, FIG. 2C, FIG. 3A, FIG. 3B, FIG. 3C, FIG. 4A, FIG. 4B, FIG. 4C, FIG. 5A, FIG. 5B, FIG. 5C, FIG. 6A, FIG. 6B, FIG. 6C, FIG. 7A, FIG. 7B, FIG. 7C, FIG. 8A, FIG. 8B, FIG. 8C, FIG. 9A, FIG. 9B, FIG. 9C, FIG. 10A, FIG. 10B, FIG. 10C, FIG. 11A, FIG. 11B, and FIG. 11C: Computational models with parameters as specified in Table 1. The outputs of each simulation are: surface plot of the water phase distribution within the oil phase at the last time point (FIG. 2A, FIG. 3A, FIG. 4A, FIG. 5A, FIG. 6A, FIG. 7A, FIG. 8A, FIG. 9A, FIG. 10A, and FIG. 11A); surface plot of the velocity profiles at the last time point (FIG. 2B, FIG. 3B, FIG. 4B, FIG. 5B, FIG. 6B, FIG. 7B, FIG. 8B, FIG. 9B, FIG. 10B, and FIG. 11B); and boundary plot (z-axis, at r=0) of the total stress in the r direction (Tr, FIG. 2C left, FIG. 3C left, FIG. 4C left, FIG. 5C left, FIG. 6C left, FIG. 7C left, FIG. 8C left, FIG. 9C left, FIG. 10C left, and FIG. 11C left) and the total stress in the z direction (Tz, FIG. 2C right, FIG. 3C right, FIG. 4C right, FIG. 5C right, FIG. 6C right, FIG. 7C right, FIG. 8C right, FIG. 9C right, FIG. 10C right, and FIG. 11C right) vs. the position along the z-axis.

FIG. 2A, FIG. 2B, and FIG. 2C: Model 1.
FIG. 3A, FIG. 3B, and FIG. 3C: Model 2.
FIG. 4A, FIG. 4B, and FIG. 4C: Model 3.
FIG. 5A, FIG. 5B, and FIG. 5C: Model 4.
FIG. 6A, FIG. 6B, and FIG. 6C: Model 5.
FIG. 7A, FIG. 7B, and FIG. 7C: Model 6.
FIG. 8A, FIG. 8B, and FIG. 8C: Model 7.
FIG. 9A, FIG. 9B, and FIG. 9C: Model 8.
FIG. 10A, FIG. 10B, and FIG. 10C: Model 9.
FIGS. 11A, 11B, and 11C: Model 10.

FIG. 12A. Assembly of the different parts and table with description of each part. FIG. 12B. Front plane section view.

FIG. 14: Left: schematic showing the labelling of PEG-dVS with fluoresceinamine by Michael type addition in a sodium carbonate buffer (ibis). Right: fluorescent microscope image of FITC-PEG gel capsules.

FIG. 16A. Low ratio of coated beads vs. empty polymer beads and big secondary beads. FIG. 16B. Low ratio of coated beads vs. empty polymer beads but smaller secondary beads. FIG. 16C. Higher ratio of coated beads vs. empty polymer beads and smaller secondary beads but low encapsulation efficiency. FIGS. 16D-16F. High ratio of coated beads vs. empty polymer beads, small secondary beads and high encapsulation efficiency (optimized protocol).

FIG. 17A and FIG. 17B: Permeability and permselectivity of hydrogels for conformal coating. FIG. 17A. Permeability of different ALGINATE- and PEG-based hydrogels to 10 kDa FITC dextran as $c/c_{inf}$ development over time. FIG. 17B. Permselectivity of PEG ALG DTT to different molecular weight FITC dextran as c/ci development over time.

FIG. 19A. Phase contrast microscopy of coated islets. FIG. 19B. Confocal images of FITC-labeled PEG coatings. FIG. 19C. Confocal images of 2000 kDa FITC dextran entrapped within PEG coatings. Blue: nuclear counterstain. Scale bars: 100 μm FIG. 20A. PEG-dVS 8arm 10 kDa cross-linked with DTT: conformally coated islets at different percentages of PEG and MVG alginate (ALG) vs. islets within PEG clumps and rods. FIG. 20B. Islets conformally coated with PEG-dVS 8arm 10 kDa cross-linked with DTT vs. linear HS-PEG-SH and vs. capping PEG-VS functional groups with beta-mercaptoethanol. FIG. 20C. Islets conformally coated with PEG-dVS 8arm 10 kDa cross-linked with DTT vs. multi-arm HS-PEG-SH vs. addition of MVG alginate (ALG). Low1: 60 mg/dL glucose, High: 300 mg/dL, Low2: 60 mg/dL.

FIG. 21A, FIG. 21B, FIG. 21C, and FIG. 21D: Effect of timing between isolation/encapsulation/functional evaluation on islet viability and functional response (insulin release upon glucose stimulation) of rat islets encapsulated with 5% PEG-dVS 8arm 10 kDa 0.8% MVG cross-linked with DTT (PEG ALG). FIG. 21A. Live (green)/Dead (red) staining of rat islets encapsulated with PEG ALG two days after isolation and imaged right after encapsulation (left), 24 hours after encapsulation (middle) or 48 hours after encapsulation (right). FIG. 21B. Functional response of naked islets 2, 3 or 4 days after isolation. FIG. 21C. Functional response of islets encapsulated with PEG ALG one day after isolation and evaluated 24 and 48 hours after encapsulation. FIG. 21D. Functional response of islets encapsulated with PEG ALG two days after isolation and evaluated 24 and 48 hours after encapsulation. L1: 60 mg/dL glucose, H: 300 mg/dL, L2: 60 mg/dL.

DETAILED DESCRIPTION OF THE INVENTION

The invention relates to methods and means for immunoisolating biomaterials, e.g., cells and cell clusters, to prevent immune rejection, inflammation, and/or autoimmune destruction while preserving cell functionality when the biomaterials are implanted into a subject.

In some embodiments, the invention provides a method for conformally coating a biomaterial with a coating material, comprising the steps of:
a) injecting a water phase within a coaxial oil phase in a coating device that allows for a transition from dripping to jetting and flow elongation of the water phase within the oil phase;
b) adding the biomaterial and the coating material to the water phase, wherein polymerization of the coating material occurs downstream of the jet breakup of the water phase into particles, resulting in the conformal coating of the biomaterial with the coating material; and
c) collecting the outflow of the coating device; and optionally, further comprising the step or steps of:
d) purifying the conformally coated biomaterial and biomaterial-free coating material from the oil phase; and
e) separating the conformally coated biomaterial from the biomaterial-free coating material.

Figure 1B:
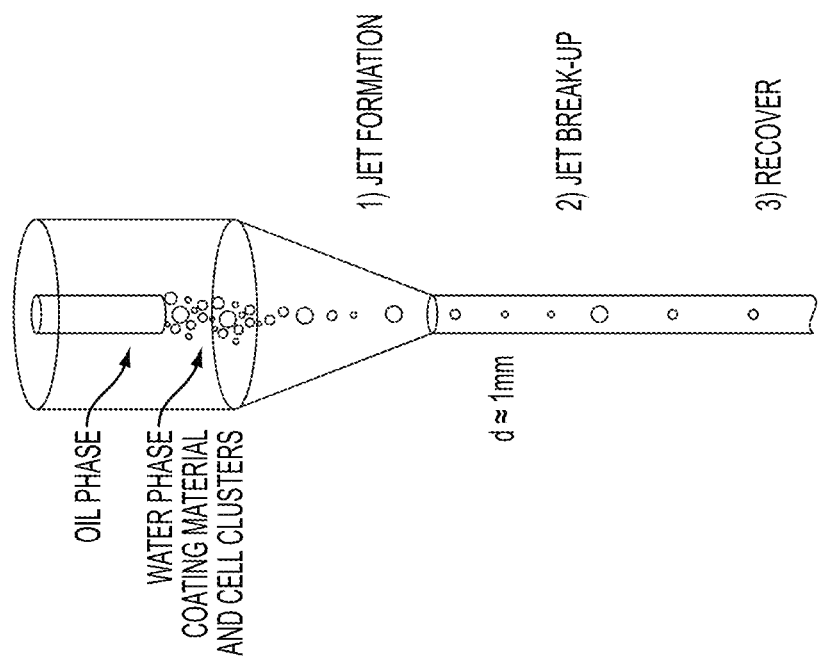
FIG. 1A, FIG. 1B, and FIG. 1C.
Figure 1A:
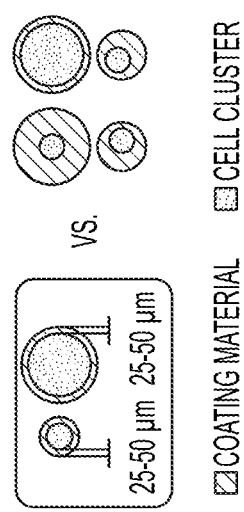

See, e.g., FIG. 1B.

The methods of the invention may be used to encapsulate any material that may benefit from immunoisolation when implanted into a subject. The material may be non-uniform. In one embodiment, the material that may benefit from immunoisolation is a biomaterial. In some embodiments, the methods of the invention are used to encapsulate one or more of cells, cell clusters, subcellular organelles, biologics such as proteins, nucleic acids and antibodies, and non-biologics (e.g., small molecules) such as drugs. In some embodiments, the methods of the invention are used to encapsulate cells and/or cell clusters. In a particular embodiment, the methods of the invention are used to encapsulate pancreatic islet cells and cell clusters.

In certain embodiments, the conformally coated cells and cell clusters may comprise one or more of autologous, heterologous, syngeneic, allogeneic, or xenogeneic pancreatic islets, alone or in combination with other cell types (e.g., Sertoli cells, mesenchymal and bone marrow derived cells, endothelial progenitor cells, stem cells, regulatory T cells $T_{reg}$, etc., each referred to generically as implant "helper cells") that provide growth factors and/or other beneficial agents for establishment, maintenance or expansion of the conformally coated cells, or otherwise to help the conformally coated cells deliver a therapeutic effect when implanted in a host. In one embodiment, the helper cells are mesenchymal stem cells.

As used herein, the term "host" refers to the recipient of implanted biomaterial and includes all animals. In one embodiment, the host is a mammal. In an exemplary embodiment, the host is human.

The methods of the invention may be used advantageously for conformal coating in cell therapy model systems. The conformally coated cells may deliver a therapeutic benefit, e.g., by expressing a therapeutic factor in vivo upon implantation. Examples of such cells include, but are not limited to, cells that produce: insulin to treat diabetes; dopamine to treat Parkinson's disease (Minquez-Castellanos et al., *J Neurol Neurosurg Psychiatry* in press (2007)); growth hormone to treat dwarfism (Chang et al., *Trends Biotechnol* 17:78-83 (1999)); factor VIII and factor IX (Chang et al., *Trends Biotechnol* 17, 78-83 (1999)) to treat hemophilia; and erythropoietin to treat anemia (Rinsch et al., *Kidney Intern* 62:1395-1401 (2002)). Many more beneficial cell produced factors or cellular/tissue activities may be imagined. In some embodiments, the conformally coated cells may express and/or deliver more than one therapeutic factor, or may comprise two or more cell types delivering one or more therapeutic factors. In some embodiments, the conformally coated cells also or alternatively express and/or deliver an antagonist, agonist, analog, derivative, chimera, fusion, or fragment of a therapeutic factor to deliver a therapeutic effect when implanted in a host.

In some embodiments, at least some of the conformally coated cells also or alternatively deliver a therapeutic effect without secreting a diffusible factor. In certain embodiments, the conformally coated cells provide an enzymatic activity that, for example, converts a substrate into a product having a beneficial effect, and/or metabolizes, sequesters, or absorbs a detrimental substance. In certain embodiments, the conformally coated cells deliver a therapeutic effect through a biological material-linked factor, such as a cell surface-linked factor.

In some embodiments, the conformally coated cells naturally deliver a therapeutic effect, without genetic modifications, upon implantation into a host. In some embodiments, the conformally coated cells are genetically engineered to deliver a therapeutic effect. As non-limiting examples, the cells may be transfected with expression vectors, or transduced with lentiviral vectors, that make the cells capable of expressing one or more therapeutic and/or helper cell factors. In another embodiment, the cells may comprise, consist of, or consist essentially of cells transfected with expression vectors that make the cells capable of expressing one or more therapeutic and/or helper cell factors. Such expression may be in a constitutive or in a regulated manner, e.g., in response to biological modulators in the bloodstream or tissues to which the cells are exposed.

In some embodiments, the cells for conformal coating are derived from cadaver tissue or from living tissue. In some embodiments, the cells are of non-mammalian or mammalian origin, non-human origin or human origin, self or non-self. The cells may be pluripotent, multipotent, totipotent, or differentiated embryonic or adult stem cells; primary differentiated cells; or immortalized cells, among other cell types. In certain embodiments, stem cells comprise, e.g., cells derived from cord blood, amniotic fluid, menstrual blood, placenta, Wharton's jelly, cytotropoblasts, and the like. The cells may also comprise any combination of the above-listed cell types.

Exemplary therapeutic factors which may be delivered by the conformally coated cells include, but are not limited to, one or more of: insulin, glucagon, erythropoietin; Factor VIII; Factor IX; hemoglobin; albumin; neurotransmitters such as dopamine, gamma-aminobutyric acid (GABA), glutamic acid, serotonin, norepinephrine, epinephrine, and acetylcholine; growth factors such as nerve growth factor (NGF), brain-derived neurotrophic factor (BDNF), neurotrophin-3 (NT-3), neurotrophin 4/5 (NT-4/5), ciliary neurotrophic factor (CNTF), glial cell line-derived neurotrophic factor (GDNF), cholinergic differentiation factor/leukemia inhibitory factor (CDF/LIF), epidermal growth factor (EGF), insulin-like growth factor (IGF), fibroblast growth factor (FGF), and platelet-derived growth factor (PDGF); pain inhibitors such as Substance P, catecholamines, dynorphins, endorphins, or enkephalins; hormones such as parathyroid hormone or growth hormone; immunomodulators such as granulocyte-macrophage colony stimulating factor (GM-CSF); neuromodulators; lymphokines; cytokines; cofactors; antibodies; aptamers; and enzymes. Choice of one or more therapeutic factors and the concentrations at which they are produced and released from the cells are dictated by the needs of the patient being treated, and may be readily determined empirically by the skilled practitioner.

In some embodiments, the conformally coated cells produce a therapeutic factor that has insulin-like or insulin-regulatory activity. In certain embodiments, the therapeutic factor is insulin. In certain embodiments, the therapeutic factor is a precursor form of insulin, such as preproinsulin or proinsulin. In certain embodiments, the therapeutic factor is an insulin chimeric or fusion protein.

In some embodiments, the therapeutic effect provided by the conformally coated cells comprises regulation of insulin levels in the blood. In certain embodiments, the therapeutic effect comprises regulation of glucose levels in the blood. In other embodiments, the therapeutic effect comprises regulation of levels of one or more other biological response regulators in the blood of the patient.

In some embodiments, the therapeutic factor(s) are released from the conformally coated cells due to the receipt of a stimulus or signal. For implanted cells, the stimulus or signal may be received from the host (e.g., changes in blood levels of glucose, hormones, metabolic signaling agents, chemical signaling molecules, etc.).

In some embodiments, the cells and/or cell clusters of the invention are generally uniform in size. In other embodiments, the cells and/or cell clusters of the invention are not uniform in size. In certain embodiments, the cells and/or cell clusters vary from 10 μm to 10000 μm in diameter; from 25 μm to 500 μm in diameter; or from 40 μm to 400 μm in diameter. In a particular embodiment, the cells and/or cell clusters vary from 50 to 300 μm in diameter. In some embodiments, the cells and/or cell clusters that vary from 50 to 300 μm in diameter comprise islet cells.

The coating material used in the conformal coating methods of the invention is biocompatible and is mechanically and chemically stable. Further, materials preferred for conformal coating do not interfere, or do not interfere substantially, with the function of the encapsulated biomaterial, and reduce, minimize or eliminate an immune response when the encapsulated biomaterial is implanted in a host. In certain embodiments, the coating material can be polymerized by internal gelation. In certain embodiments, the material used in the conformal coating methods of the invention is biodegradable.

In some embodiments, the coating material comprises one or more of polyethylene glycol (PEG), polyethylene oxide (PEO), poly(N-vinyl pyrrolidinone) (PVP), polyethyl oxazoline, polyvinyl alcohol (PVA), polythyloxazoline (PEOX), poly(amino acids), and Biodritin®; polysaccharides such as alginate, hyaluronic acid, chondroitin sulfate, dextran, dextran sulfate, heparin, heparin sulfate, heparan sulfate, chitosan, gellan gum, xantham gum, guar gum, water soluble cellulose derivatives and carrageenan; and proteins such as gelatin, collagen and albumin. In certain embodiments, the coating material is polyethylene glycol (PEG).

In certain embodiments, the coating material is mono-armed. In certain embodiments, the coating material is multi-armed.

In some embodiments, the conformal coating has permeability characteristics that allow for exchange of nutrients and cellular by-products and release of therapeutic factors, but that may also preclude host immune effector molecules and/or other undesired elements from entering the capsules. In certain embodiments, the conformal coating comprises pores with a cut-off size of 100, 110, 120, 130, 140, 145, 150, 155, 160, 170, 180, 190, 200, 210, 220, 230, 240 or 250 kDa. In certain embodiments, the conformal coating comprises pores with a cut-off size of 150 kDa. In certain embodiments, the conformal coating comprises pores with a cut-off size of up to 500 kDa.

The thickness of the conformal coating does not depend on the size/diameter of the coated material. In some embodiments, the thickness of the coating ranges from 1 μm to 100 μm, from 5 μm to 50 μm, or from 8 μm to 25 μm. In some embodiments, the thickness of the coating ranges from 25-50 μm. In some embodiments, the thickness of the coating ranges from 10-20 μm.

In some embodiments, the coating is visualized by labeling the coating material with a detectable marker. The marker may be, e.g., a fluorescent, enzymatic, chemiluminescent, or epitopic label. In certain embodiments, the coating may be visualized by entrapping high molecular weight FITC dextran within the coating material. In a particular embodiment, the labeled coating material is PEG-dVS-FITC.

In some embodiments, the coating material may be chemically altered to contain functional groups. In some embodiments, the functional groups help stabilize the coating. Further, the coating material may comprise therapeutic factors or other molecules that associate with such therapeutic factors, such as receptors or affinity agents (see, e.g., Kim et al., *Biomacromolecules* 4(5):1214-1223 (2003)). Therapeutic factors may be incorporated into the coating material via covalent cross-linking, emulsification, ionic interactions, specific affinity interations, simple entrapment, or any combination thereof.

In one embodiment, the coating material comprises anti-inflammatory molecules to reduce the host inflammatory response upon implantation of the conformally coated cells. Exemplary anti-inflammatory agents include corticosteroids (dexamethasone, cortisol, prednisolone, loteprednol etabonate, flucinolone acetonide, and others), interleukin-1 (IL-1), interleukin-10 (IL-10), alpha 1-antitrypsin (AAT), lisofylline, pentoxyfilline, COX-2 inhibitors, interleukin-1 receptor antagonist peptide (IRAP), interleukin-10 (IL-10), alpha 1-antitrypsin (AAT), TGF-beta; antibodies to IL-1, interferon-gamma, and TNF-alpha; anti-tissue factor, and complement inhibitors. In some embodiments, the coating material comprises extracellular matrix (ECM) molecules such as collagen type I or IV, laminin, fibronectin, or arginine-glycine-aspartate peptides (Beck et al., *Tissue Eng* 13(3):1-11 (2007)). In some embodiments, the anti-inflammatory and/or ECM molecules are tethered to the surface of the coating material. In certain embodiments, the molecules are coated or encapsulated for slow release.

Conformal coating of the biomaterial takes place in a coating device. As used herein, the term "coating device" refers to any device that is capable of conformally coating a biomaterial. In some embodiments, the coating device is a device that allows for a transition from dripping to jetting and elongation of a water phase within a non-miscible (e.g., oil) phase, wherein the water phase undergoes jet breakup into particles. In some embodiments, the coating device is a flow chamber comprising one or more oil phase inlets, one or more water phase inlets (which may be the same as or different from the oil phase inlets), and one or more flow focusing regions downstream of the inlets where co-flowing jets of the oil phase focus the water phase. The flow chamber may further comprise one or more channels downstream of the flow focusing region(s). The diameter of the water phase channel(s) may be, e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 mm in diameter. The diameter of the oil phase channel(s) may be, e.g., 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mm in diameter. In certain embodiments, the diameter of the oil phase channel(s) may be up to 100 mm. The length of the channel(s) may be, e.g., 5, 6, 7, 8, 9, 10, 11, 12, 13, 14 or 15 mm. The channels may lead to one or more outlets from the flow chamber. See, e.g., FIGS. 12A and 12B for examples of details in designing and fabricating the flow chamber.

In some embodiments, the device provides flow focusing from a channel of 10d to a channel of d (⅒ restriction in diameter to allow transition from dripping to jetting). In certain embodiments, d ranges from 0.5-10 mm. In certain embodiments, d ranges from 1-4 mm. In a particular embodiment, d is around 1 mm. In some embodiments, the focusing angle of the device ranges from 100 to 5 degrees (more to less focusing). In certain embodiments, the focusing angle ranges from 90 to 10 degrees. In certain embodiments, the focusing angle is greater than 10, 20, 30, 40, 50, 55, 60, 65, 70, 80, or 90 degrees. In certain embodiments, the focusing angle of the device is about 60 degrees. In some embodiments, the flow focusing region is 50, 60, 70, 80, 90, 100, 110, 120, 130, 140, or 150 mm long. In certain embodiments, the flow focusing region is 100 mm long.

In some embodiments, the diameter of the external oil phase chamber (cylinder) is 1-20 mm. In some embodiments, the diameter of the external oil phase chamber is 5, 6, 7, 8, 9, 10, 11, 12, 13, 14, or 15 mm. In a particular embodiment, the diameter of the external oil phase chamber is 10 mm. In some embodiments, the external oil phase chamber is fed by a lateral port 1, 2, 3, 4, 5, 6, 7, 8, 9, or 10 mm upstream (cylinder axial distance) of the coaxial injection port for the water phase. In certain embodiments, the lateral port is 5 mm upstream of the water phase injection port. In certain embodiments, the external oil phase chamber is fed by more than one lateral port 1, 2, 3, 4, 5, 6, 7, 8, 9, or 10 mm upstream (cylinder axial distance) of the coaxial injection port for the water phase.

In some embodiments, the tip of the water injection needle co-localizes with the base of the focusing region of the device. In some embodiments, the tip of the water injection needle is positioned about 0, 0.1, 0.2, 0.3, 0.4, 0.5, 0.6, 0.7, 0.8, 0.9, 1, 2, 3, 4, or 5 mm upstream or downstream (cylinder axial distance) of the base of the focusing region of the device. In a particular embodiment, the tip of the water injection needle is positioned about 0.5 mm upstream of the focusing region.

In a particular embodiment, the device is characterized by an external oil phase chamber 10 mm in diameter, fed by a lateral port 5 mm upstream of the coaxial injection port for the water phase, which is 0.5 mm upstream of the flow focusing region, and flow focusing occurs in a channel that constricts from 10 mm to 1 mm in diameter and is 100 mm in length, with a focusing angle of 60 degrees.

In some embodiments, the device is able to coat cells and/or cell clusters of greater than 40, 50, 60, 70, 80, 90, 100, 150, 200, 250, 300, 350, 400, 450, 500, 550, 600, 650, 700, 750, 800, 850, 900, 950, or 1000 μm in diameter. In certain embodiments, the device is able to coat cells and/or cell clusters of greater than 40 μm in diameter. In some embodiments, the device is able to coat cells and/or cell clusters of up to 1000 μm in diameter.

In some embodiments, the water phase flow, the oil phase flow, or both, are maintained by a peristaltic pump. In some embodiments, the water phase flow, the oil phase flow, or both, are maintained by a syringe pump. In one embodiment, the water phase flow is maintained by a syringe pump and the oil phase flow is maintained by a peristaltic pump.

In some embodiments, the conformal coating methods of the invention do not involve: (1) generation of droplets of the coating material mixed with islets through air-jet pump or electrostatic droplet generators; (2) coating formation layer by layer directly on the cells (3) coating by a chemical reaction directly on the cell surface; and/or (3) photopolymerization.

In some embodiments in which cells and/or cell clusters are the biomaterial to be conformally coated, the concentration of cells/cell clusters added to the water phase may range from 100-1,000,000 cells/ml, 500-750,000 cells/ml, 1,000-500,000 cells/ml, or 2,500-250,000 cells/ml. In certain embodiments, the concentration of cells/cell clusters added to the water phase ranges from 5,000 to 100,000 cells/ml. In a particular embodiment, the 5,000 to 200,000 cells/ml added to the water phase are pancreatic islet cells, which may optionally be enriched for insulin secreting beta cells or cell clusters.

The water phase may comprise a surfactant. In some embodiments, the surfactant comprises one or more of, e.g., Pluronic™ (F-68 and/or F-127) and PEG-PPS block co-polymers. In one embodiment, the surfactant is Pluronic® F-68 (polyoxyethylene-polyoxypropylene block copolymer). In some embodiments, the surfactant concentration in the water phase ranges from 0-10%, 0-8%, 0-6%, 0-5%, 0-4%, 0-3%, 0-2.5%, 0-2%, 0-1.5%, or 0-1%. In certain embodiments, the surfactant concentration ranges from 0 to 5%. In one embodiment, the surfactant concentration is 2%. In another embodiment, the surfactant concentration is 1%.

The water phase may comprise an agent to coat the surface of the islet and prevent clumping. In some embodiments, the agent comprises medium viscosity G-groups alginate (MVG). In certain embodiments, the agent comprises sodium alginate with 60% guluronate (G) and 200000-300000 g/mol viscosity (PRONOVA UP MVG, Product #4200106, NovaMatrix, Sandvika, Norway). In other embodiments, the agent additionally or alternatively comprises a charged synthetic or natural polymeric (e.g., polyacrylic acid) or non-polymeric (e.g., heparin) compound.

In some embodiments, the pH of the water phase is 1, 1.5, 2, 2.5, 3, 3.5, 4, 4.5, 5, 5.5, 6, 6.1, 6.2, 6.3, 6.4, 6.5, 6.6, 6.7, 6.8, 6.9, 7, 7.5, or 8. In particular embodiments, the pH of the water phase is 4.5, 5.5, 6.5, or 7. In one embodiment, the pH of the water phase is 6-7.

In certain embodiments, the water phase comprises cells/cell clusters in media, surfactant, and one or more thiolating or reducing reagents (which may be, e.g., mono- or multi-functional agents that are linear or multi-armed). In some embodiments, the cells/cell clusters comprise islet cells, the media is serum-free or is Hanks' Balanced Salt Solution (HBSS), the surfactant is Pluronic® F-68 (polyoxyethylene-polyoxypropylene block copolymer), and/or the thiolating or reducing reagent is DTT. In some embodiments, the water phase comprises 5-10% PEG (e.g., 5% or 10% PEG), 0-0.8% medium viscosity G-groups alginate (e.g., 0, 0.4% or 0.8% MVG), 0-2% Pluronic® F-68 (polyoxyethylene-polyoxypropylene block copolymer) (e.g., 0%, 1% or 2% Pluronic® F-68 (polyoxyethylene-polyoxypropylene block copolymer)), 50,000-100,000 islet cells/ml (e.g., 50,000 or 75,000 islet cells/nil), and 0.31-0.62% w/v DTT (e.g., 0.31% or 0.62% w/v DTT) in serum-free media or HBSS without $Ca^{2+}$ and $Mg^{2+}$ at pH 4.5-7.4 (e.g., pH 4.5, 5, 5.5, 6, 6.5, 7 or 7.4); and the oil phase comprises 0-0.2% triethanolamine (e.g., 0%, 0.02% or 0.2% triethanolamine). The conformal coating methods of the invention encompass any combinations of these values. In certain embodiments, for example, the water phase comprises 5-10% PEG, 2% Pluronic® F-68 (polyoxyethylene-polyoxypropylene block copolymer), 75,000 islet cells/ml, and 0.31-0.62% w/v DTT in serum-free media at pH 6.5. In other embodiments, the water phase comprises 5-10% PEG, 75,000 islet cells/ml, and 0.31-0.62% w/v DTT in HBSS without $Ca^{2+}$ and $Mg^{2+}$ at pH 4.5 or 5. In other embodiments, the water phase comprises 5% or 10% PEG, 0.8% medium viscosity G-groups alginate, 2% Pluronic® F-68 (polyoxyethylene-polyoxypropylene block copolymer), 50,000 islet cells/ml, and 0.31 or 0.62% w/v DTT in calcium and magnesium free HBSS at pH 7. In other embodiments, the water phase comprises 5% or 10% PEG, 0.8% medium viscosity G-groups alginate, 75,000 islet cells/ml, and 0.31 or 0.62% w/v DTT in calcium and magnesium free HBSS at pH 6. In one embodiment, the invention provides a method wherein the water phase comprises 10% PEG, 2% Pluronic® F-68 (polyoxyethylene-polyoxypropylene block copolymer), 75,000 islet cells/ml and 0.62% w/v DTT in serum-free media at pH 6.5; wherein the oil phase comprises PPG with 10% Span® 80, wherein said oil phase optionally further comprises 0.02% triethanolamine (TEA). In another particular embodiment, the invention provides a method wherein the water phase comprises 5% PEG, 1% Pluronic® F-68 (polyoxyethylene-polyoxypropylene block copolymer), 75,000 islet cells/ml and 0.31% w/v DTT in HBSS without $Ca^{2+}$ and $Mg^{2+}$ at pH 4-6; wherein the oil phase comprises PPG with 10% Span® 80 (sorbitan oleate), wherein said oil phase optionally further comprises 0.02% triethanolamine. In another particular embodiment, the invention provides a method wherein the water phase comprises 5% PEG, 1% Pluronic® F-68 (polyoxyethylene-polyoxypropylene block copolymer), 0.8% medium viscosity G-groups alginate, 75,000 islet cells/ml and 0.31% w/v DTT in HBSS without $Ca^{2+}$ and $Mg^{2+}$ at pH 7; wherein the oil phase comprises PPG with 10% Span® 80 (sorbitan oleate), wherein said oil phase optionally further comprises 0.02% triethanolamine. In another particular embodiment, the invention provides a method wherein the water phase comprises 5% PEG, 0.8% medium viscosity G-groups alginate, 75,000 islet cells/ml and 0.31% w/v DTT in HBSS without $Ca^{2+}$ and $Mg^{2+}$ at pH 6; wherein the oil phase comprises PPG with 10% Span® 80 (sorbitan oleate), wherein said oil phase optionally further comprises 0.02% triethanolamine. In another particular embodiment, the invention provides a method wherein the water phase comprises 5% PEG, 0.8% medium viscosity G-groups alginate, 75,000 islet cells/ml and 0.31% w/v DTT in HBSS without $Ca^{2+}$ and $Mg^{2+}$ at pH 5; wherein the oil phase comprises PPG with 10% Span® 80 (sorbitan oleate), wherein said oil phase optionally further comprises 0.02% triethanolamine. In any of the embodiments described herein, the oil phase may optionally comprise, e.g., 0.01%-0.5% triethanolamine, e.g., 0.02%-0.2% ethanolamine. In some embodiments, the oil phase may optionally comprise 0.2% triethanolamine, e.g., instead of 0.02% triethanolamine.

In certain embodiments, the oil phase comprises one or more of, e.g., polypropylene glycol (PPG) or mineral oil with a viscosity of at least 2.5 times more than the viscosity of the water phase. The oil phase may further comprise one or more agents selected from, e.g., Span® 80 (sorbitan oleate) and/or triethanolamine.

In some embodiments, the oil phase comprises PPG. In certain embodiments, the oil phase comprises PPG with 1-20%, 5-15%, 6-14%, 7-13%, 8-12%, 9-11%, or 10% Span® 80 (sorbitan oleate), and/or 0-2%, 0.005-0.5%, 0.008-0.05%, or 0.01-0.02% triethanolamine. In a particular embodiment, the oil phase comprises PPG with 10% Span® 80 (sorbitan oleate). In some embodiments, the oil phase comprising PPG with 10% Span® 80 (sorbitan oleate) further comprises 0.01%, 0.02%, or 0.2% triethanolamine (TEA).

In some embodiments, the flow rates of the water phase (Qw) and the oil phase (Qo) are respectively selected from: 10 μl/min and 3.5 ml/min; 1 μl/min and 3.5 ml/min; 10 μl/min and 7 ml/min; 50 μl/min and 0.5 ml/min; 50 μl/min and 2.5 ml/min; 150 μl/min and 0.5 ml/min; and 150 μl/min and 2.5 ml/min. In some embodiments, air is injected before the water phase to allow stabilization of the water in the oil jet. In certain embodiments, air is drawn into an injection catheter containing the water phase, such that the bubble of air can be injected into the oil phase prior to injection of the water phase into the oil phase to help visualize the beginning of the water phase.

The flow rates of the water phase and the oil phase may be adjusted over time. In some embodiments, the water phase is reduced over time while the oil phase is increased. In a particular embodiment, the water phase enters the oil phase first at 50 μl/min and is then reduced to 10 μl/min. In certain embodiments, the oil phase rate is gradually increased from 0.5 to 3.5 ml/min while the water phase is decreased and is then kept constant for the entire encapsulation process, or the oil phase rate is kept constant at 3.5 ml/min throughout the encapsulation process.

In some embodiments, the ratio of the oil phase velocity to the water phase velocity is between 70 and 500. In certain embodiments, the ratio is 50, 60, 70, 80, 90, 100, 150, 200, 250, 300, 310, 320, 330, 340, 350, 360, 370, 380, 390, 400, 450, or 500. In a particular embodiment, the ratio is 350.

In some embodiments, the ratio of the oil phase viscosity to the water phase viscosity is between 2.5 and 100. In certain embodiments, the ratio is 2.5, 3, 3.1, 3.2, 3.3, 3.4, 3.5, 3.6, 3.7, 3.8, 3.9, 4, 5, 10, 20, 30, 40, 50, 60, 70, 80, 90, or 100. In a particular embodiment, the ratio is 3.5.

Upon breakup of the water jet, the material for encapsulation (e.g., cells and/or cell clusters) is coated with a thin, coating material-containing water layer that is proportional to the size of the jet, allowing for conformal coating. The coated cells/cell clusters are then collected from the outflow of the coating device. In some embodiments, after collection, the coated cells and/or cell clusters are kept under stirring for, e.g., 1-30, 5-20, or 8-12 minutes to avoid coalescence until polymerization of the coating is completed. In some embodiments, the stirring takes place at between 4 and 25° C. In particular embodiments, the stirring takes place at 25° C. In some embodiments, the stirring speed is between 50-500 rpm or 100-300 rpm. In one embodiment, the coated cells and/or cell clusters are kept stirring for about 10 minutes. In another embodiment, the coated cells and/or cell clusters are collected in a vessel and allowed to settle by gravity. In some embodiments, the coated cells and/or cell clusters are kept without stirring in the outer bath for, e.g., 1-30, 5-20, or 8-12 minutes to allow polymerization of the coating to complete. In some embodiments, the coated cells and/or cell clusters are collected within a vessel comprising PPG and 10% Span® 80 (sorbitan oleate) and 0.02% TEA. In other embodiments, the coated cells and/or cell clusters are collected within a vessel comprising PPG and 10% Span® 80 (sorbitan oleate) and 0.2% TEA. In other embodiments, the coated cells and/or cell clusters are collected within a vessel comprising PPG and 0.02 or 0.2% TEA.

The oil phase may then be separated from the water phase. In some embodiments, the separation occurs through centrifugation and/or hexane extraction. In certain embodiments, said centrifugation comprises the steps of:
a) centrifuging the outflow to separate the conformally coated biomaterial and biomaterial-free coating material from the oil phase; and
b) removing the oil phase supernatant from the conformally coated biomaterial and biomaterial-free coating material.

In certain embodiments, the oil phase is separated from the water phase by centrifugation for 5-20 minutes at 1000-2000 rpm followed by 1-10 minutes at 100-1000 g. In a particular embodiment, the oil phase is separated from the water phase by centrifugation for 5 minutes at 1500 rpm followed by 1 minute at 500 g.

In some embodiments, the hexane extraction comprises the steps of:
a) resuspending the conformally coated biomaterial and biomaterial-free coating material in a composition comprising hexane;
b) centrifuging the mixture of step a) to separate the conformally coated biomaterial and biomaterial-free coating material from the hexane; and
c) removing the hexane supernatant.

In some embodiments, the hexane extraction further or alternatively comprises the steps of:
d) resuspending the conformally coated biomaterial and biomaterial-free coating material in a composition comprising hexane and a buffer;
e) centrifuging the mixture of step d) to separate the conformally coated biomaterial and biomaterial-free coating material from the hexane and buffer; and
f) removing the hexane/buffer supernatant.

The conformally coated biomaterial and biomaterial-free coating material may then be resuspended in an aqueous solution, e.g., in buffer.

In other embodiments, the hexane extraction further or alternatively comprises the steps of:
d) resuspending the conformally coated biomaterial and biomaterial-free coating material in a composition comprising or consisting of hexane;
e) adding the buffer to the hexane composition and mixing, e.g., by inverting the vessel;
f) centrifuging the mixture of step e) to separate the conformally coated biomaterial and biomaterial-free coating material from the hexane composition and buffer; and
g) removing the hexane/buffer supernatant.

In some embodiments, a second extraction with hexane may be performed.

In a particular embodiment, the hexane extraction comprises the steps of:
a) resuspending the conformally coated biomaterial and biomaterial-free coating material in a composition comprising hexane;
b) adding buffer (HBSS without Ca' and Mg') to the coated biomaterial and biomaterial-free coating material and hexane mix and mixing, e.g., by inverting the vessel
c) centrifuging the mixture of step b) for 5 min at 500 g;
d) removing the hexane and buffer supernatant, adding buffer (HBSS without $Ca^{2+}$ and $Mg^{2+}$) and resuspending the conformally coated biomaterial and biomaterial-free coating material;
e) centrifuging the mixture of step d) for 30 sec at 500 g;
f) removing the buffer supernatant, adding hexane and resuspending the conformally coated biomaterial and biomaterial-free coating material; adding buffer (HBSS without $Ca^{2+}$ and $Mg^{2+}$) and resuspending the material;
g) centrifuging the mixture of step f) for 30 sec at 500 g; and
h) removing the hexane/PBS supernatant.

The conformally coated biomaterial and biomaterial-free coating material may then be resuspended in PBS.

It may be desirable to separate the coated cells and/or cell clusters from biomaterial-free coating material. This separation may be achieved by any of a number of size or density based separation techniques well known in the art, e.g., by gradient centrifugation. In certain embodiments, coated cells and/or cell clusters are further purified from coating material by gradient centrifugation, comprising the steps of:
a) layering solutions to form a density gradient capable of separating the conformally coated biomaterial and the biomaterial-free coating material;
b) applying the conformally coated biomaterial and biomaterial-free coating material to the density gradient;
c) centrifuging the density gradient to separate the conformally coated biomaterial from the biomaterial-free coating material; and
d) removing the part of the gradient containing the biomaterial-free coating material.

In one embodiment, the solutions layered to form the gradient are at the densities of (1) 1-1.1 g/ml, e.g., 1.042 g/ml, and (2) media. In some embodiments, more than 50, 60, 70, 80, 85, 90, 91, 92, 93, 94, 95, 96, 97, 98, 99, or 100% of the coated biomaterial is purified from the biomaterial-free coating material. In a certain embodiment, more than 95% of the coated biomaterial is purified from the biomaterial-free coating material.

In a particular embodiment, the invention provides a method wherein the water phase comprises 10% PEG, 2% Pluronic® F-68 (polyoxyethylene-polyoxypropylene block copolymer), and 0.62% w/v DTT in serum-free media at pH 6.5;
wherein the oil phase comprises PPG with 10% Span® 80 (sorbitan oleate), wherein said oil phase optionally comprises 0.02% triethanolamine. In another particular embodiment, the invention provides a method wherein the water phase comprises 5% PEG, 1% Pluronic® F-68 (polyoxyethylene-polyoxypropylene block copolymer), and 0.31% w/v DTT in HBSS at pH 5.5; wherein the oil phase comprises PPG with 10% Span® 80 (sorbitan oleate), wherein said oil phase optionally comprises 0.02% triethanolamine. In another particular embodiment, the invention provides a method wherein the water phase comprises 5% PEG, 1% Pluronic® F-68 (polyoxyethylene-polyoxypropylene block copolymer), 0.8% medium viscosity G-groups alginate and 0.31% w/v DTT in HBSS at pH 7; wherein the oil phase comprises PPG with 10% Span® 80 (sorbitan oleate), wherein said oil phase optionally comprises 0.02% triethanolamine. In another particular embodiment, the invention provides a method wherein the water phase comprises 5% PEG, 0.8% medium viscosity G-groups alginate and 0.31% w/v DTT in HBSS at pH 4-7; wherein the oil phase comprises PPG with 10% Span® 80 (sorbitan oleate), wherein said oil phase optionally comprises 0.02-2% triethanolamine (e.g., 0.02% or 0.2% triethanolamine). In any of these embodiments, the coating device may comprise a flow chamber comprising a "more focusing" flow focusing region with constriction of channel inner diameter from 10 mm to 1 mm with a focusing angle of 60 degrees, and a channel downstream of the flow focusing region that is about 1 mm in diameter and 100 mm in length; wherein the method comprises the steps of:
a) applying the oil phase to the flow chamber;
b) injecting air into the flow chamber through a needle whose tip is localized 0.5 mm upstream of the base of the focusing region;
c) injecting the water phase into the flow chamber through said needle, wherein the water phase is first injected at 50 µl/min and then reduced to 10 µl/min, while the oil phase is maintained at 3.5 ml/min, such that the surface tension between the water and the oil phase causes the water jet to break up into microliter sized droplets comprising the conformally coated biomaterial and biomaterial-free coating material;
d) collecting the outflow from the flow chamber;
e) centrifuging the outflow to separate the conformally coated biomaterial and biomaterial-free coating material from the oil phase;
f) removing the oil phase supernatant from the conformally coated biomaterial and biomaterial-free coating material;
g) resuspending the conformally coated biomaterial and biomaterial-free coating material in a composition comprising hexane, and adding buffer and mixing (e.g., by inverting the vessel);
h) centrifuging the mixture of step g) to separate the conformally coated biomaterial and biomaterial-free coating material from the hexane and buffer;
i) removing the hexane/buffer supernatant;
j) resuspending the conformally coated biomaterial and biomaterial-free coating material in a composition comprising a buffer;
k) centrifuging the mixture of step j) to separate the conformally coated biomaterial and biomaterial-free coating material from the buffer;
l) removing the buffer supernatant;
m) optionally repeating steps g)-j);
n) layering solutions to form a density gradient capable of separating the conformally coated biomaterial and the biomaterial-free coating material;
o) applying the conformally coated biomaterial and biomaterial-free coating material to the density gradient;
p) centrifuging the density gradient to separate the conformally coated biomaterial from the biomaterial-free coating material; and
q) removing the part of the gradient containing the biomaterial-free coating material.

In certain embodiments, the islet cells and/or the PEG are added to the water phase before injecting it into the flow chamber, or alternatively, after injecting it into the flow chamber.

If the coating material bears a fluorescent label, the conformally coated cells and/or cell clusters can be visualized by, e.g., fluorescence microscopy, fluorocytometry, flow cytometric cell sorting technology, or by a fluorescent plate reader. In some embodiments, the fluorescently-labeled conformally coated cells can be detected and/or isolated using, e.g., flow cytometry or FACS.

In some embodiments, the methods of the invention are scaled up to conformally coat at least 50,000; 100,000; 150,000; 200,000; 300,000; 400,000; 500,000; 600,000; 700,000; 800,000; 900,000; or 1,000,000 cells and/or cell clusters at the same time. In some embodiments, this scale up is achieved by performing the methods of the invention in a series of chambers. In one embodiment, the methods of the invention are scaled up by assembling a series of parallel vertical chambers in, e.g., a radial configuration in which radial flow to each chamber feeds the water phase to each separate chamber with comparable hydrodynamic flow characteristics. In some embodiments, the coated cells and/or cell clusters and biomaterial-free coating material from each chamber are collected in separate containers. In some embodiments, the coated cells and/or cell clusters and biomaterial-free coating material from each chamber are collected in the same container and purified at the same time.

In some embodiments, the methods of the invention provide conformal coating of greater than 15, 20, 25, 30, 35, 40, 45, 50, 55, 60, 65, 70, 75, 80, 85, 90, 91, 92, 93, 94, 95, 96, 97, 98, 99, or 100% of the biomaterial introduced into the coating device. In certain embodiments, the methods of the invention provide conformal coating of greater than 95% of the introduced biomaterial.

In some embodiments, the viability and function of coated cells and/or cell clusters are assessed by any of a number of methods well known in the art, e.g., MTT assay, live/dead staining, and/or (in the case of islets) static glucose stimulation of perifusion. In some embodiments, said assessment takes place before implantation of the cells. In cases where the coated cells are islets, immunoprotection of the transplanted islets by conformal coating may be evaluated by, e.g., monitoring the glucose level and/or weight of the transplanted patient, and/or by histological evaluation.

The invention further provides methods of treating a disorder in a patient, comprising the step of implanting into the patient the conformally coated biomaterial isolated by the methods referred to herein. These disorders include, but are not limited to: diabetes, hemophilia, renal failure, amyloidosis, immune system disorders, inflammations, chronic pain, arthritis, hypertension, disorders of the nervous system, metabolic disorders, endocrine disorders, lymphoproliferative disorders, myeloproliferative disorders, myelodysplastic syndromes, stem cell disorders, phagocyte disorders, histiocytic disorders, abnormalities of erythrocytes or platelets, plasma cell disorders, acute leukemias, chronic leukemias, malignancies (breast carcinoma, Ewing Sarcoma, neuroblastoma, renal cell carcinoma, etc.), hypothyroidism, hypopituitarism, hypogonadism, graft failure, graft versus host disease (GVD), veno-occlusive disease, side effects from pre-transplant chemotherapy (such as excessive bleeding, infertility, and renal as well as lung and heart complications), and other disorders and diseases that would be recognized by the skilled practitioner.

As referred to herein, the term "patient" refers to the recipient of a therapeutic treatment and includes all animals. In one embodiment, the patient is a mammal. In a particular embodiment, the patient is human.

The conformally coated biomaterial produced by the methods of the invention may be implanted in any appropriate place within a patient. The biomaterial may be implanted in naïve or pre-vascularized sites; in physiological or transformed sites; and within tissue and organs or adjacent to them. In certain embodiments, the implant location may be, for example, intraomental (in an omental pouch), subcutaneous, intraperitoneal, intramuscular, or renal subcapsular. In one embodiment, the implant location is subcutaneous. In some embodiments, the implant location is not the abdominal cavity.

In some embodiments, conformally coated biomaterial produced by the methods of the invention is placed in a device before implantation in a patient, to decrease the patient immune response and/or to prolong the survival of the cells. The device may be any device suitable for the implantation of biological material in a patient, e.g., the device as described in U.S. Publication No. 2006/0024276 or in U.S. Pat. No. 6,716,246, each of which is incorporated herein by reference in its entirety. In some embodiments, the conformally coated biomaterial is implanted within or adjacent to a natural or synthetic, biodegradable or non-biodegradable scaffolding substrate.

In order that this invention may be better understood, the following examples are set forth. These examples are for purposes of illustration only and are not to be construed as limiting the scope of the invention in any manner.

EXAMPLES

Example 1: Computational Model

A computational model in Comsol Multiphysics (two-level set function of the chemical engineering modulus) has been developed to determine the effect of different geometrical parameters ("more focusing" and "less focusing" flow chamber and different injection points of the water phase into the oil phase) and fluid dynamic parameters (ratio between water and oil flow rates, ratio between water and oil viscosities, and interfacial tension between the two phases) on the transition from dripping to jetting of the water phase, the size of the final water jet, and the total stress acting in the center of the water jet.

Figure 1C:
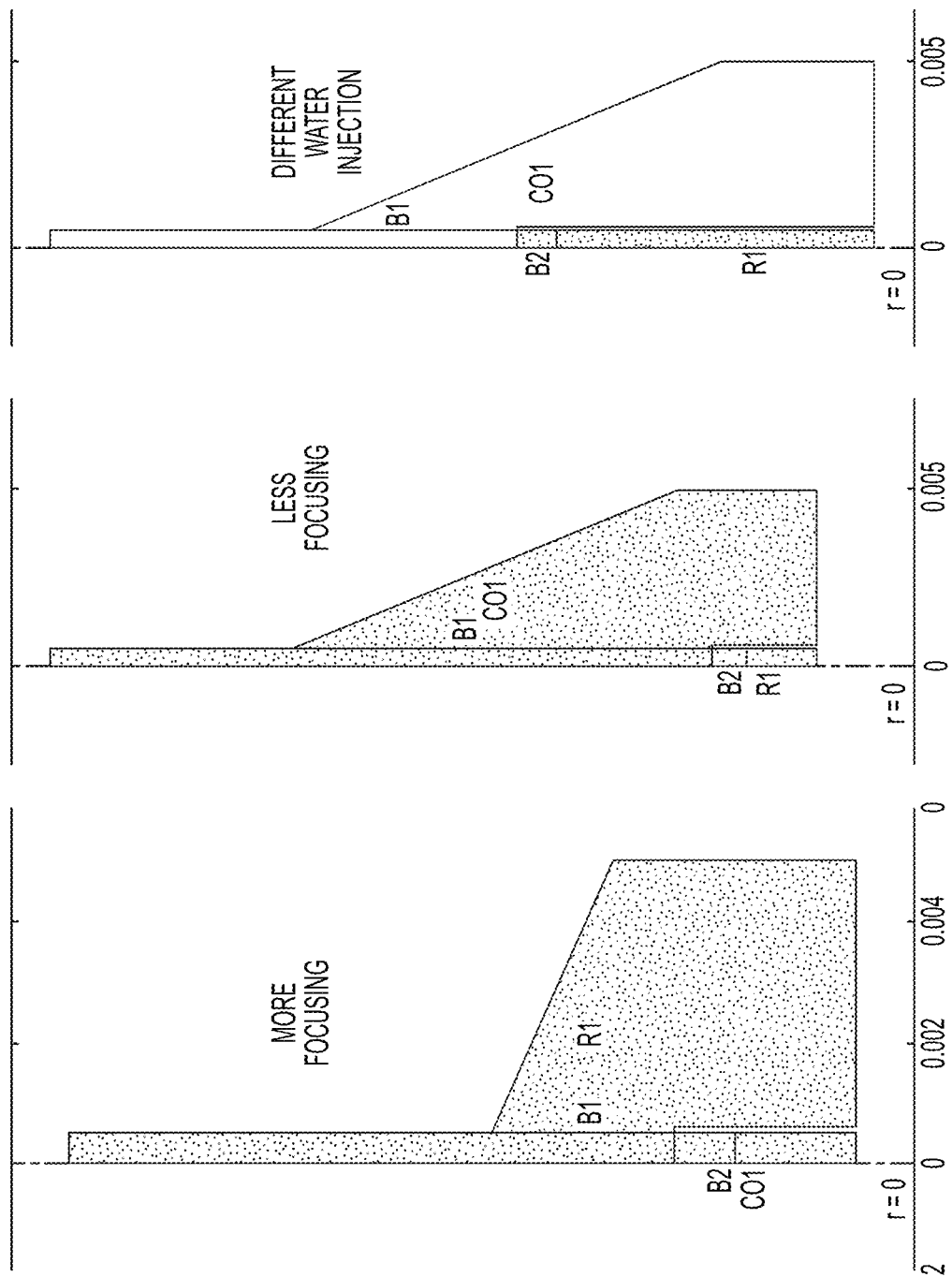
Figure 2A:
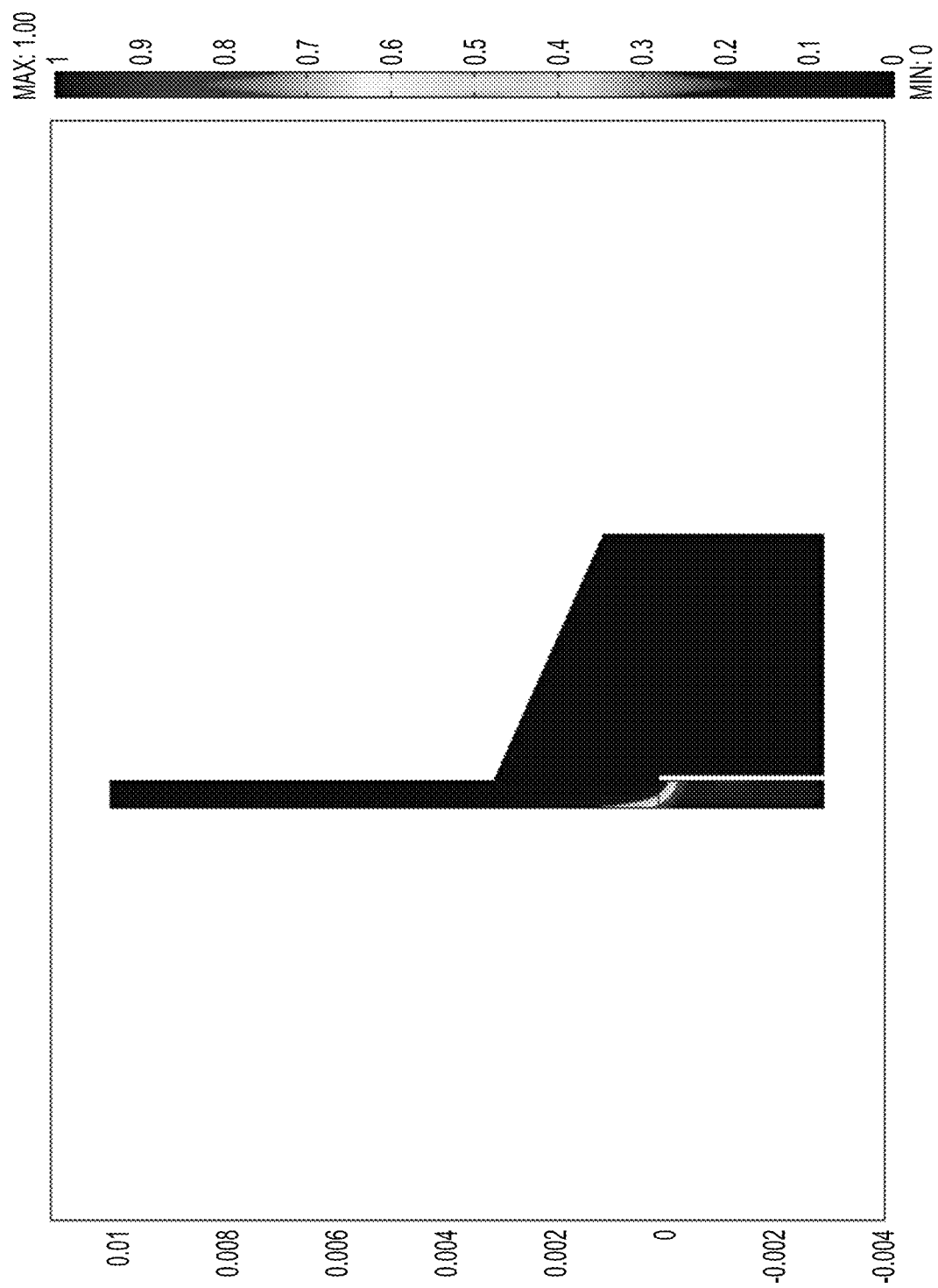
Figure 2B:
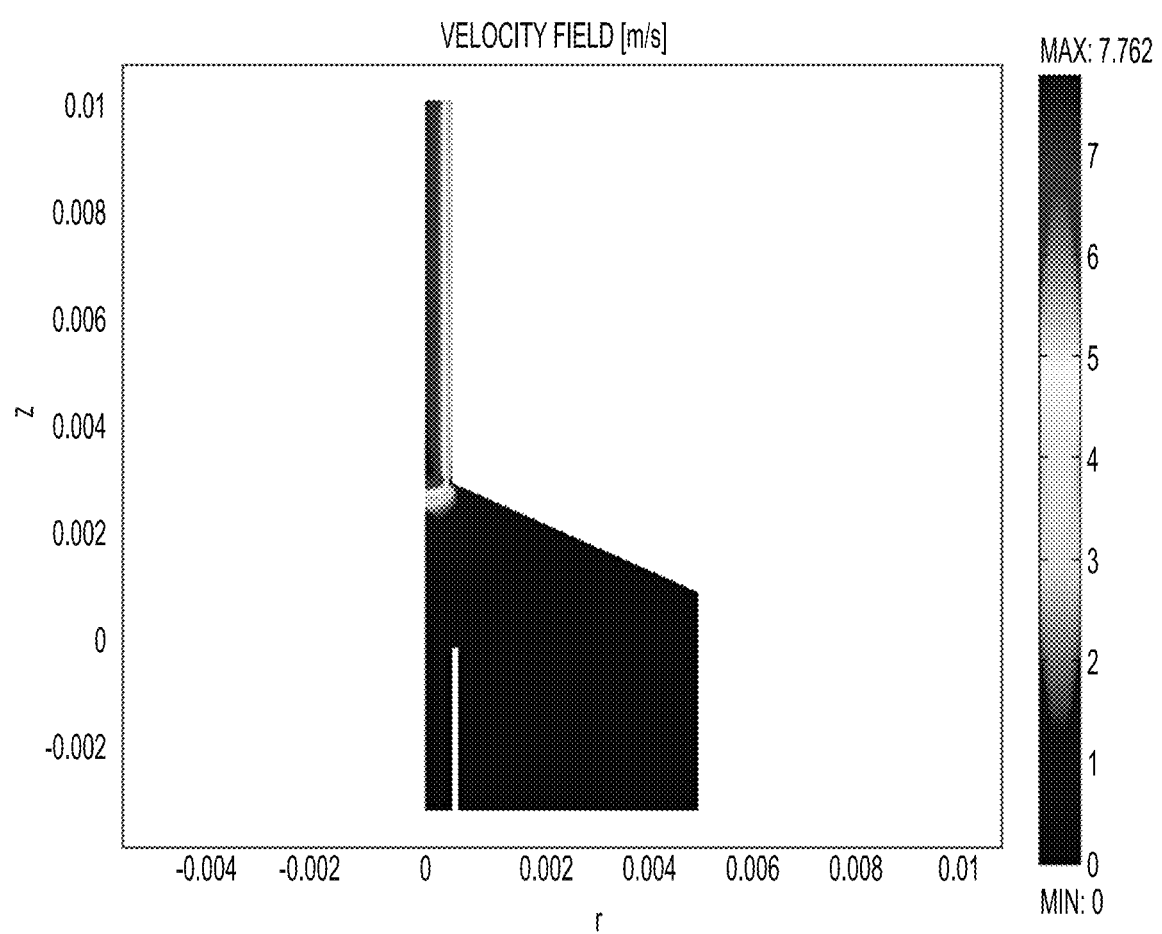
Figure 2C:
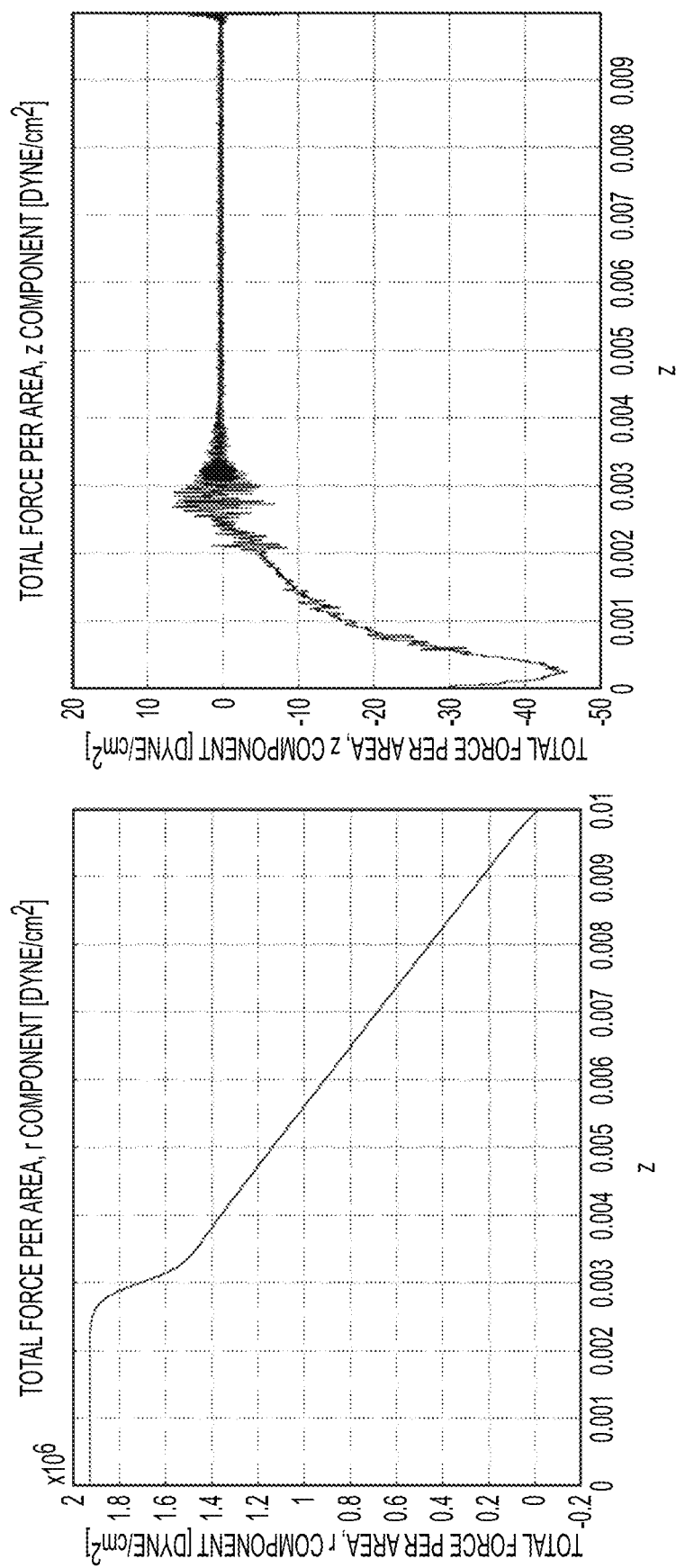
Figure 3A:
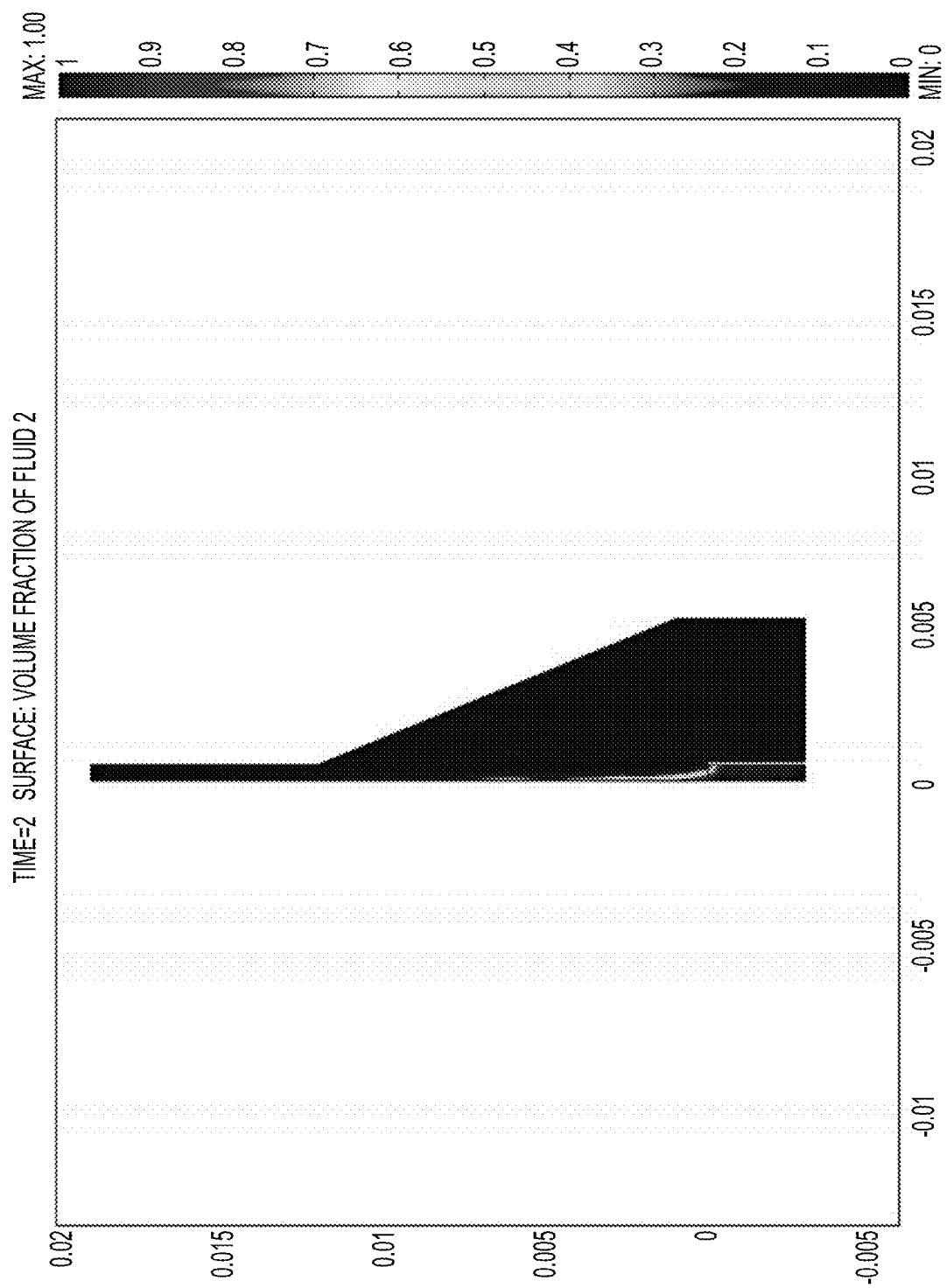
Figure 3B:
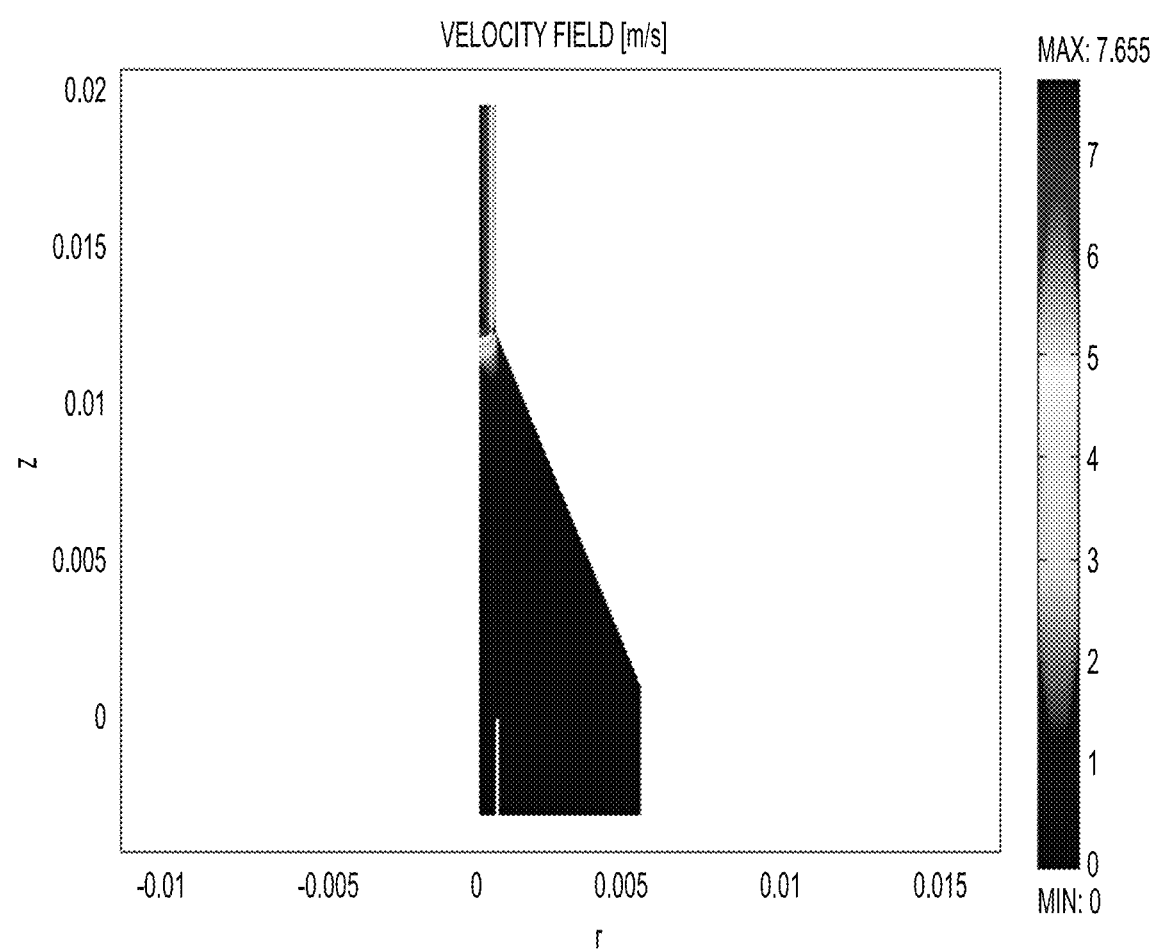
Figure 3C:
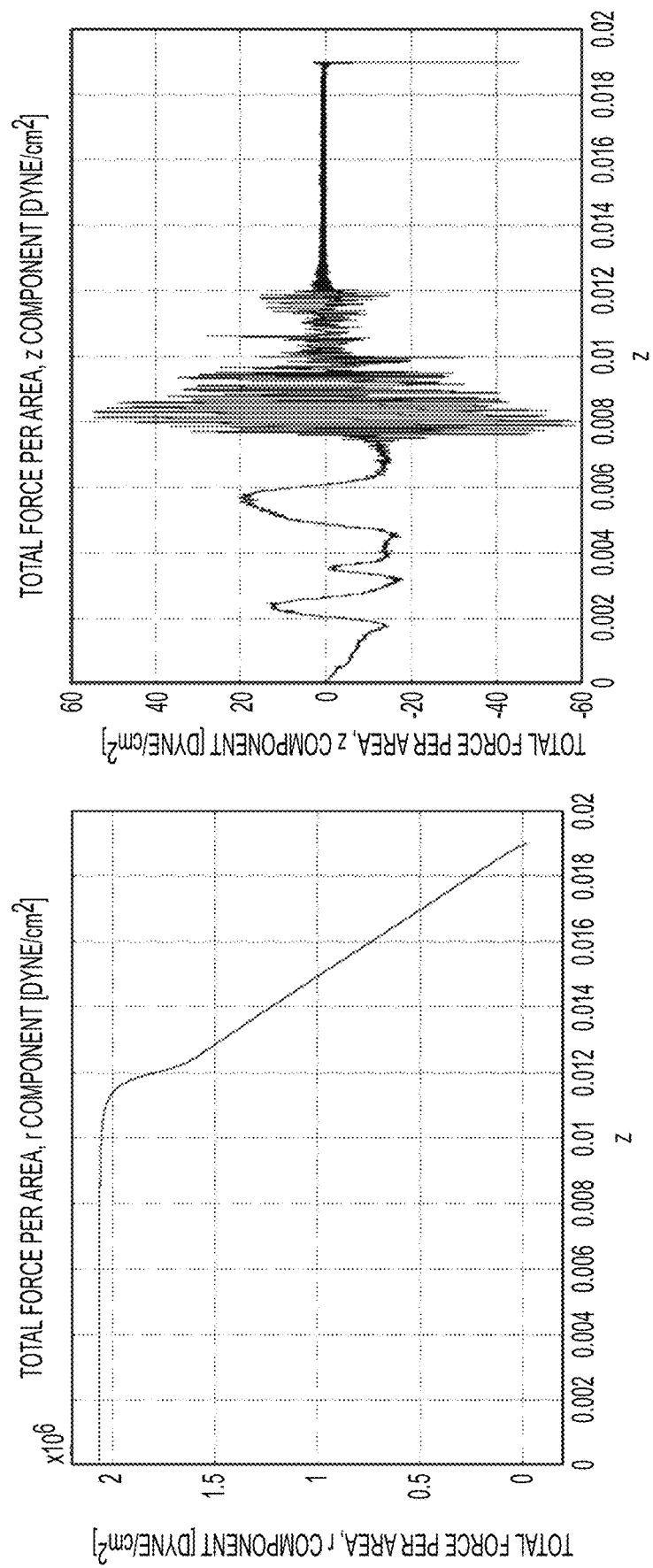
Figure 4A:
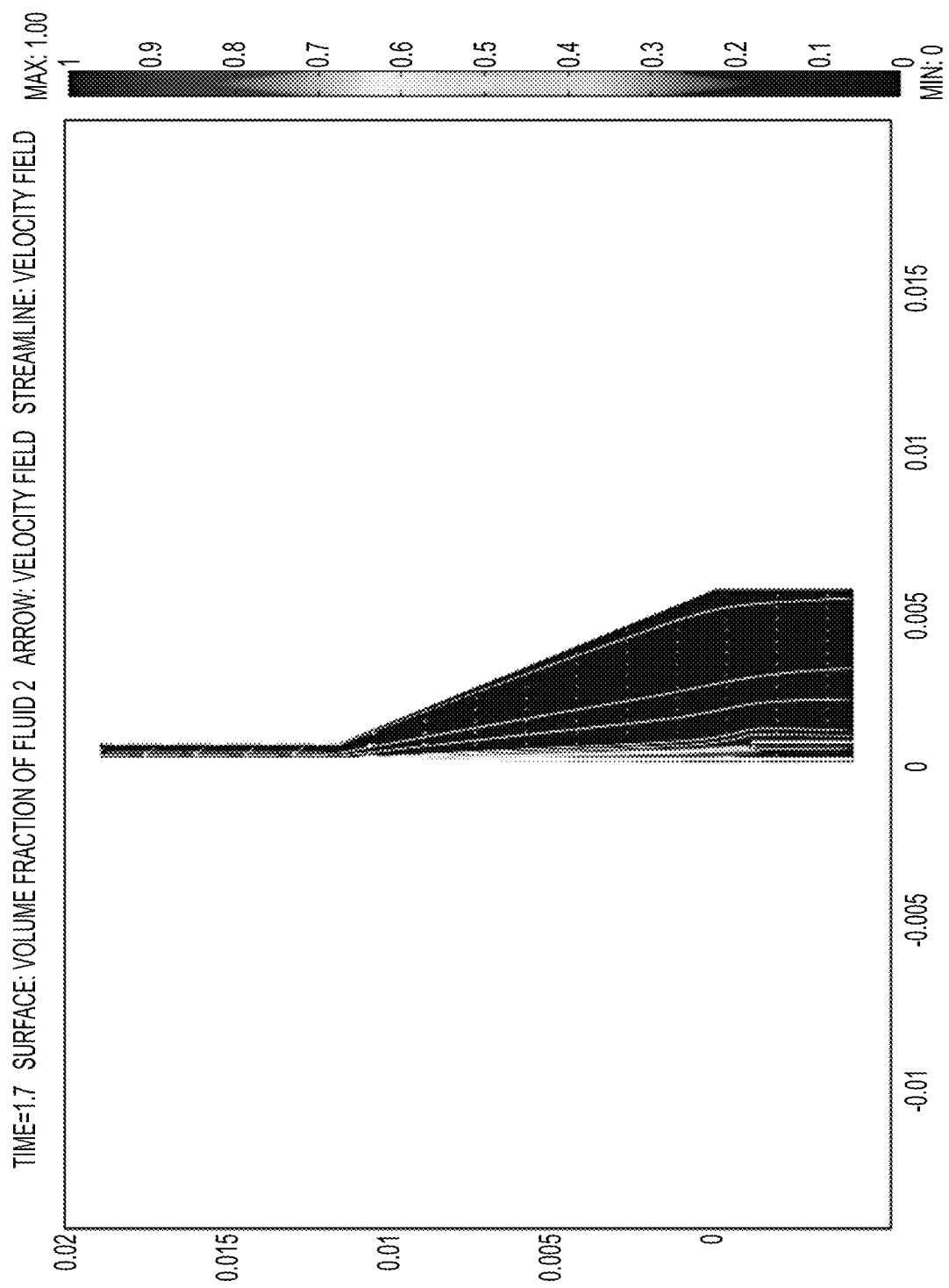
Figure 4B:
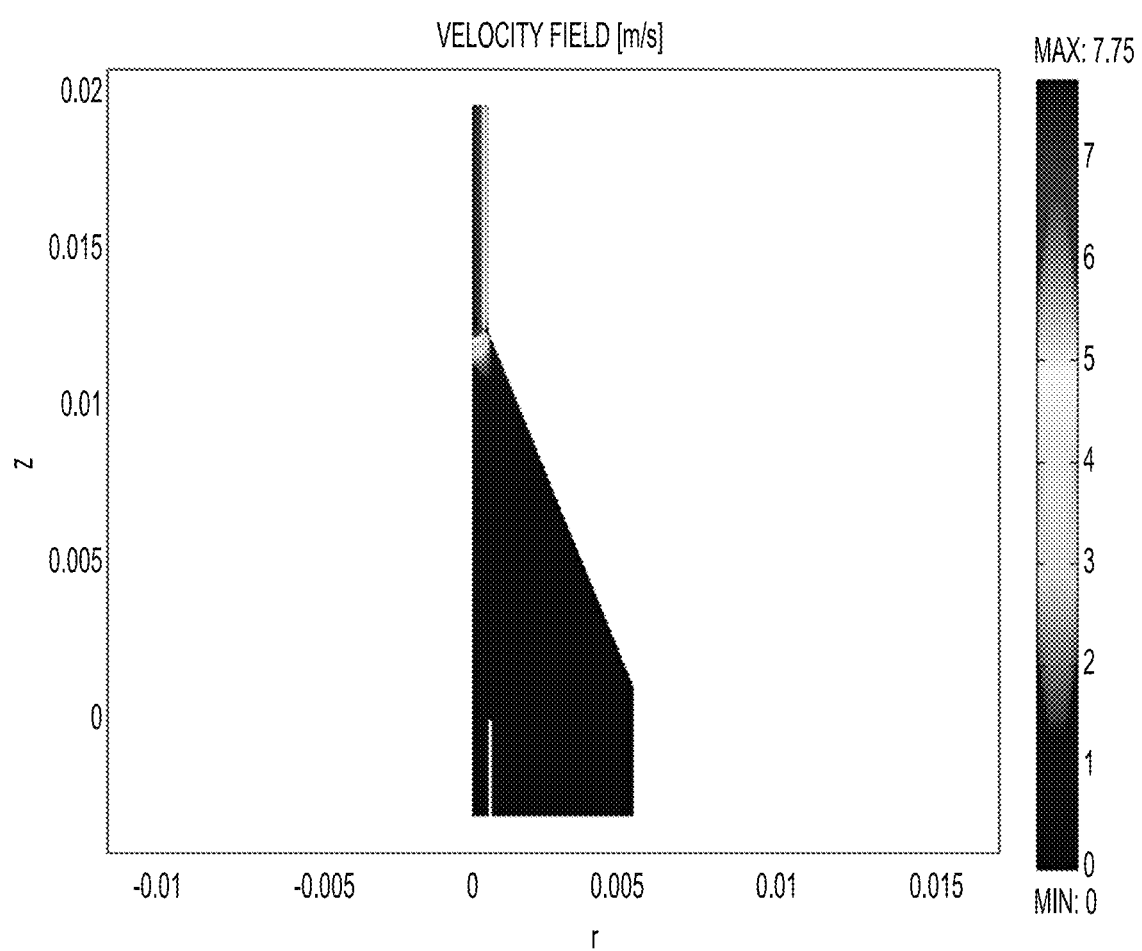
Figure 4C:
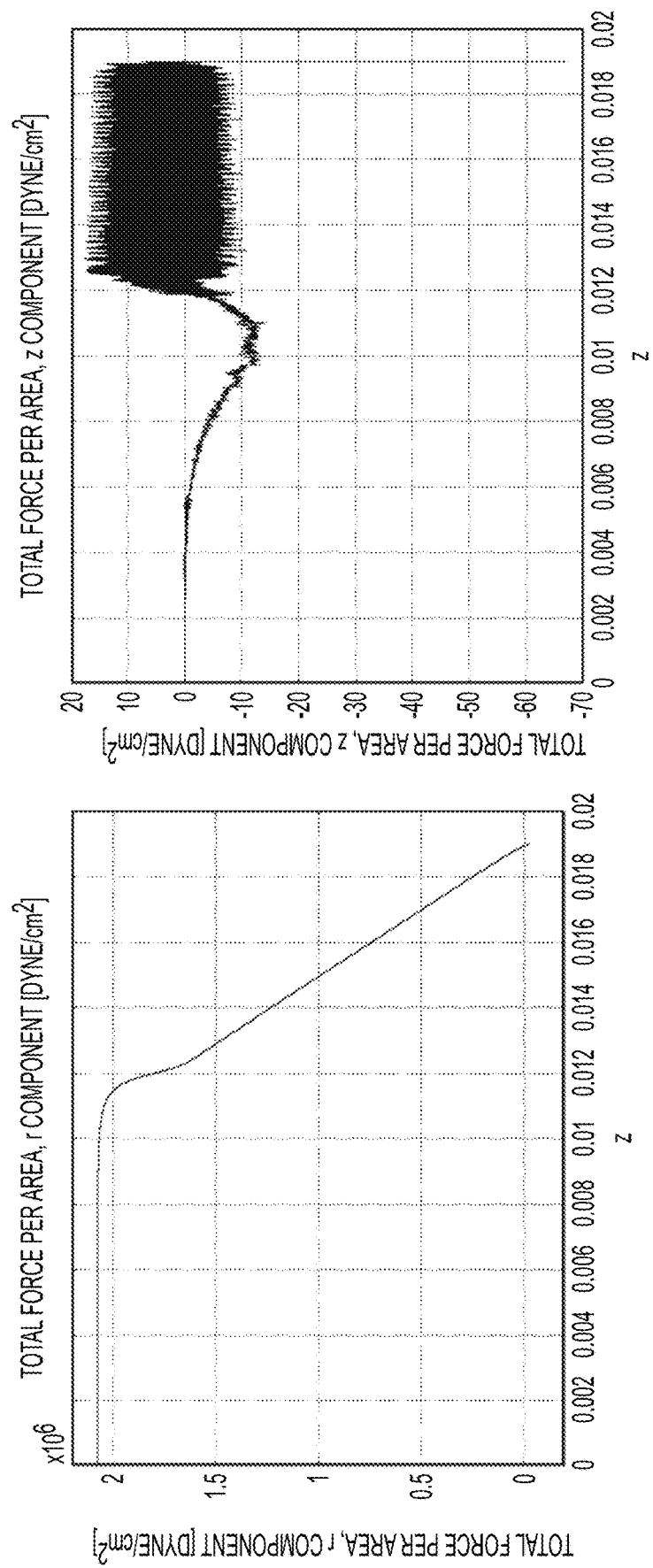
Figure 5A:
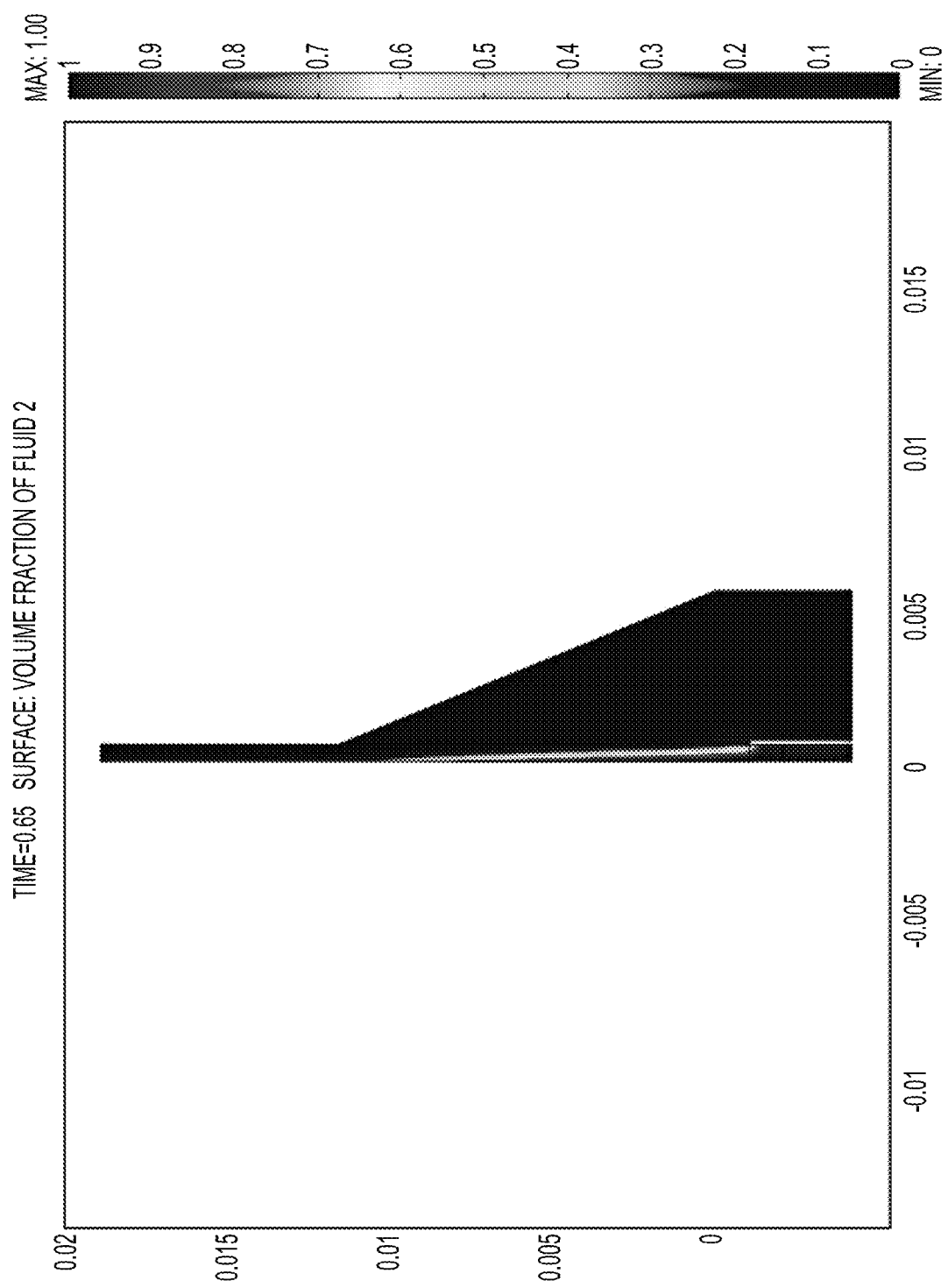
Figure 5B:
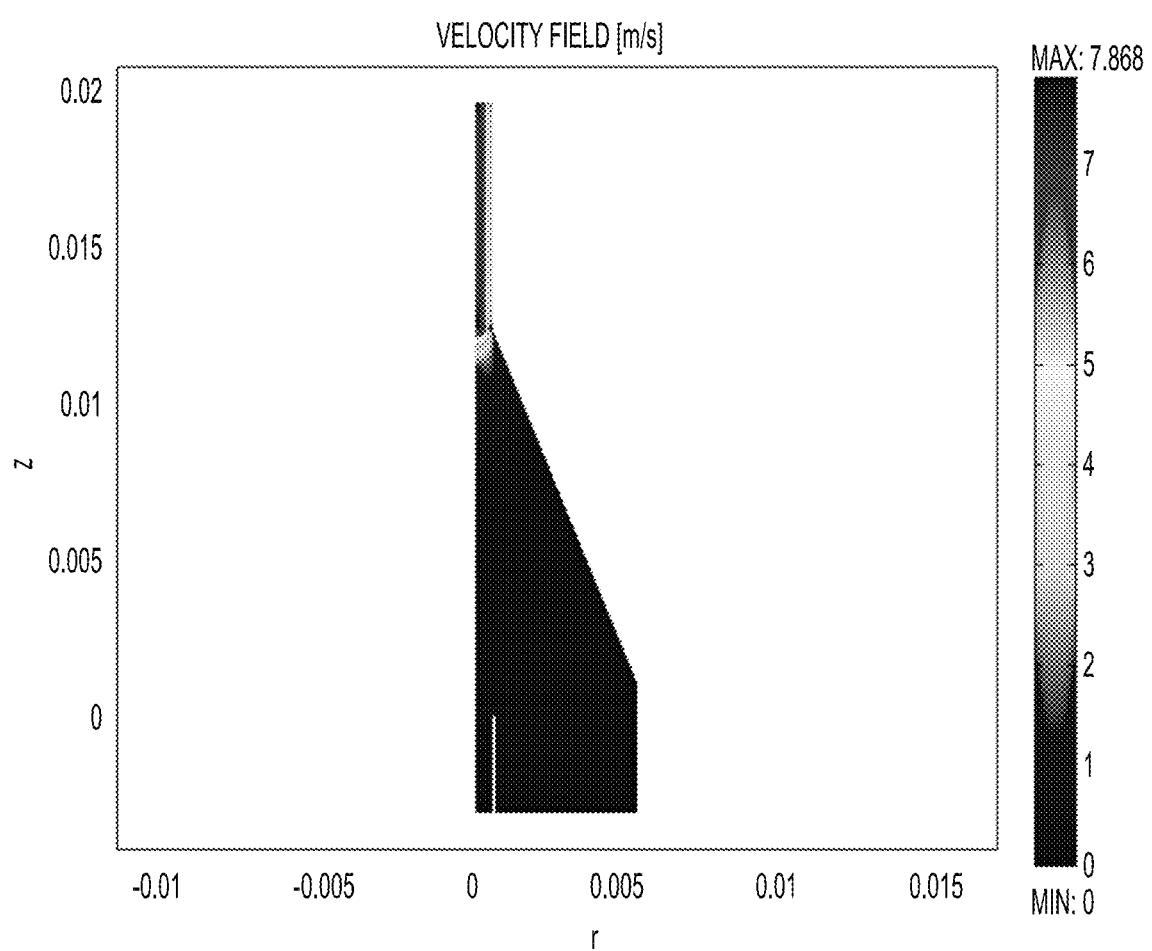
Figure 5C:
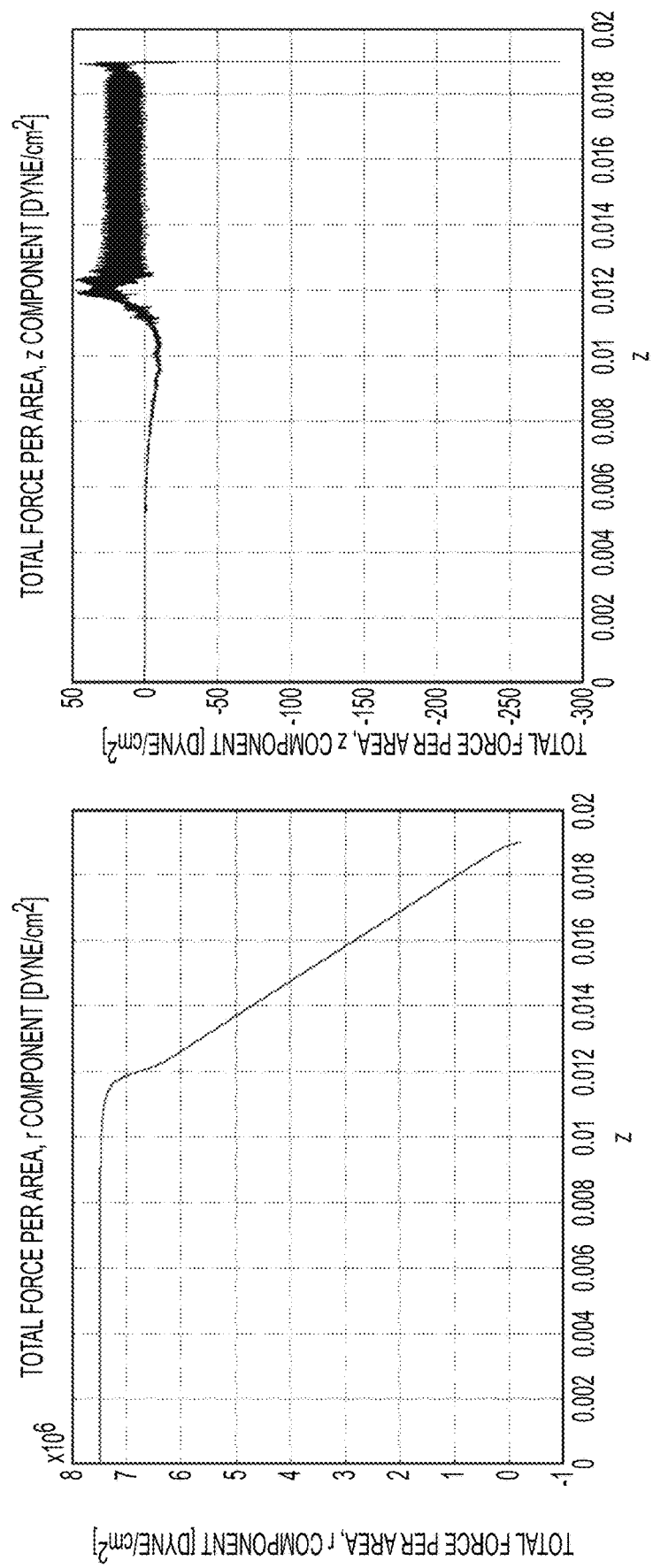
Figure 6A:
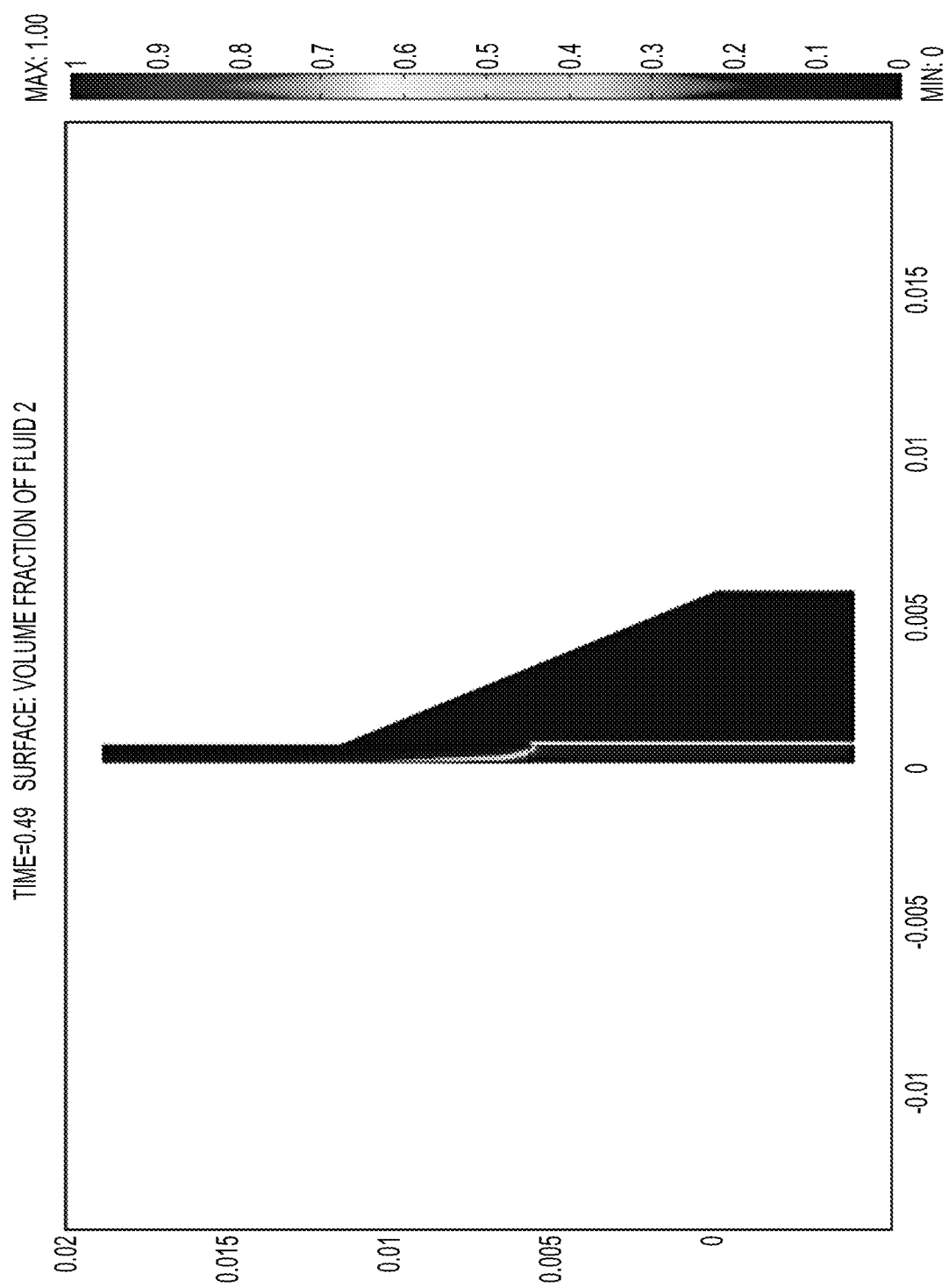
Figure 6B:
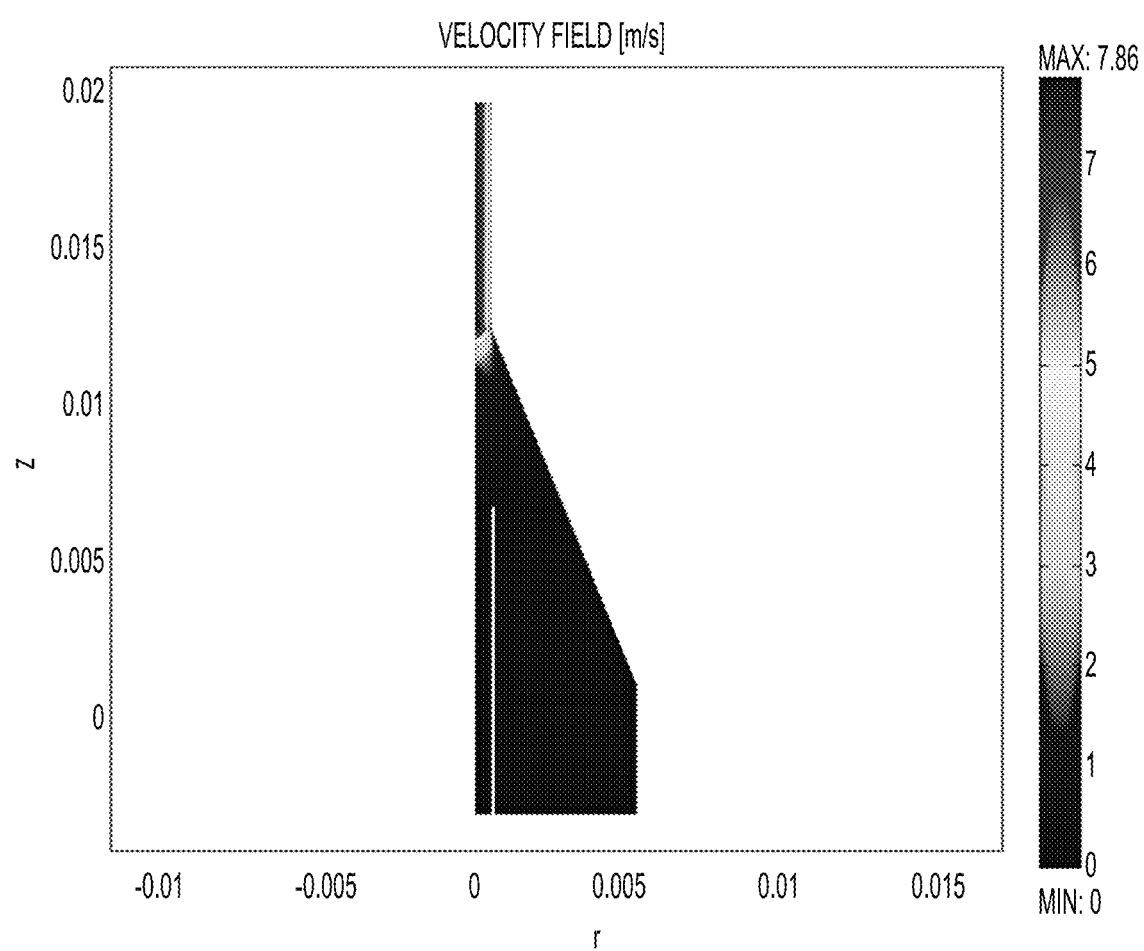
Figure 6C:
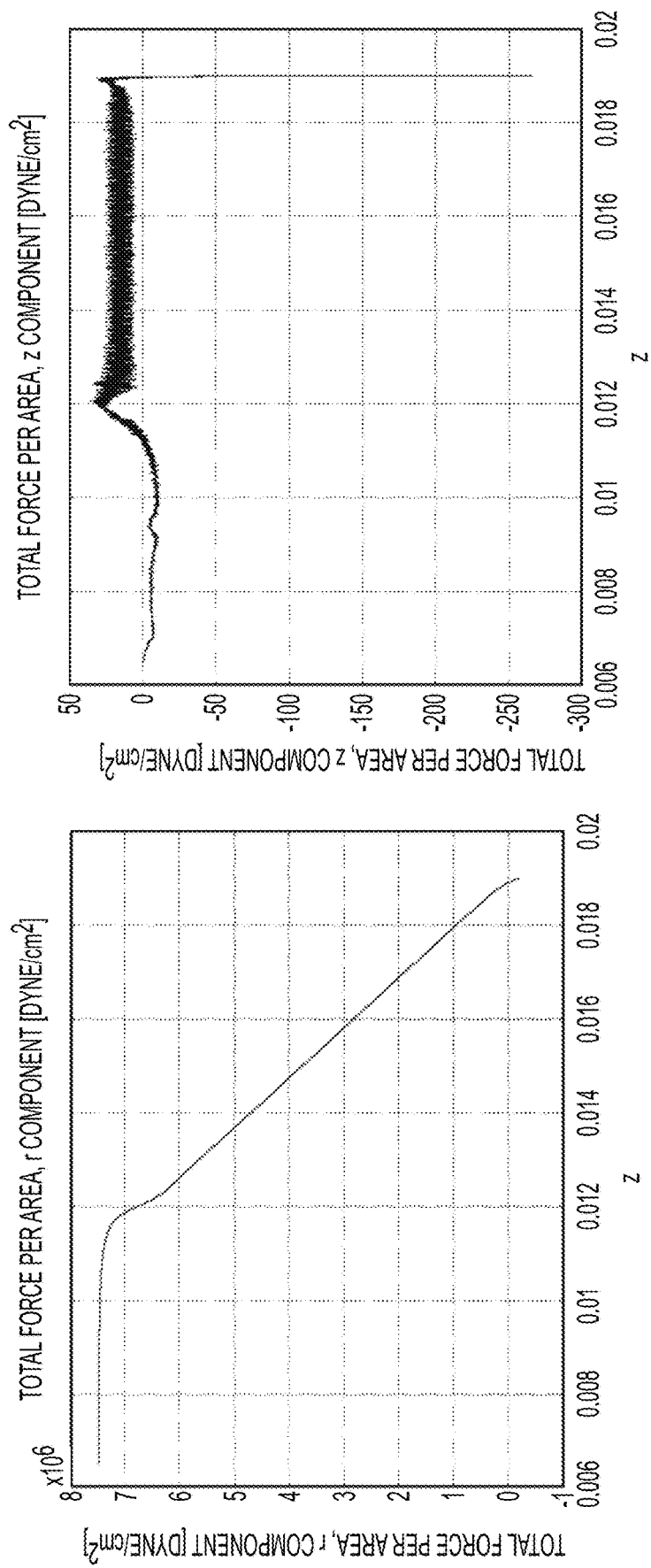
Figure 7B:
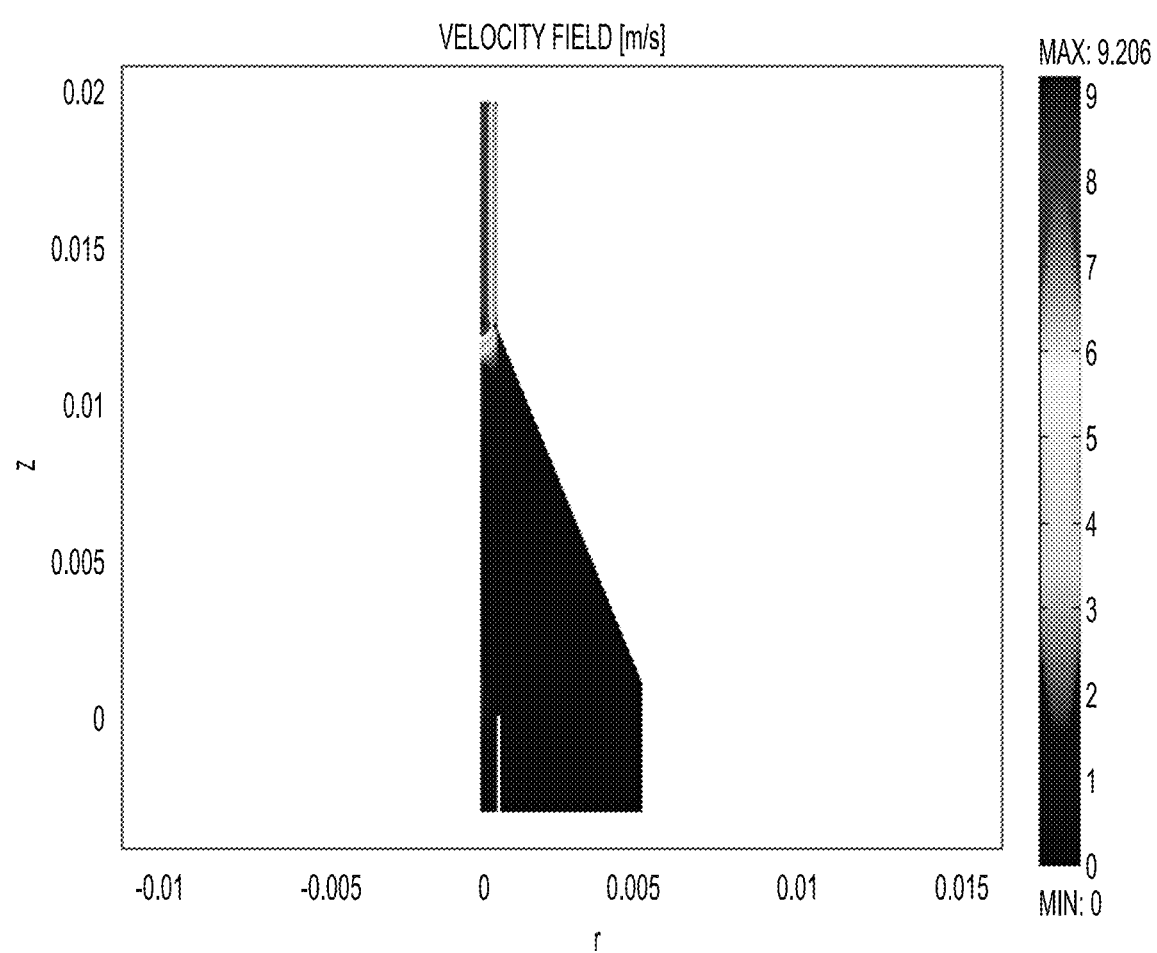
Figure 7C:
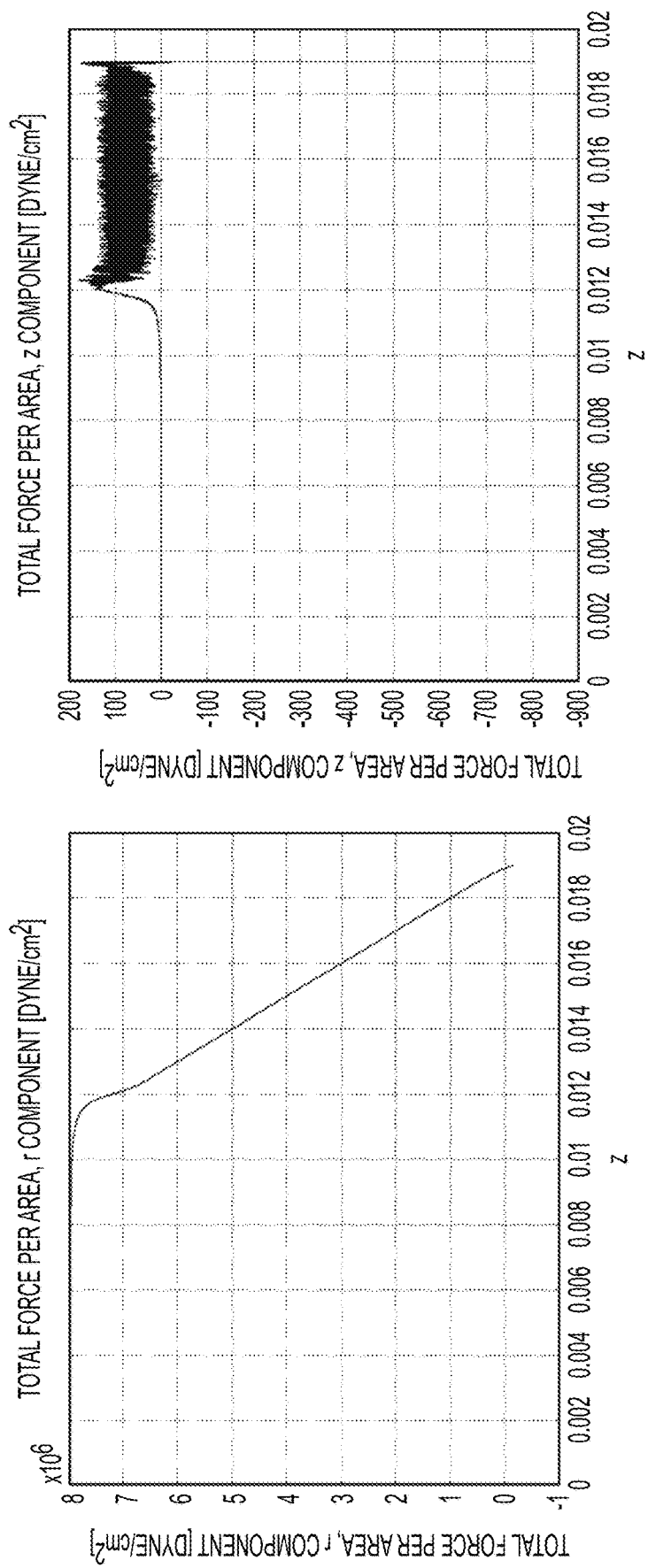
Figure 8B:
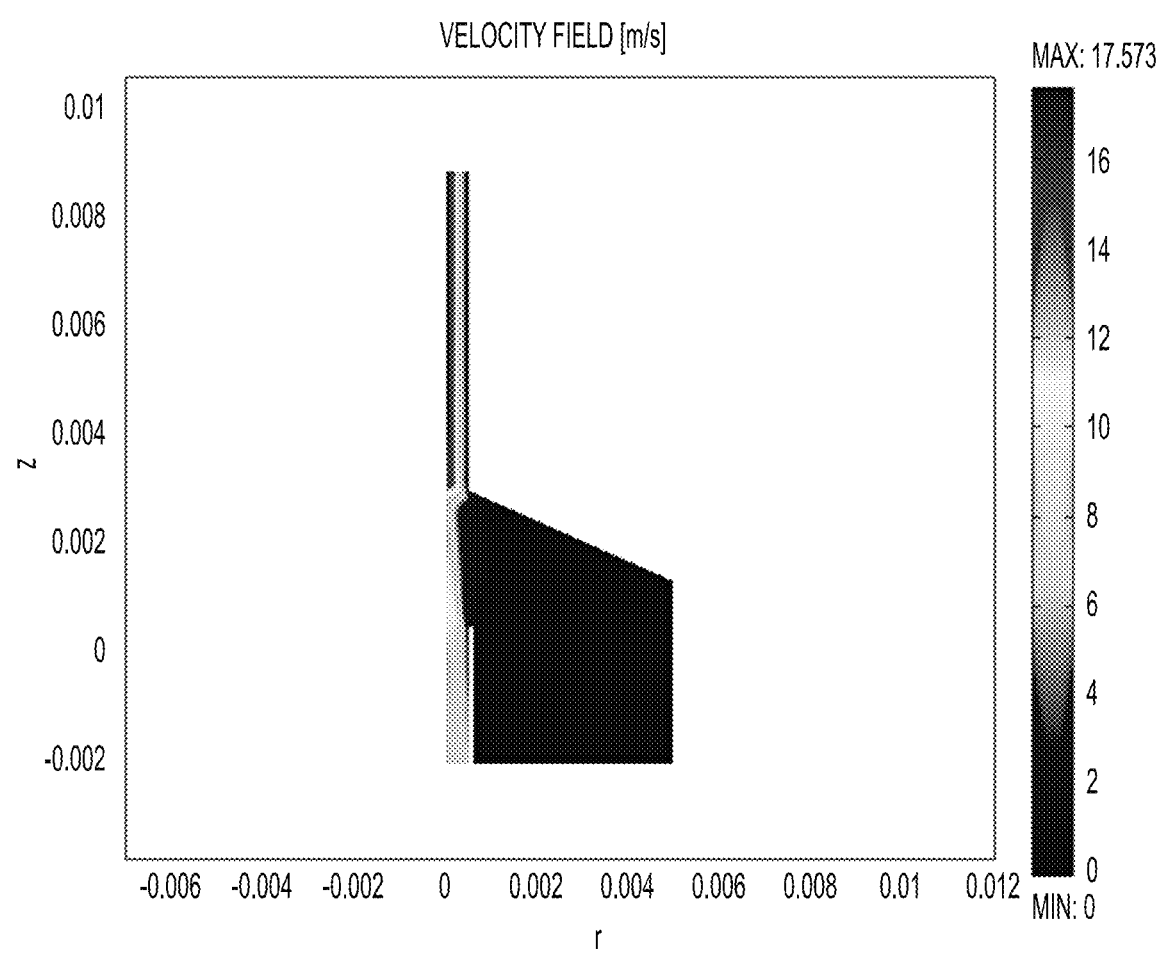
Figure 8C:
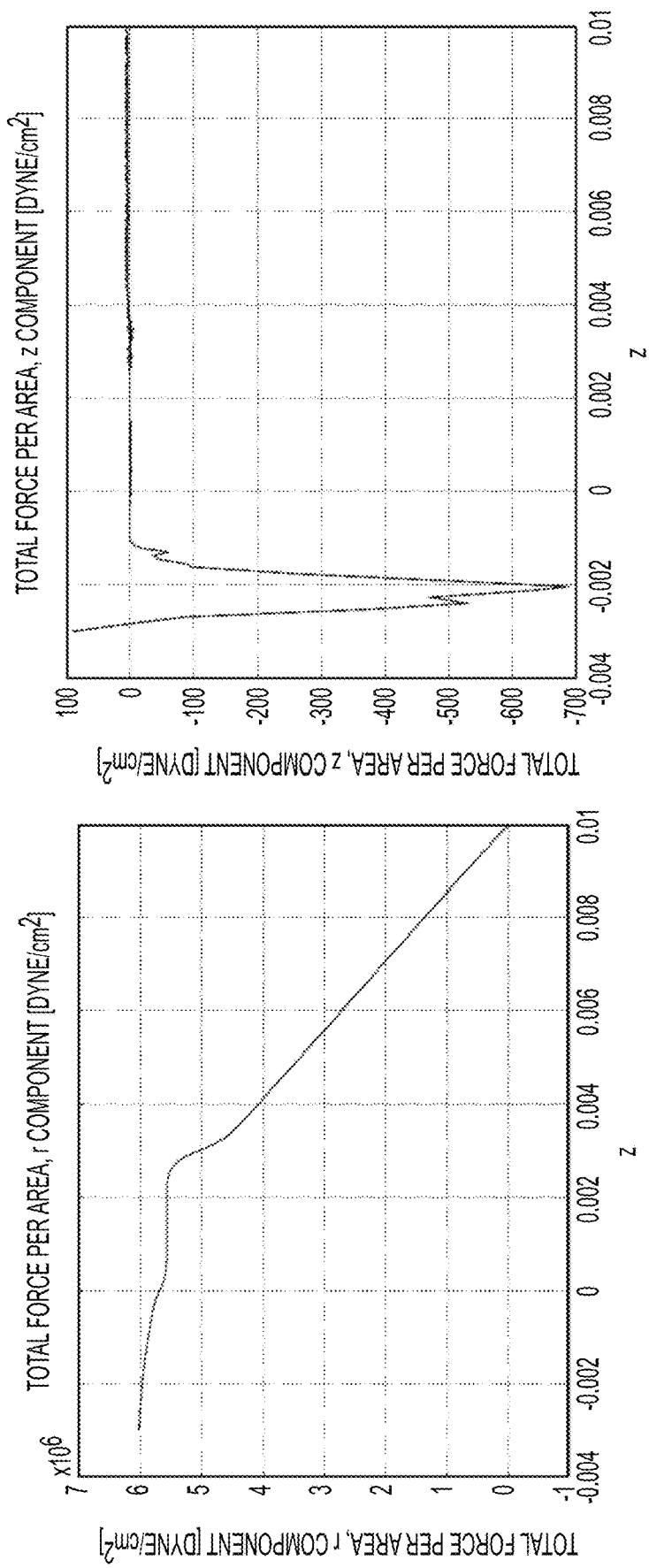
Figure 9A:
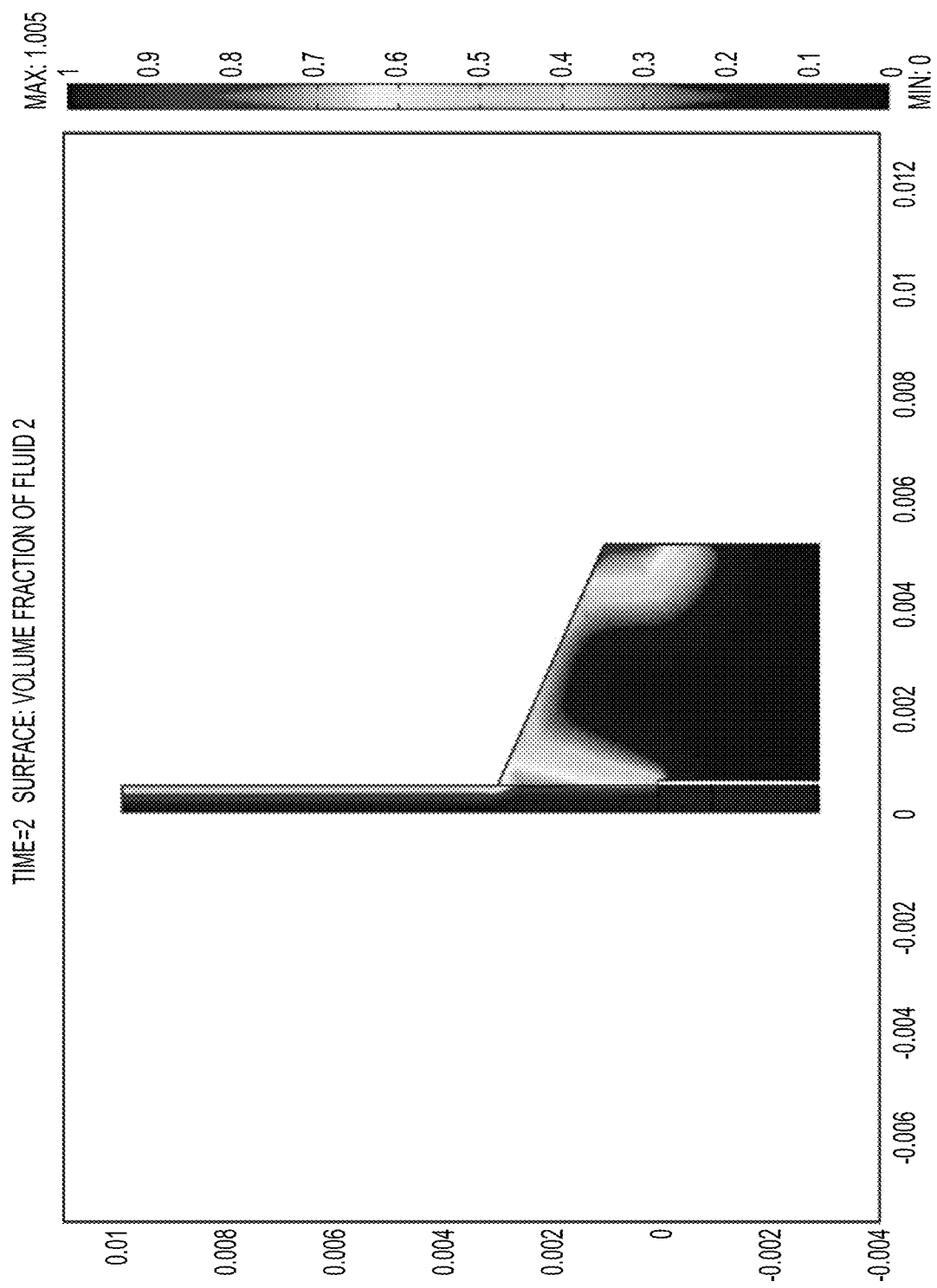
Figure 9B:
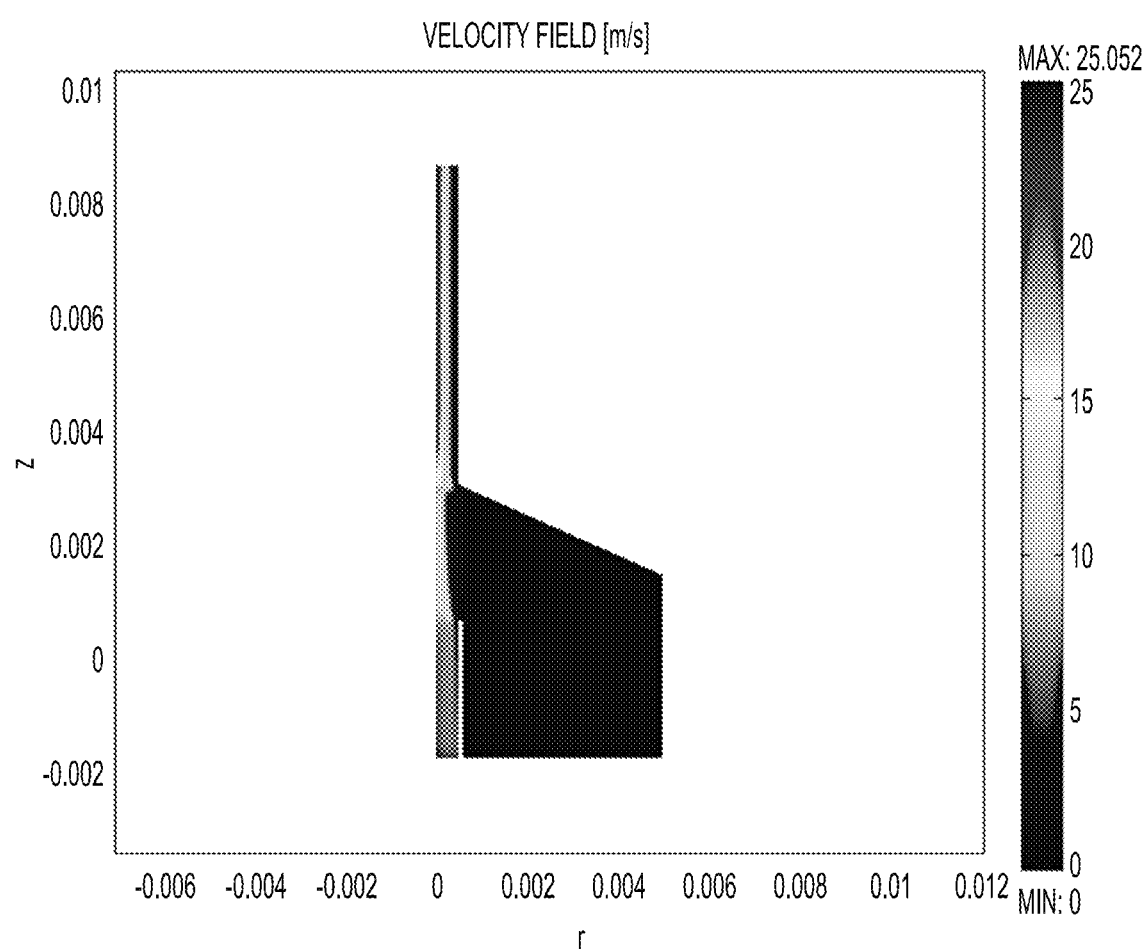
Figure 9C:
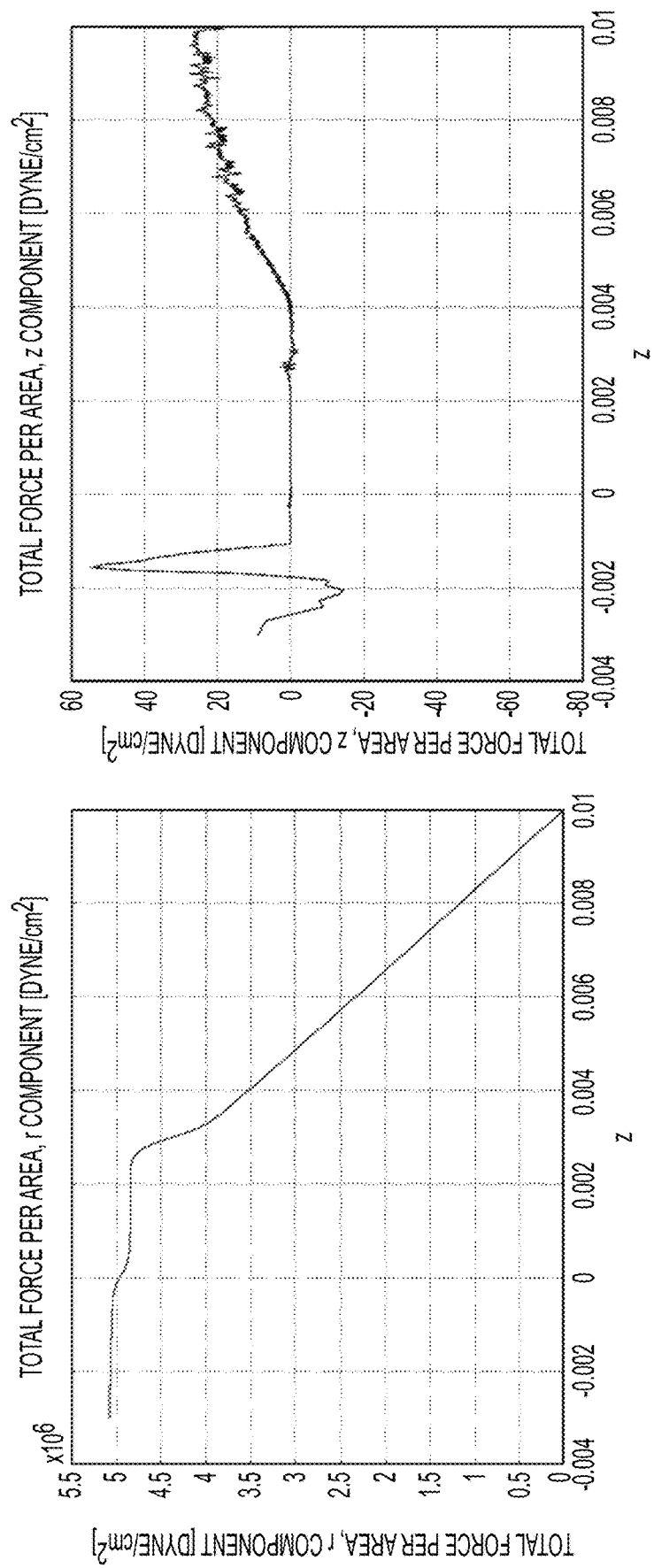
Figure 10A:
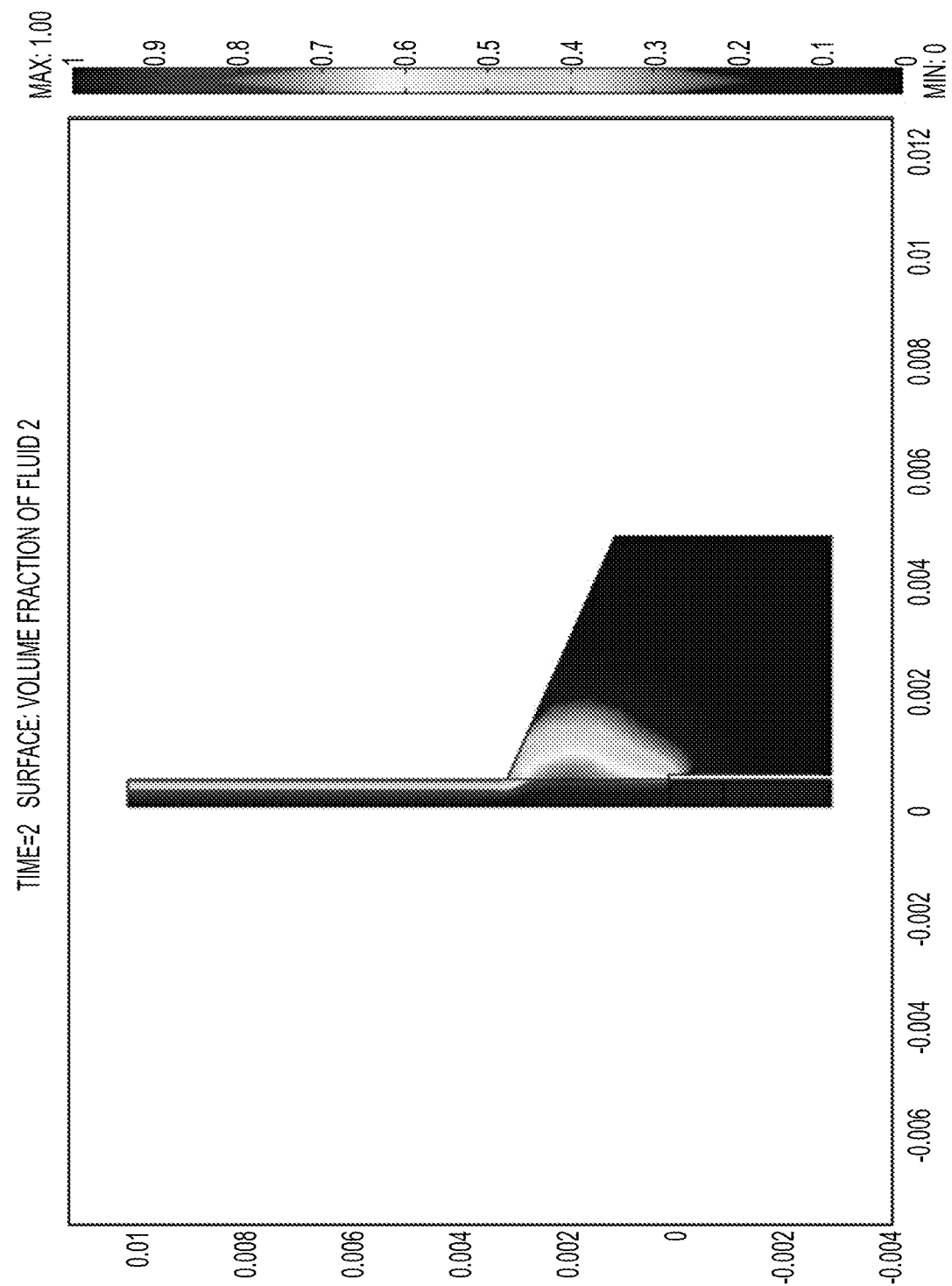
Figure 10B:
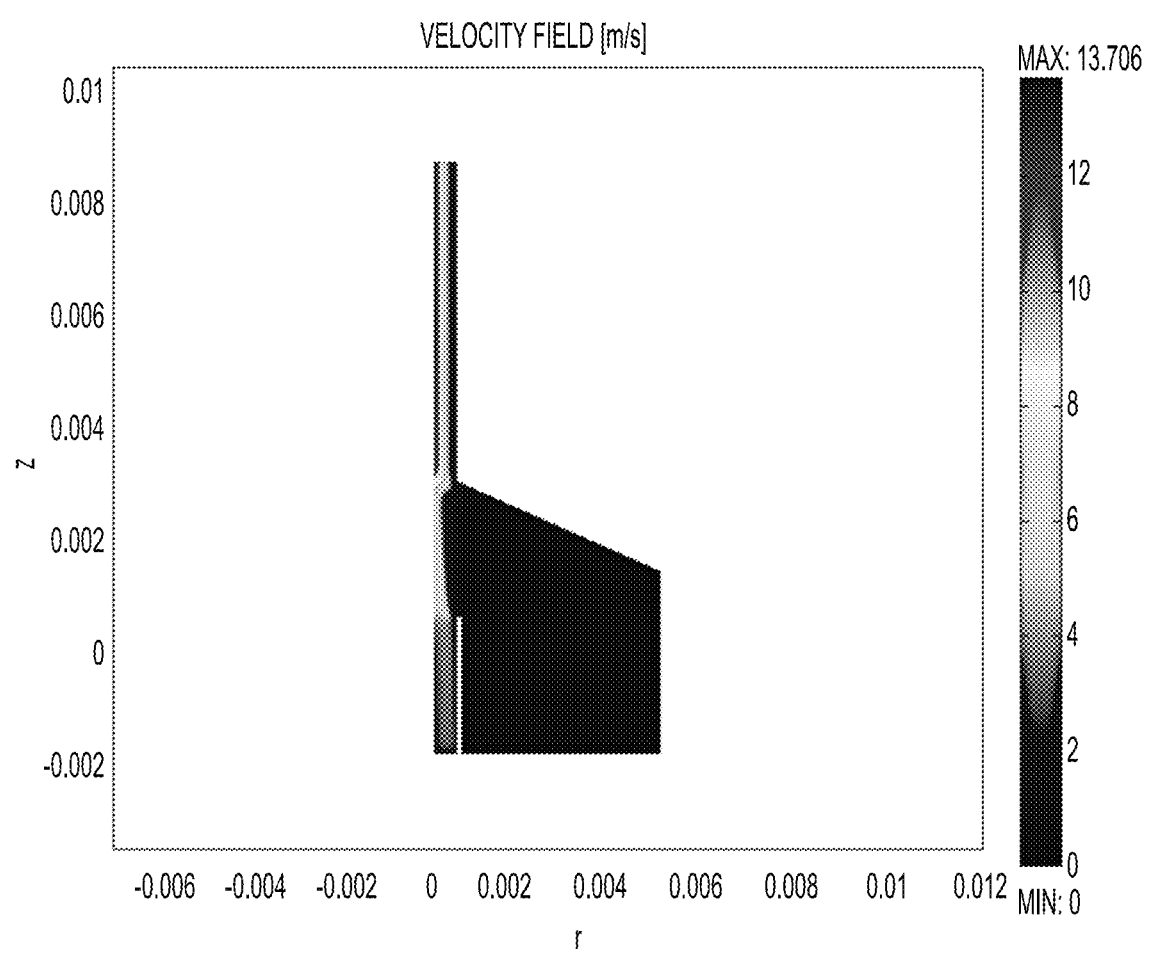
Figure 10C:
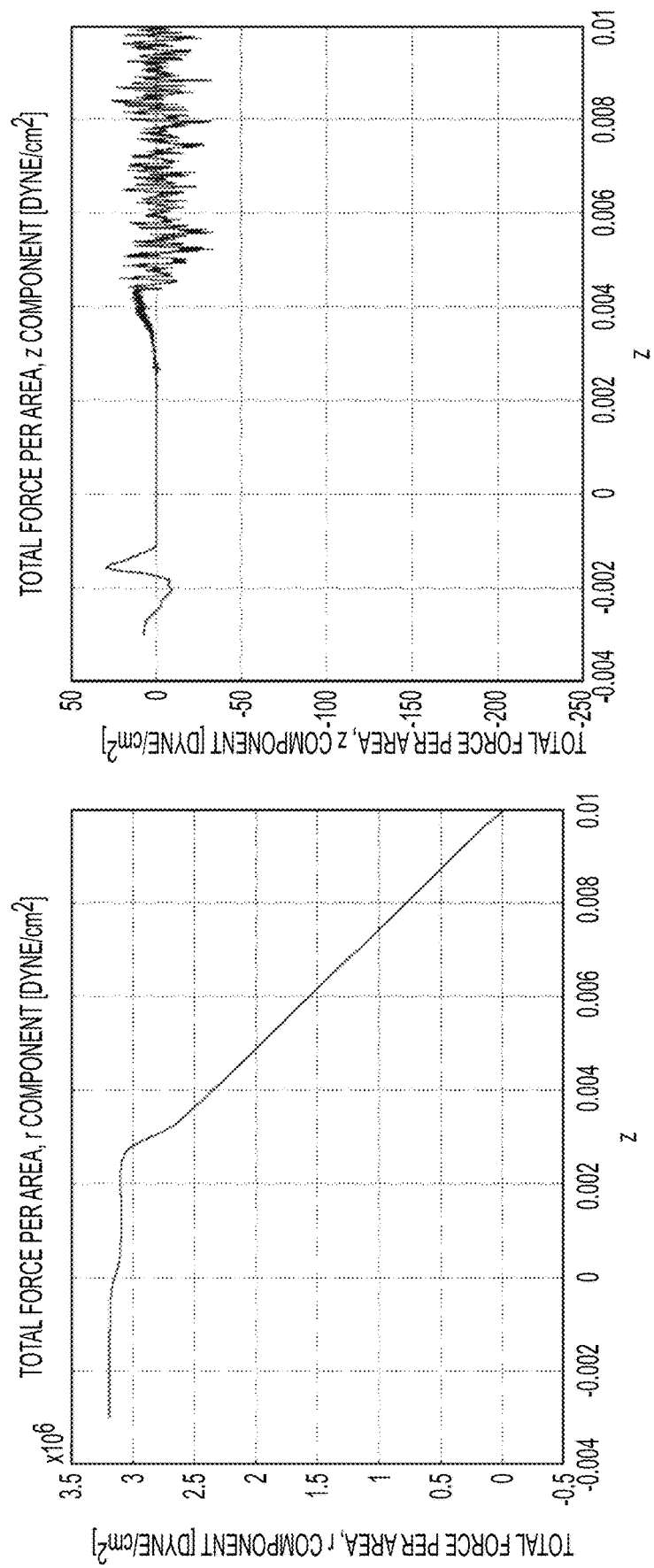
Figure 11A:
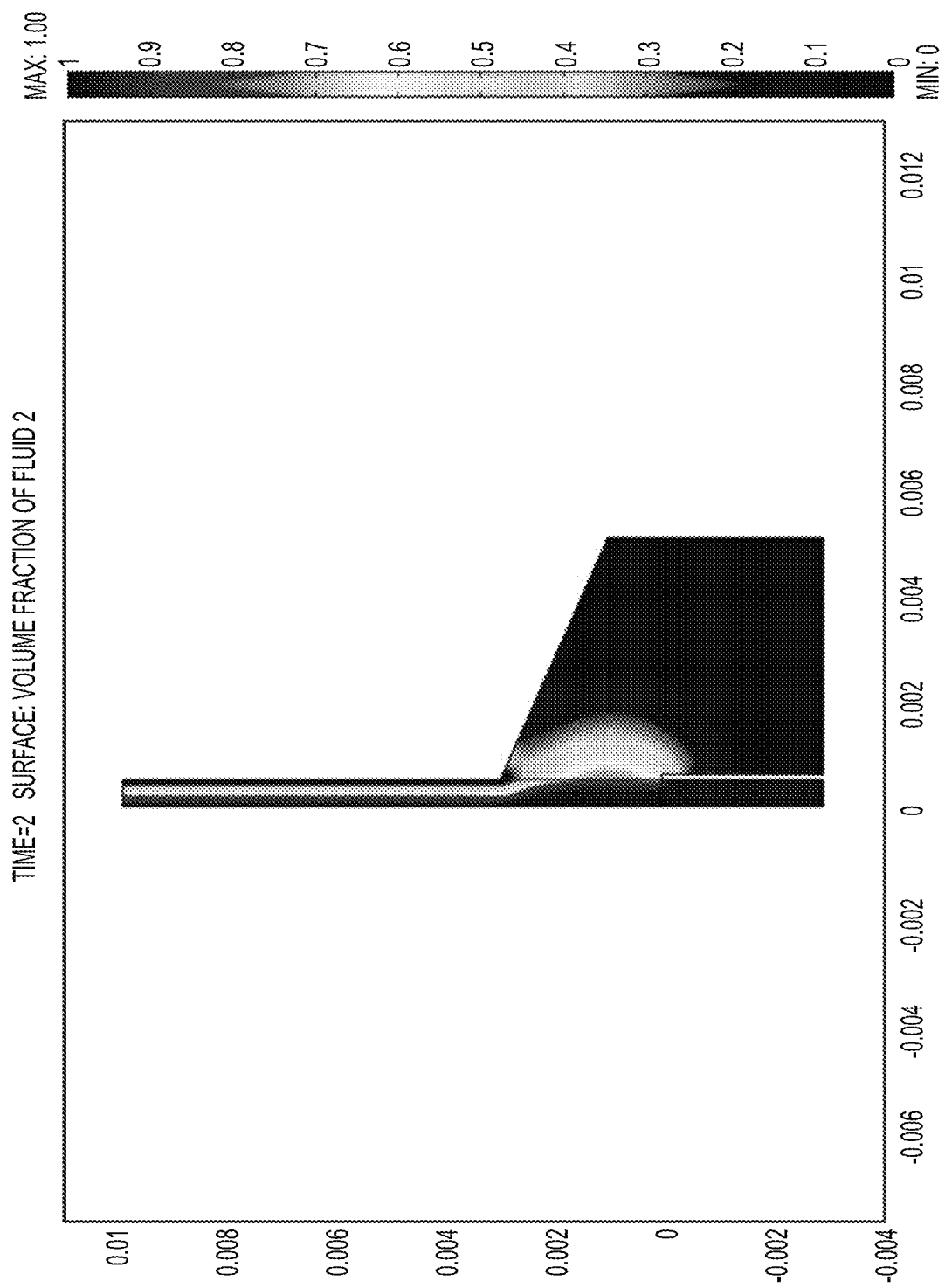
Figure 11B:
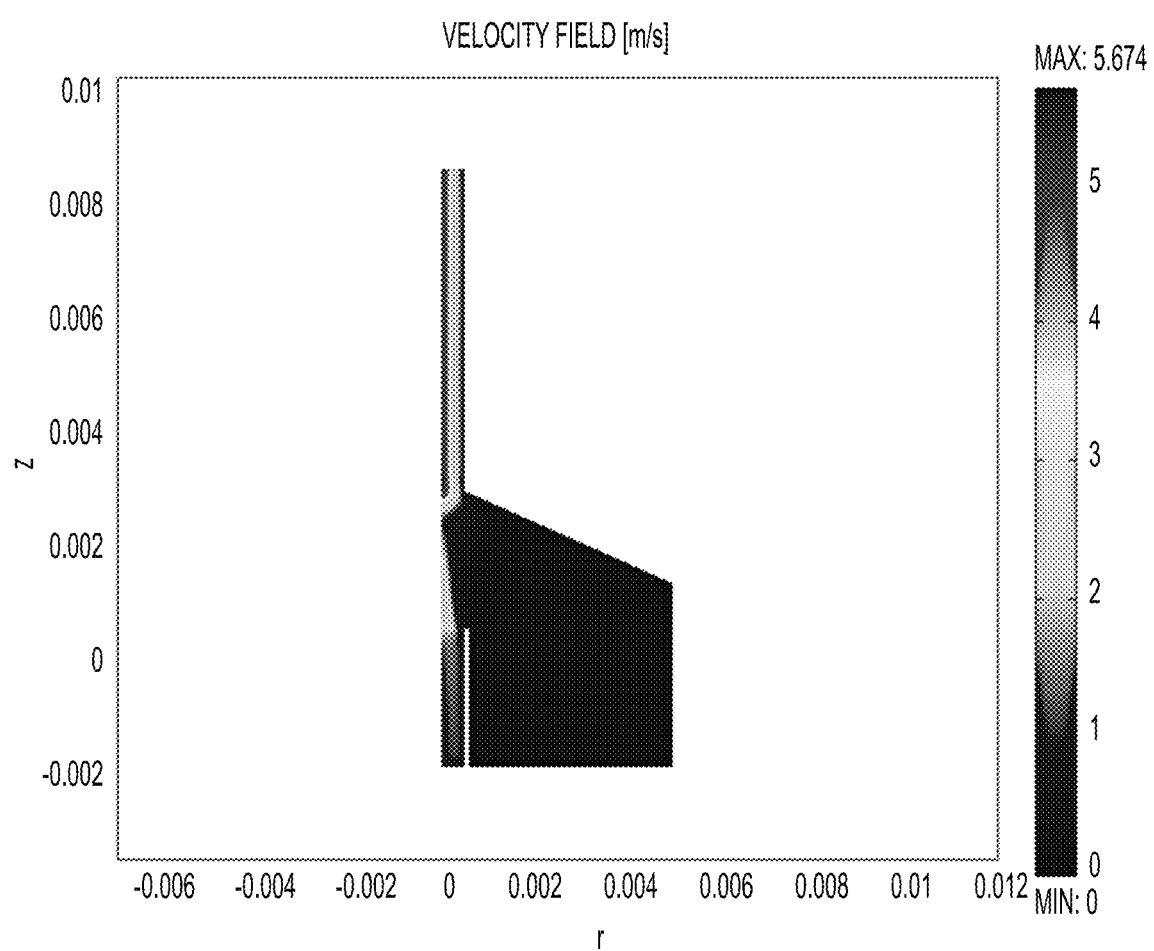
Figure 11C:
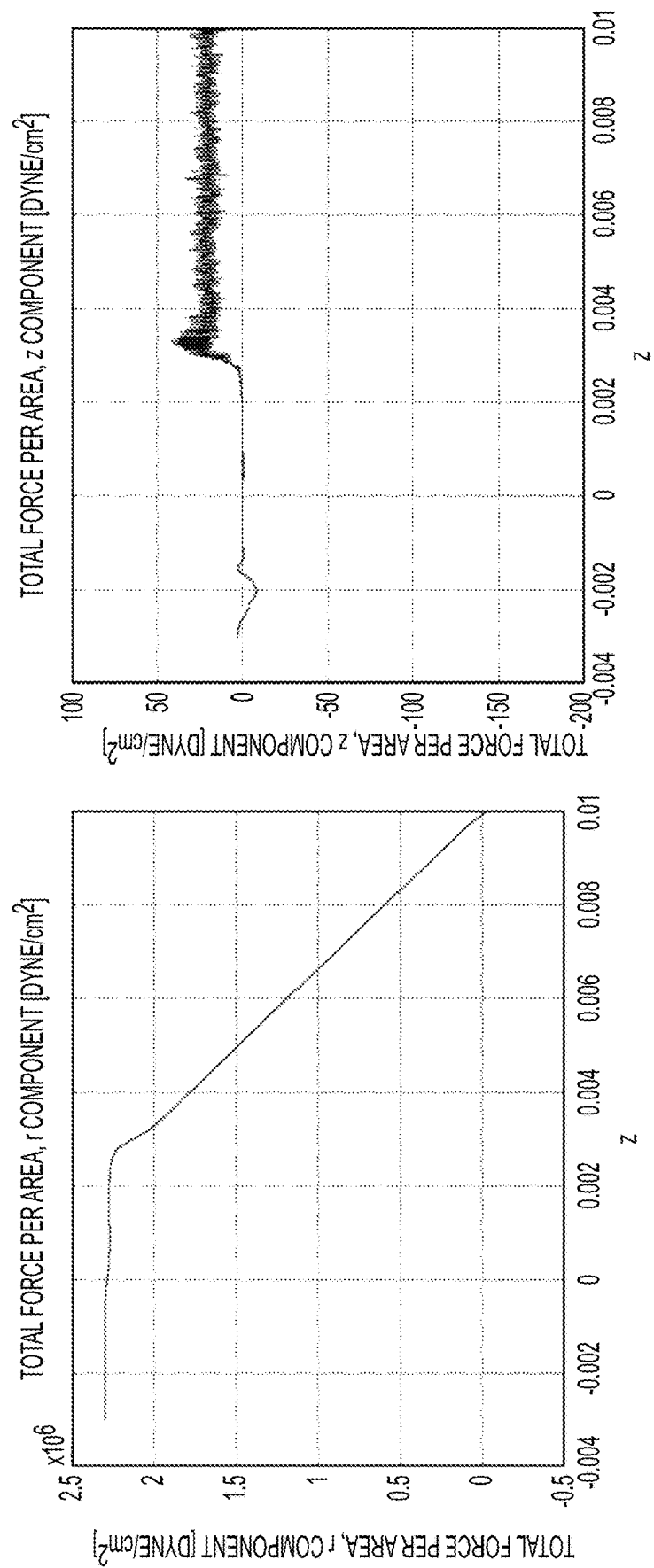

A 2D axisymmetric geometry has been used with two different focusing settings: "more focusing" and "less focusing" and different water injection points. The mesh has been created by imposing a maximum size of the element in the central axis (r=0) equal to $10^{-5}$ m (FIG. 1C).

Table 1 shows the values of the different experimental fluid dynamic parameters (viscosity of oil and water phases, velocity of oil and water phases, surface tension) and the geometry of the chamber (injection point for water phase in oil and type of focusing geometry) for each developed computational model. Table 1 also indicates whether the set of experimental parameters chosen for each model results in jetting or dripping of the water phase within the oil phase, as well as the maximum values of the total radial stress.

It was not possible to run the model with the true values of the water and oil velocities, since compilation timings would have been unacceptable and computer memory shortage would limit compilations. Therefore, we increased by $10^3$ the magnitude of the velocities. Results (especially regarding values of shear stresses) are thus not representative of the real values in the experimental system that is described further below, but are meaningful for comparison between different conditions.

TABLE 1

| model # | viscosity oil η oil (Pa * s) | viscosity water η water (Pa * s) | max velocity oil vmax oil (m/s) | max velocity water vmax water (m/s) | surface tension σ (N/m) | injection point standard/ closer | focusing geometry less/ more | jet or dripping J/D | max total stress Tr max (dyn/cm2) |
|---|---|---|---|---|---|---|---|---|---|
| 1 | 0.34 | 0.01 | $5 \times 10^{-2}$ | $1 \times 10^{-2}$ | 0.005 | std | more | J | $2 * 10^6$ |
| 2 | 0.34 | 0.01 | $5 \times 10^{-2}$ | $1 \times 10^{-2}$ | 0.005 | std | less | D | $2 * 10^6$ |
| 3 | 0.34 | 0.01 | $5 \times 10^{-2}$ | $5 \times 10^{-2}$ | 0.005 | std | less | J | $2 * 10^6$ |
| 4 | 1.301 | 0.01 | $5 \times 10^{-2}$ | $5 \times 10^{-2}$ | 0.005 | std | less | J | $7.5 * 10^6$ |
| 5 | 1.301 | 0.01 | $5 \times 10^{-2}$ | $5 \times 10^{-2}$ | 0.005 | closer | less | J | $7.5 * 10^6$ |
| 6 | 1.301 | 0.01 | $5 \times 10^{-2}$ | $50 \times 10^{-2}$ | 0.005 | std | less | J | $8 * 10^6$ |
| 7 | 1.301 | 0.1 | $1 \times 10^{-2}$ | $700 \times 10^{-2}$ | 0.005 | std | more | J | $6 * 10^6$ |
| 8 | 1.301 | 0.01 | $1 \times 10^{-2}$ | $700 \times 10^{-2}$ | 0.005 | std | more | J | $5 * 10^6$ |
| 9 | 1.301 | 0.01 | $1 \times 10^{-2}$ | $350 \times 10^{-2}$ | 0.005 | std | more | J | $3.5 * 10^6$ |
| 10 | 1.301 | 0.01 | $1 \times 10^{-2}$ | $125 \times 10^{-2}$ | 0.005 | std | more | J | $2.5 * 10^6$ |

The results are shown in FIGS. 2A-11C.

Example 2: Flow Chamber Design and Realization

Flow chambers (with "more focusing" and "less focusing" geometry, different diameters of the co-axial chambers) have been designed and manufactured to experimentally test the effects of different geometries and different hydrodynamic parameters on islet encapsulation.

The flow chambers are characterized by a flow focusing region ("more" and "less" focusing) and a narrow straight channel down-stream.

Figure 12A:
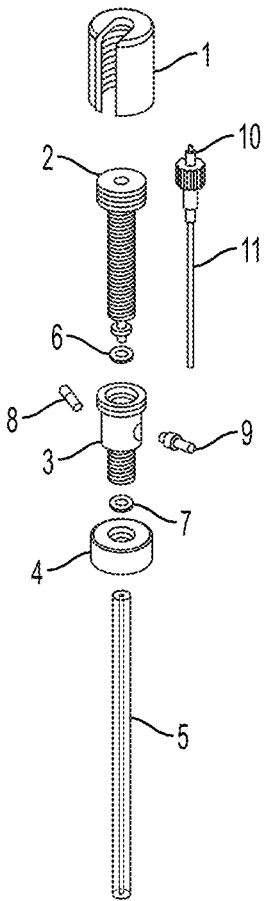
FIG. 12A and FIG. 12B: Flow chamber design characterized by a chamber with a flow-focusing region (10 to 1 narrowing), a coaxial injector system and a narrow coaxial outflow channel.

The water phase containing coating solutions and cell clusters is injected in the center channel by a catheter (FIG. 12A: 11, "more focusing" geometry) that is connected to the injection tube and pump through a male Luer integral lock ring (FIG. 12A: 10), and is focused in the main chamber (FIG. 12A: 3) into the narrow channel downstream (FIG. 12A: 4, 5, 7) from the main chamber by the co-flowing external stream of oil that is injected within the chamber through a lateral port (FIG. 12A: 9). Entrapped air is eliminated through a lateral port (FIG. 12A: 8) upstream of the oil injection port. The water injection catheter (FIG. 12A: 11) is secured in its optimal position through a locking cap (FIG. 12A: 1) for the inner chamber (FIG. 12A: 2).

Oil phase flow is maintained by a peristaltic pump while water phase flow is maintained by a 2 ml-syringe pump.

Figure 12B:
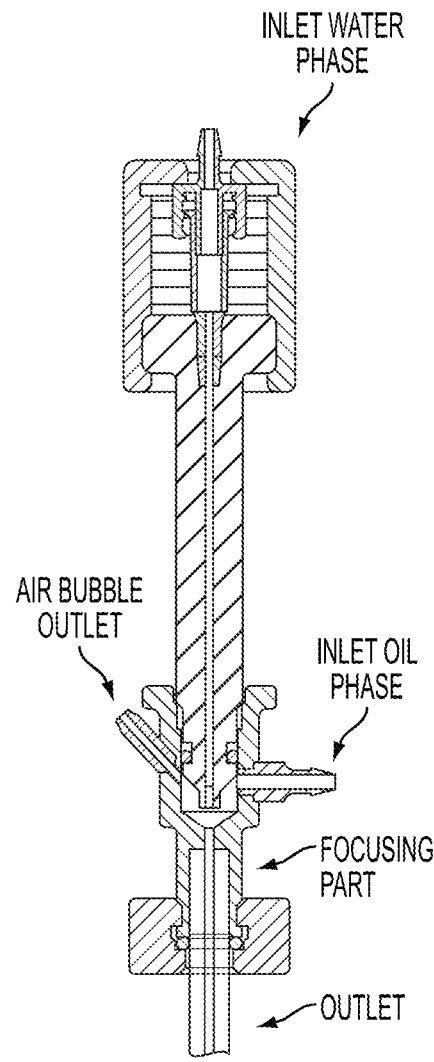

Both the "more focusing" and the "less focusing" flow chambers have been tested, with more promising results for the "more focusing" flow chamber (see design of exemplary flow chamber: FIGS. 12A and 12B).

Different injection positions of the water phase inside the oil phase have also been tested and the optimal positions discovered to be: (1) the standard one in which the tip of the water injection needle co-localizes with the base of the focusing region of the device, and (2) a position in which the tip of the water injection needle is 0.5 mm upstream of the focusing region (FIGS. 12A and 12B).

We performed optimization experiments using islet-like beads (red polystyrene) that have a size similar to islets (50-300 μm).

We performed experiments to determine:
optimal ratio of water versus oil velocities;
optimal islet-like bead concentration in the water phase;
optimal set-up to allow injection of the water phase within the oil phase without having backflow of the oil phase into the water injection needle;
optimal composition of the water phase to prevent cell cluster coalescence;
optimal composition and pH of the water phase and oil phase to allow gelation of coating solution downstream jet break-up;
optimal method for purifying PEG coated and non-coated beads and PEG droplets from PPG oil phase at the outflow; and
optimal method for purifying coated beads from empty PEG beads.

The results are discussed below.

Example 3: PEG Functionalization and Gelation

PEG gelation is achieved by cross-linking of PEG 8-arm 10 kDa, which has been functionalized with divinyl sulfone (PEG-dVS) or with maleimide (PEG-MAL), by addition of dithiothreitol (DTT) and by adjusting the pH from less than 6.5 to 7.4 using triethanolamine (TEA). Gelation of alternative non PEG-based hydrogels (for example, VLVG) is achieved by cross-linking of monomers that have been functionalized with divinyl sulfone (dVS) or with maleimide (MAL) by addition of dithiothreitol (DTT), and by adjusting the pH from less than 6.5 to 7.4 using triethanolamine (TEA).

Figure 13:
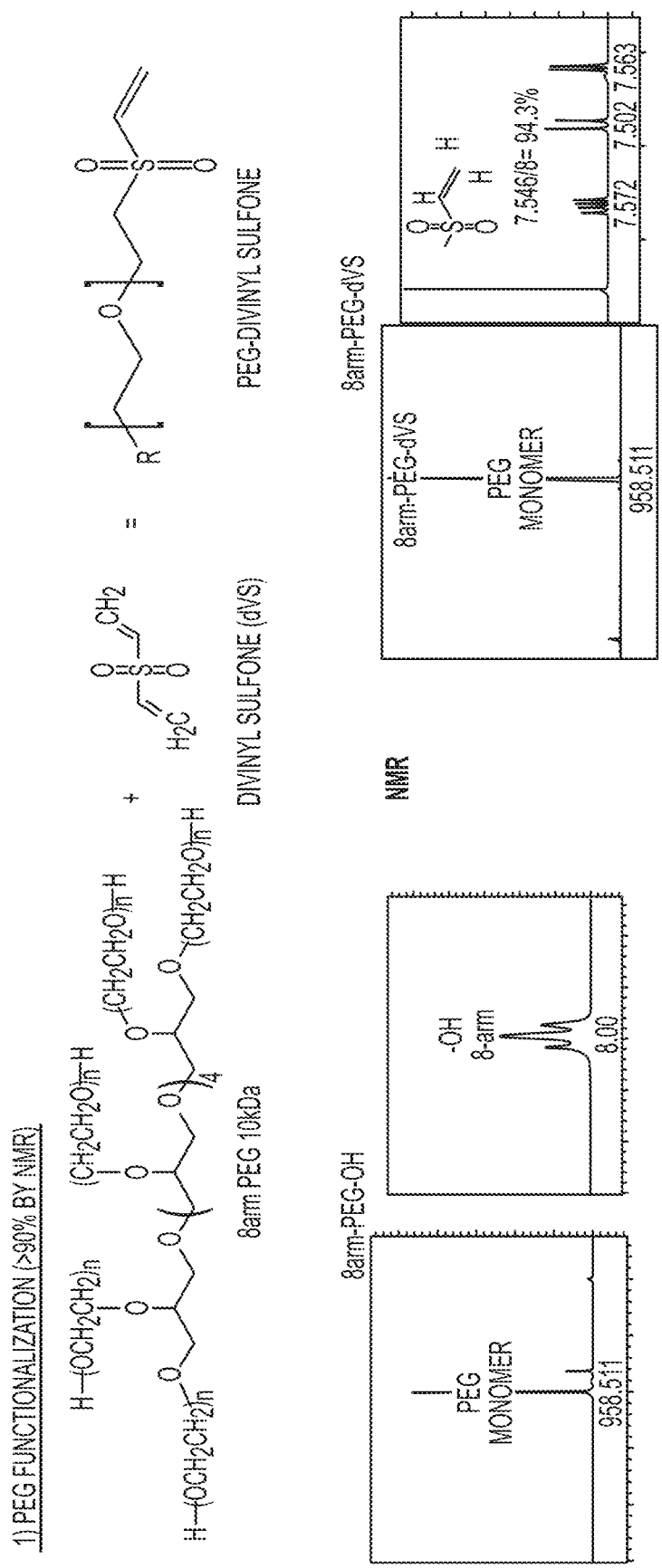
FIG. 13: Schematic showing PEG functionalization with dVS (greater than 90%) by Michael type addition of dVS in the presence of NaH.
Figure 15A:
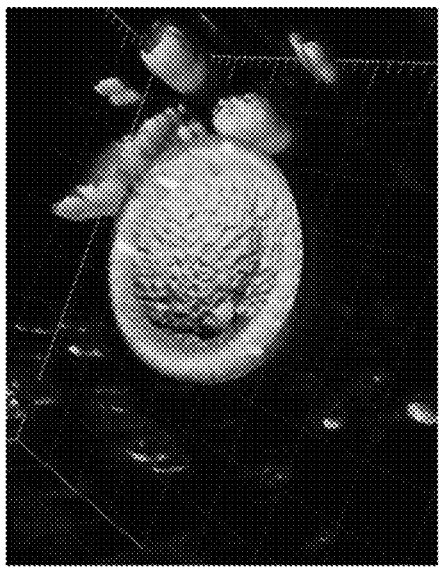
FIG. 15A, FIG. 15B, FIG. 15C, and FIG. 15D: Confocal images of FITC-PEG coated beads. Left: orthogonal projection of a z-scan of the entire coated bead. Right: 3D reconstruction of the z-scan series, sectioned in the midplane.
Figure 15B:
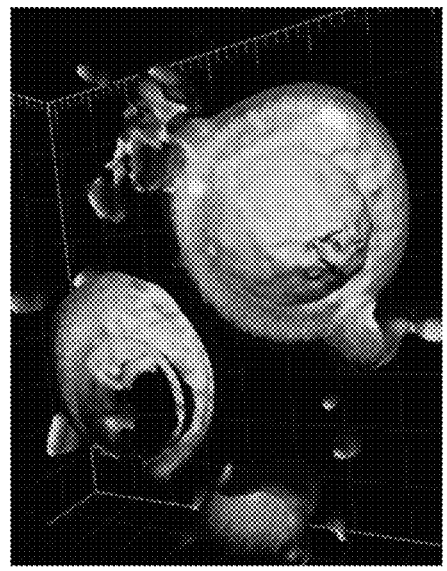
Figure 15C:
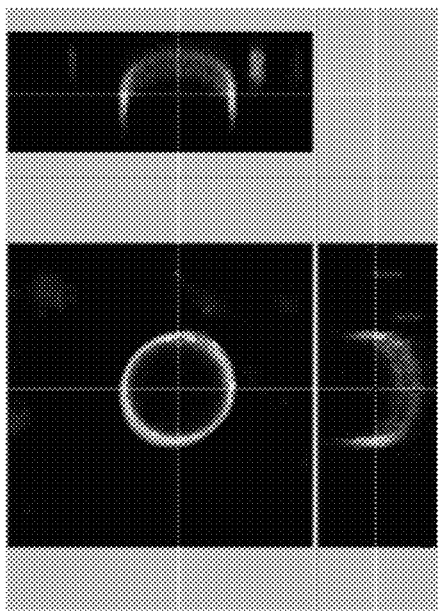
Figure 15D:
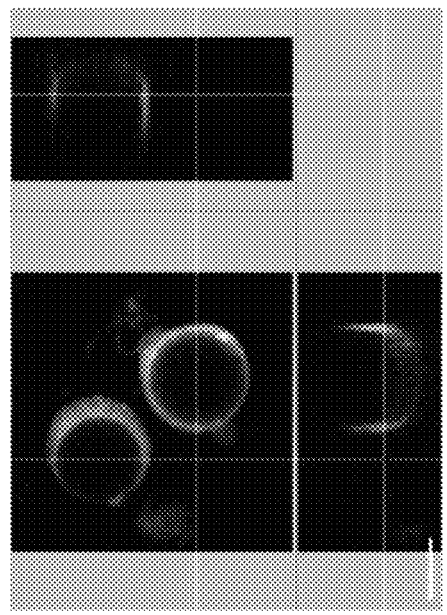
Figure 16C:
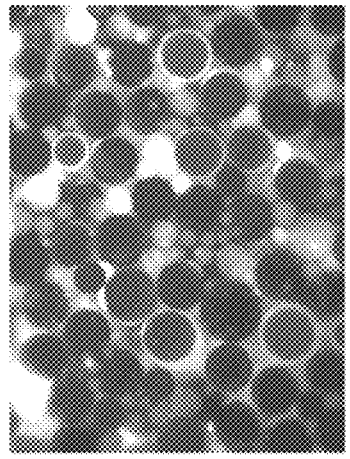
FIG. 16A, FIG. 16B, FIG. 16C, FIG. 16D, FIG. 16E, and FIG. 16F: Fluorescence microscope images of coated bead morphology, showing different outcomes achieved by varying experimental conditions. FITC-PEG-dVS has been added to the water phase at 1% concentration to fluorescently label the coating.
Figure 16F:
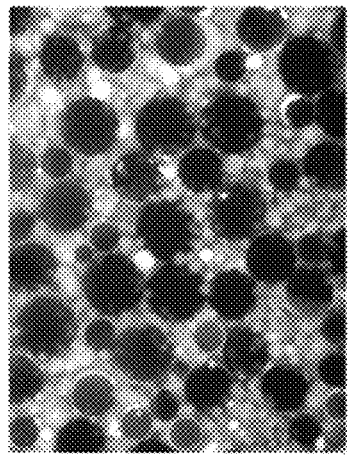
Figure 16B:
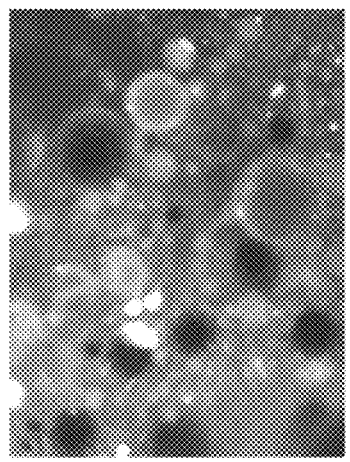
Figure 16E:
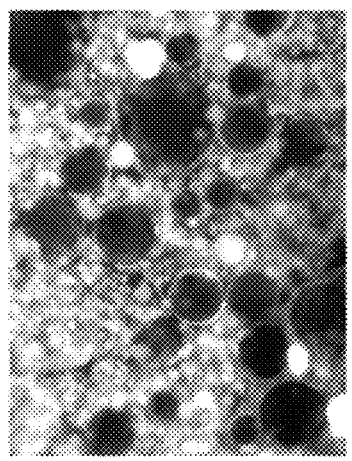
Figure 16A:
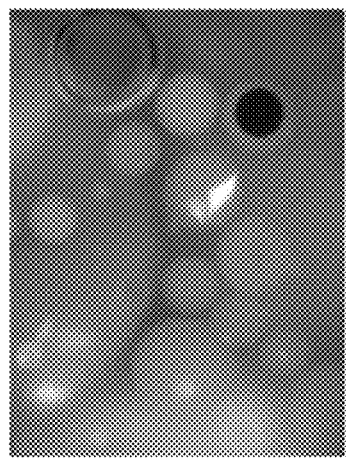
Figure 16D:
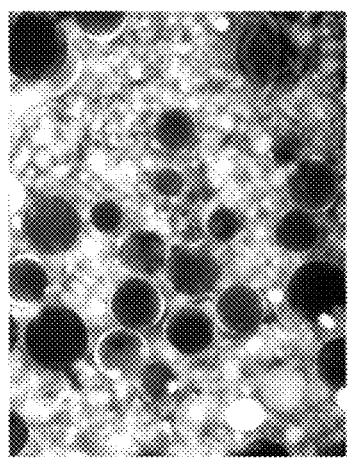

A schematic on PEG functionalization with dVS (greater than 90%) by Michael type addition of dVS in the presence of NaH (1) is shown in FIG. 13.

In order to be able to image PEG gel by fluorescence microscopy, we labeled PEG-dVS with fluoresceinamine by Michael type addition in a sodium carbonate buffer (ibis) (FIG. 14).

Example 4: Hydrodynamic and Experimental Parameters

In the flow chambers that we designed, we have optimized jet formation and break-up into islet-containing droplets in parallel with the computational model and empiric determinations.

The oil phase is made with polypropylene glycol (PPG) 4000 (Sigma) with 10% Span® 80 (Sigma), with or without 0.02 or 0.2% triethanolamine (TEA) to control the polymerization rate. TEA is added to the oil bath downstream outflows (FIG. 12A: 5)

The water phase is made with 5% w/v PEG-dVS or PEG-MAL (PEG-dVS-FITC added in a 1:10 ratio with PEG-dVS or 3000 kDa FITC dextran at 1 mg/ml when fluorescence labeling of PEG gel is required), 3.1 mg/ml DTT (4 mole of DTT for 1 mole of PEG-dVS), 0.8% MVG (Novamatrix) and 75,000 islet-like beads (polystyrene red beads) or cell clusters per ml in buffer (HBSS without $Ca^{2+}$ and $Mg^{2+}$). The pH of the PEG solution has been adjusted to be lower than 6 (5 for Peg-dVS and 3.5 for PEG-MAL).

The water phase is injected through a needle into the oil phase first at 50 µl/min and then reduced to 10 µl/min. The oil phase rate is kept constant at 3.5 ml/min while the water phase is decreased to avoid oil backflow into the water phase injection needle, and is then kept constant for the entire encapsulation process. Air is injected before the water to avoid waste of polymer and bead products and to allow stabilization of the water in oil jet.

Example 5: Encapsulated Cell Cluster Purification and Characterization

We have also optimized methods for purifying coated model beads or cell clusters from the oil phase. Coated islet-like beads or cell clusters and PEG droplets are collected from the outflow of the flow chamber into a 50 ml conical tube containing the oil phase with 0.02% or 0.2% triethanolamine (TEA) until polymerization of the PEG coating is completed (between 5 and 10 minutes after the last encapsulated cluster has reached the outlet).

The oil phase is separated from the water phase first by centrifugation for 5 minutes at 1500 rpm in 50 ml conical tubes. Subsequently, complete removal of PPG is achieved through hexane extraction several times (50% hexane and 50% HBSS) by centrifuging first for 5 minutes at 1500 rpm in a 50 ml conical tube and then for 1 minute at 500 g in 1.5 ml Eppendorff tubes until the oil is completely eliminated from the water phase and the HBSS results are clear from PPG (a whitish emulsion formed by the two phases easily reveals PPG presence in HBSS). 50 mM $CaCl_2$) solution in osmotically balanced buffer is added to allow gelation of MVG.

PEG droplets can be separated from PEG-coated beads or clusters by gradient centrifugation (PEG gel has a lower density than islets) by layering Ficoll solutions at the following densities: 1.042 g/ml and media. After centrifugation, coated beads or clusters will be at the bottom while empty beads will layer on top of the 1.042 g/ml layer and in the media. The supernatant is discarded and coated beads or clusters are collected and washed. PEG coating of beads or clusters can be imaged by fluorescence microscopy or by confocal microscopy if PEG-dVS-FITC or 3000 kDa FITC dextran is added to the water phase.

By optimizing the experimental set-up, we improved the efficiency of bead and cell cluster coating by PEG from 10 to 95%, achieving a good yield of coated versus non-coated beads or clusters. Coated beads have a uniform PEG coat around their volume of between about 10 and 20 µm, and the thickness of this coating does not depend on bead size (which varies between 50 and 300 µm).

Confocal imaging and image processing by Imaris allows for evaluation of the quality of the coating, with some limitations concerning confocal laser penetration through the samples (we cannot image both sides of the coating). FIG. 15A-D depicts some examples of confocal imaging of FITC-PEG coated beads; left: orthogonal projection of a z-scan of the entire coated bead, right: 3D reconstruction of the z-scan series and sectioned in the mid plane.

Example 6: Optimization of Encapsulation for Coating Thickness and Completeness Using Heterogeneous Bead Models The characteristics of the conformal coating that we aimed to achieve are as follows: (1) high efficiency of coating (high ratio of coated vs. uncoated beads), (2) high efficiency of primary vs. secondary polymer products (reduce the number of empty polymer beads and the size of secondary products from jet break-up), and (3) high yield of coated beads after purification from the oil phase.

We performed several experiments in which the effect of the following parameters as an outcome indicator were evaluated:
(a) bead concentration in the water phase (from 5,000 to 100,000 IEQ/ml),
(b) surfactant concentration in the water phase (to prevent bead coalescence after coating, 0 to 2.5% Pluronic® F-68 (polyoxyethylene-polyoxypropylene block copolymer)),
(c) ratio of the flow rates of the water phase (Qw) with respect to the oil phase (Qo) and absolute flow rate of the oil phase (the following Qw/Qo combinations have been tested: 50 µl/min-0.5 ml/min; 50 µl/min-2.5 ml/min; 150 µl/min-0.5 ml/min, 150 µl/min-2.5 ml/min,
(d) design of the flow chamber (both the focusing angle of the device that allows dripping to jet transition of the water phase in oil and the diameter of the down-stream channel (diameter: d) have been modified, resulting in four different device designs: more focusing/d=1 mm; less focusing/d=1 mm; more focusing/d=3 mm; less focusing/d=3 mm),
(e) position of the water phase injection needle with respect to the focusing channel of the device (this affects the dripping to jetting transition) (from 0 mm to 1 mm upstream of the focusing region),
(f) composition and setup of the outflow collection media (100% oil phase and 0% water phase and different % triethanolamine in oil, and magnetic stirring vs. non stirring of the collected outflow),
(g) coated bead extraction from the oil phase and separation from the secondary polymeric beads and the oil phase (addition of different volumes of hexane solvent for oil phase removal and different cycles of centrifugation and coated bead sedimentation periods).

FIG. 16A-16F shows examples of coated bead morphology resulting from the different combinations of the above experimental parameters. In these examples, FITC-PEG-dVS has been added to the water phase at 1% concentration to fluorescently label the coating and to enable evaluation of the coating efficiency.

One optimized protocol for bead coating that resulted from the above optimization experiments is as follows:
Composition of the water phase: 10% PEG-dVS, 2% Pluronic® F-68 (polyoxyethylene-polyoxypropylene block copolymer), 50000 IEQ/ml and 0.62% w/v of DTT in serum-free media pH 6.5;
Flow parameters: Qw=50 µl/min/Qo=0.5 ml/min (Qo/Qw=350 & Vo/Vw=3.5);
Device design: more focusing device, d=1 mm, focusing angle of 60 degrees, injection needle 0.5 mm upstream of focusing region;
Outflow: 5 ml PPG with 0.02% triethanolamine stirred at 300 rpm/outflow tube into the oil phase and far from the stirring cone; and
Purification: collect outflow in a 15 ml conical tube. Centrifuge 1500 rpm/5 min. Discard all PPG. Resuspend the coated beads and secondary polymer beads in 1 ml hexane and transfer to a 2 ml eppendorff tube. Centrifuge 1 min/500 g. Discard hexane supernatant. Add 0.5 ml hexane and resuspend, then add 1 ml PBS. Centrifuge 1 min/500 g. Discard hexane/PBS supernatant. Resuspend in 1 ml PBS. Proceed with gradient centrifugation (described above) to purify coated beads from secondary empty PEG beads.

Example 7: Optimization of Composition of Coating Material for Desired Permeability and Permselectivity Depending on the application of the encapsulation technology described here, different values of permeability and permselectivity may be needed. We validated existing experimental methods to assess those parameters in several alginate and PEG-based hydrogels. We found a negative correlation between the degree of cross-linking and the network tightness of PEG-dVS-based hydrogels and their permeability to proteins of known molecular weight (FIG. 17A). In order to decrease the degree of cross-linking of PEG-dVS 8-arm 10 kDa through DTT, we capped VS functional groups through exposure to beta-mercaptoethanol at different molar ratios to the functional groups (cap 0: de-functionalize 0 out of 8 VS groups on the PEG; cap 2: de-functionalize 2 out of 8 VS groups on the PEG; cap 4: de-functionalize 4 out of 8 VS groups on the PEG). In order to decrease the tightness of hydrogel networks, we included alginate (MVG from Novamatrix) as a network 'spacer' and replaced DTT with a longer crosslinker (PEGdiThiol 1 kDa) or used PEG-dVS 4-arms 20 kDa as a monomer instead of PEG-dVS 8-arm 10 kDa. 10 kDa FITC dextran was added at 1 mg/ml to hydrogel beads and the amount (as concentration: c) that diffused out over time was measured by fluorescence reading of the outer bath in which beads resided. The ratio between c and the calculated equilibrium concentration ($c_{inf}$) is plotted against time and represents the kinetic of diffusion out of 10 kDa dextran of each hydrogel composition as compared to 1.6% MVG. For each hydrogel composition, permselectivity can be measured by adding proteins of different molecular weight to the hydrogel beads and measuring the concentration of each protein in the outer batch at different time points. The percentage of proteins that have diffused out at higher time points for each protein represents the capability of each protein to selectively move through the hydrogel network. For PEG-dVS 8-arm 10 kDa and 0.8% MVG cross-linked with DTT, permselectivity can be assumed to be between 250 and 500 kDa (FIG. 17B).

Figure 18:
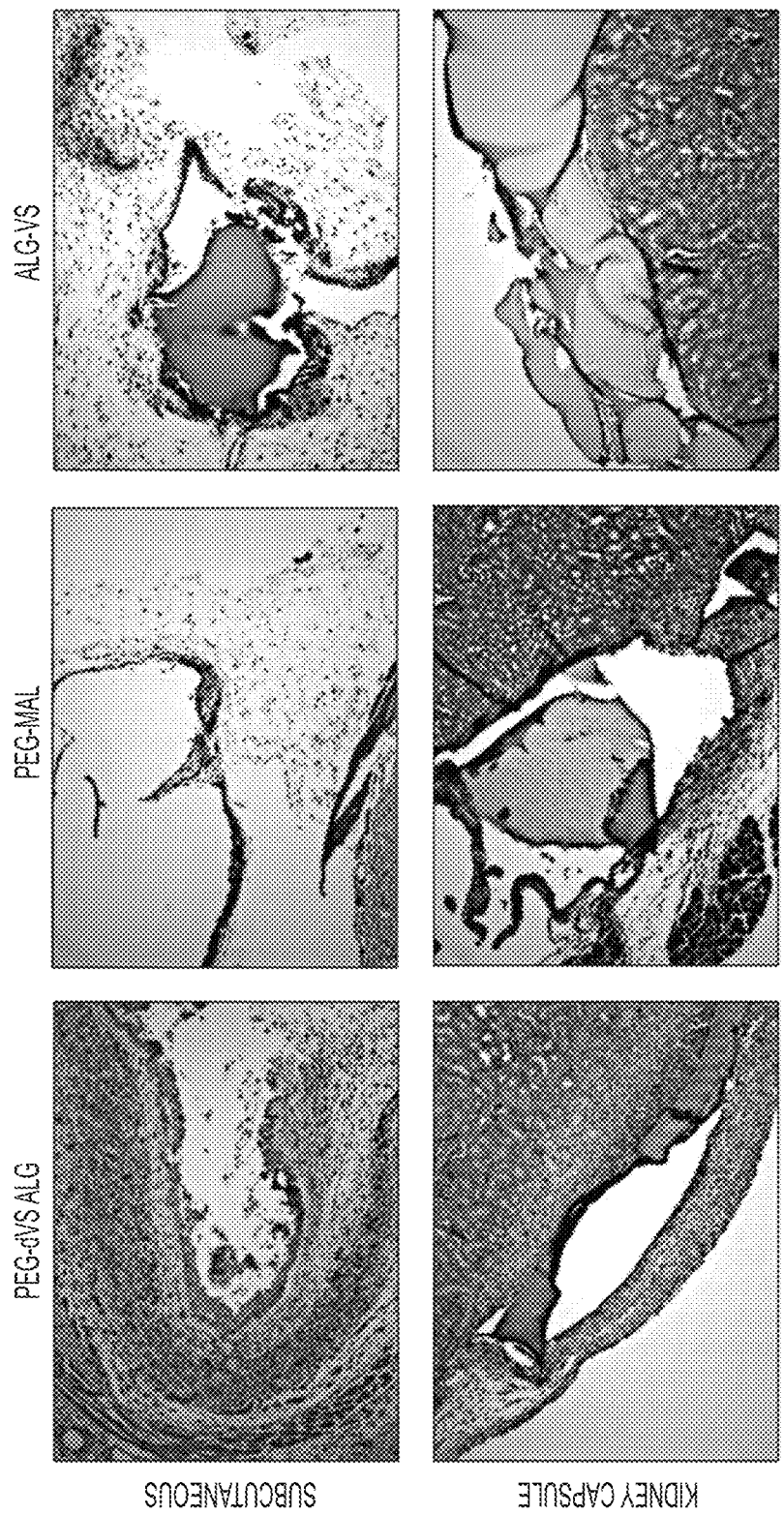
FIG. 18: Biocompatibility of different ALGINATE and PEG-based hydrogels in the subcutaneous site and under the kidney capsule at day 7.

Example 8: Optimization of Composition of Coating Material for Biocompatibility in the Desired Implant Site Depending on the application of the encapsulation technology described here, different sites of implantation are desirable. Biocompatibility for a certain hydrogel being dependent on implant site, we have established and validated a method to evaluate the biocompatibility of different hydrogel compositions in mice. We generated hydrogel macroparticles (between 0.5 and 2 mm in size) and implanted them in sterile condition within HBSS in different sites in mice and rats: subcutaneous, under the kidney capsule, epidydimal fat, intraperitoneal, in an omental pouch). Histological examination of cellular infiltrates and tissue remodeling at the biomaterial-tissue interface was evaluated and scored to compare the biocompatibility of different materials. We have found that bioreactivity of PEG-dVS is greater than PEG-MAL and ALG-VS, independent of the implant site (FIG. 18), and that the subcutaneous and the kidney subcapsular sites are more reactive sites to biomaterial implantation.

Example 9: Optimization of Encapsulation for Coating Completeness Using Rat Islets The characteristics of the conformal coating that we aimed to achieve are as follows: (1) high efficiency of coating (high ratio of coated vs. uncoated islets), (2) high efficiency of primary vs. secondary polymer products (reduce the number of empty polymer beads and the size of secondary products from jet break-up), and (3) high yield of coated islets after purification from the oil phase.

We performed several experiments in which the effect of the following parameters as outcome indicators were evaluated:

(a) islet concentration in the water phase (from 5,000 to 100,000 IEQ/ml),
(b) surfactant and alginate concentration in the water phase (to prevent islet coalescence after coating, 0 to 2.5% Pluronic® F-68 (polyoxyethylene-polyoxypropylene block copolymer) and 0 to 1.6% MVG from Novamatrix),
(c) ratio of the flow rates of the water phase (Qw) with respect to the oil phase (Qo) and absolute flow rate of the oil phase (the following Qw/Qo combinations, for example, have been tested: 50 µl/min-0.5 ml/min; 50 µl/min-2.5 ml/min; 150 µl/min-0.5 ml/min, 150 µl/min-2.5 ml/min),
(d) design of the flow chamber (both the focusing angle of the device that allows dripping to jet transition of the water phase in oil and the diameter of the down-stream channel (diameter: d) have been modified, resulting in four different device designs: more focusing/d=1 mm; less focusing/d=1 mm; more focusing/d=3 mm; less focusing/d=3 mm),
(e) position of the water phase injection needle with respect to the focusing channel of the device (this affects the dripping to jetting transition) (from 0 mm to 1 mm upstream of the focusing region),
(f) composition and setup of the outflow collection media (100% oil phase and 0% water phase and different % triethanolamine in oil, and magnetic stirring vs. non stirring of the collected outflow),
(g) coated islet extraction from the oil phase and separation from the secondary polymeric beads and the oil phase (addition of different volumes of hexane solvent for oil phase removal and different cycles of centrifugation and coated islet sedimentation periods).

Figure 19A:
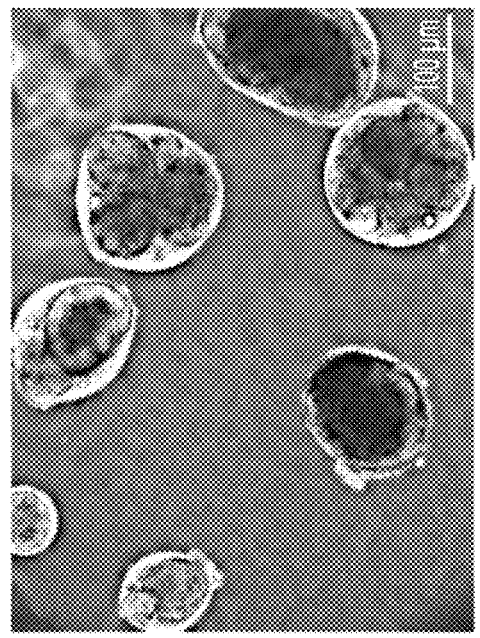
FIG. 19A, FIG. 19B, and FIG. 19C: Conformal coating of rat islets of Langerhans.
Figure 19B:
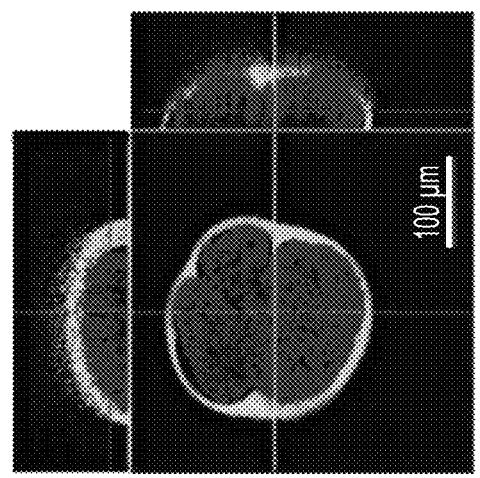
Figure 19C:
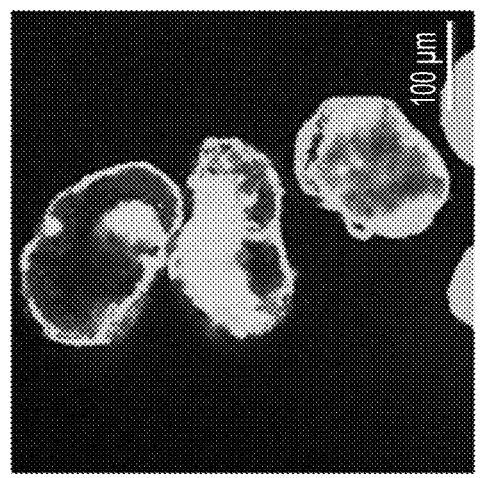

FIG. 19A-19C shows coated islet morphology resulting from the optimal combinations of the above experimental parameters. In these examples, FITC-PEG-dVS (FIG. 19B) or 2000 kDa FITC dextran (FIG. 19C) have been added to the water phase at 1% or 1 mg/ml concentration respectively to fluorescently label the coating and to enable evaluation of coating completeness and efficiency.

The optimized protocol for islet coating that resulted from the above optimization experiments is as follows:

Composition of the water phase: 5% PEG-dVS, 0.8% MVG (Novamatrix), 75000 IEQ/ml and 0.31% w/v of DTT in HBSS without $Ca^{2+}$ and $Mg^{2+}$ with the PEG solution at pH 5;

Flow parameters: Qw=10 µl/min/Qo=3.5 ml/min (Qo/Qw=350 & Vo/Vw=3.5); Device design: more focusing device, d=1 mm, focusing angle of 60 degrees, injection needle 0.5 mm upstream of focusing region;

Outflow: 15 ml PPG with 0.02% triethanolamine in a 50 ml conical tube; and Purification: Centrifuge 1500 rpm/5 min. Discard all PPG. Resuspend the coated islets and secondary polymer beads in 5 ml hexane and pipet up and down 5 times without breaking the pellet. Add 40 ml HBSS without $Ca^{2+}$ and $Mg^{2+}$ and invert the tube twice. Centrifuge 5 min/1500 rpm. Discard supernatant. Add 1 ml HBSS without $Ca^{2+}$ and $Mg^{2+}$, resuspend the pellet and transfer to a 1.5 ml Eppendorf low-binding microcentrifuge tube. Centrifuge 30 sec/500 g. Discard supernatant. Add 0.5 ml hexane and then 1 ml HBSS without $Ca^{2+}$ and $Mg^{2+}$ and invert the tube three times to mix. Centrifuge 30 sec/500 g. Discard hexane/PBS supernatant. Resuspend in 1 ml HBSS with $Ca^{2+}$ and $Mg^{2+}$. Centrifuge 30 sec/500 g. Discard supernatant and resuspended in basal islet media. Plate the coated islets at 38 $IEQ/cm^2$ in petri dishes containing full media that had been equilibrated in a 5% CO2 and 37° C. incubator for at least 15 minutes.

Figure 20A:
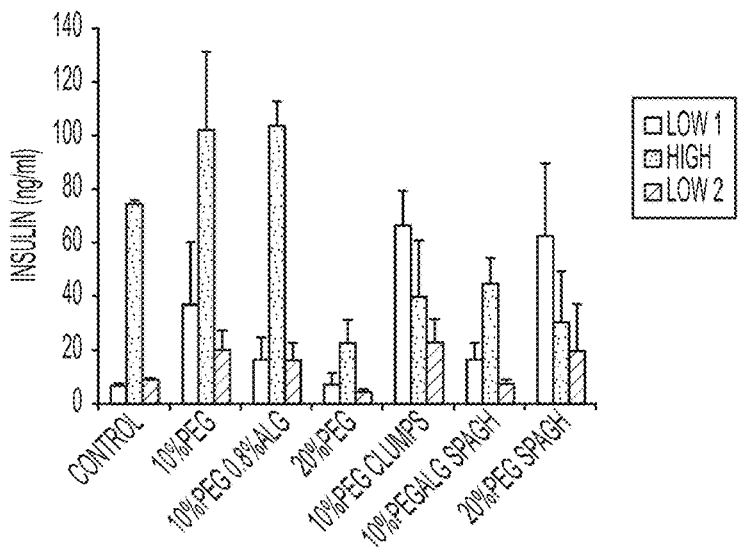
FIG. 20A, FIG. 20B, and FIG. 20C: Functional response (insulin release upon glucose stimulation) of rat islets encapsulated with different hydrogel compositions.
Figure 20B:
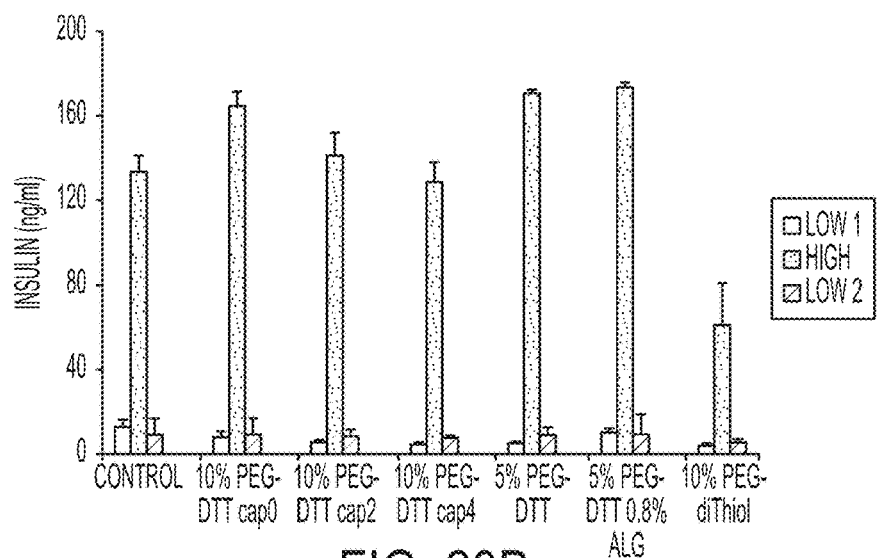
Figure 20C:
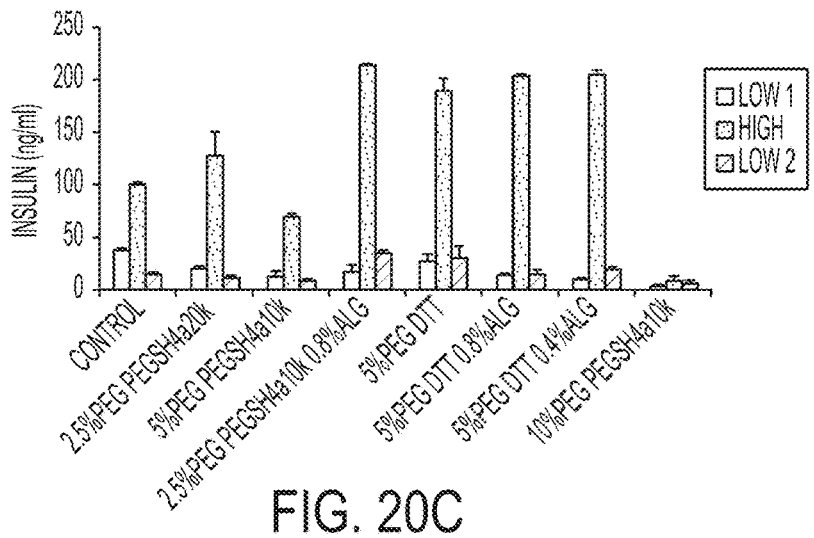

Example 10: Evaluation of In Vitro Function of Encapsulated Islets as a Function of Encapsulation Materials The functional response (insulin release upon glucose stimulation) of rat islets encapsulated with different hydrogel compositions has been evaluated through a previously established method of static stimulation with different amounts of glucose: Low1: 60 mg/dL glucose, High: 300 mg/dL, Low2: 60 mg/dL. As expected, insulin response to glucose stimulation positively correlated with increased permeability of each hydrogel coating composition (FIGS. 17A-17B and 20A-20C). Islets coated with PEG-dVS 8arm 10 kDa and cross-linked with DTT had better response at lower PEG percentages and for conformal coating versus clumps and rods (SPAGH) and when MVG alginate (ALG) was added to the hydrogel (FIG. 20A). Islets conformally coated with PEG-dVS 8arm 10 kDa cross-linked with DTT showed better response than gels crosslinked with linear HS-PEG-SH, while capping PEG-VS functional groups with beta-mercaptoethanol did not show any impressive improvement (FIG. 20B). Islets conformally coated with PEG-dVS 8arm 10 kDa cross-linked with DTT showed better response than crosslinking with multi-arm HS-PEG-SH (4-arm 10 kDa and 4-arm 20 kDa, FIG. 20C).

Example 11: Optimization of Encapsulation for Viability and In Vitro Function of Encapsulated Islets as a Function of Timing We have evaluated the effect of timing between isolation/encapsulation/functional evaluation on islet viability (live/dead staining) and functional response (insulin release upon glucose stimulation) of rat islets encapsulated with 5% PEG-dVS 8arm 10 kDa 0.8% MVG cross-linked with DTT (PEG ALG). Rat islets encapsulated by conformal coating two days after isolation are poorly viable right after encapsulation and show a ring of death on the external surface. Culture in standard conditions for up to 48 hours after encapsulation allows complete recovery of islet viability (FIG. 21A). While the functional response (insulin secretion after glucose stimulation: L1: 60 mg/dL glucose, H: 300 mg/dL, L2: 60 mg/dL) of naked islets rapidly deteriorates during standard ex vivo culture after isolation (FIG. 21B), encapsulation through conformal coating with PEG ALG one day (FIG. 21C) or two days (FIG. 21D) after isolation and evaluated at 24 and 48 hours after encapsulation, is able to completely preserve islet function.

Example 12: Evaluation of In Vivo Function of Encapsulated Islets in Restoring Normoglycemia of Chemically-Induced Diabetic Mice In vivo function of islets encapsulated through conformal coating has been for their ability to restore normoglycemia in chemically-induced diabetic immunocompetent mice following transplants of encapsulated syngeneic islets under the kidney capsule.

Figure 22:
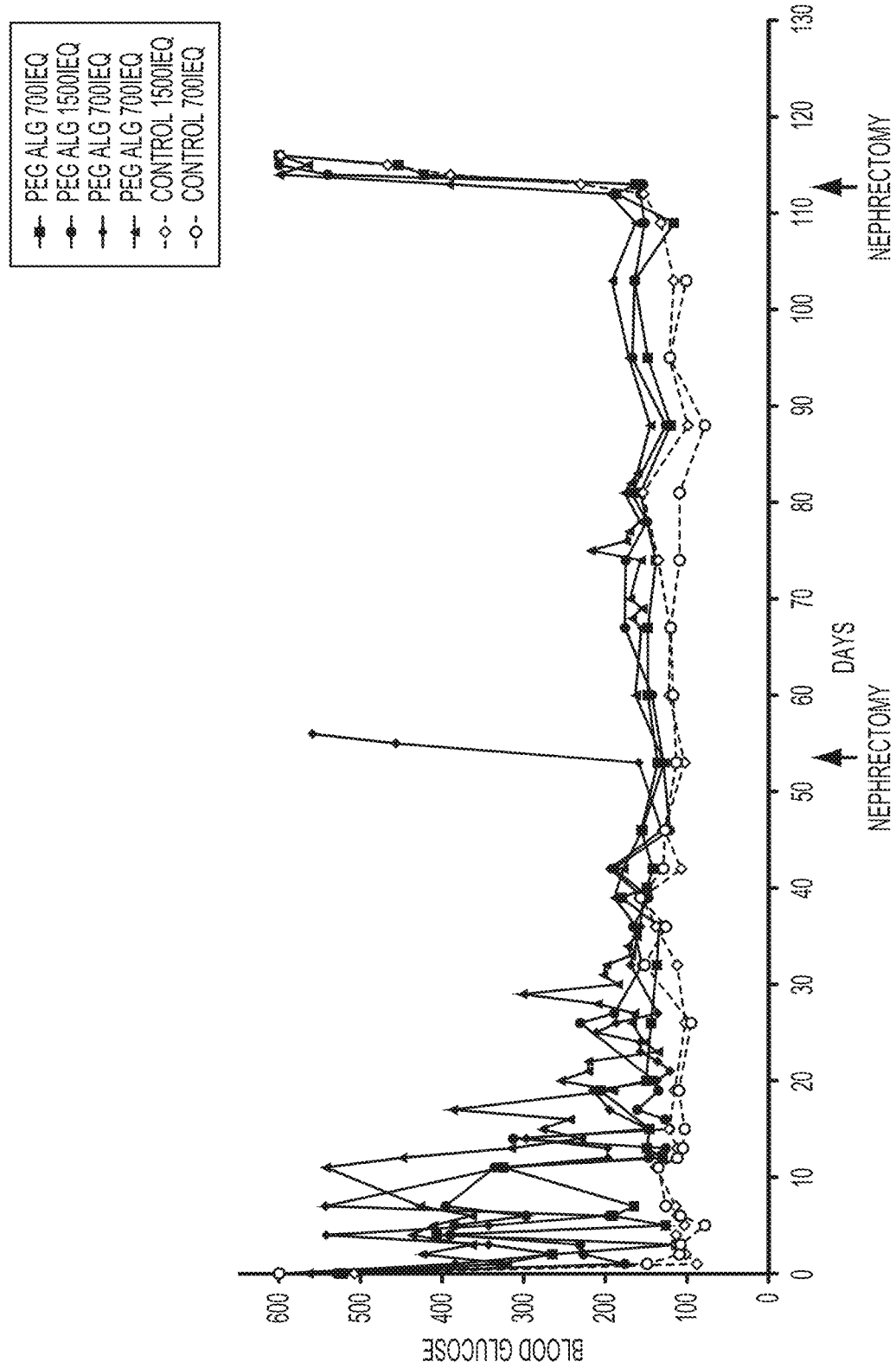
FIG. 22: In vivo function of murine (C57BL/6) islets conformally coated with PEG ALG and transplanted under the kidney capsule of chemically induced diabetic syngeneic mice, expressed as blood glucose of recipient mice over time. Nephrectomy was performed in order to confirm that normoglycemia was due to coated islets function.

Murine (C57BL/6) islets conformally coated with PEG ALG and transplanted at 700 or 1500 IEQ/mouse under the kidney capsule of chemically-induced diabetic syngeneic mice rapidly reversed diabetes in recipient mice and allowed maintenance of normoglycemia for more than 100 days. Nephrectomy confirmed that normoglycemia was due to coated islet function (FIG. 22).

Figure 23:
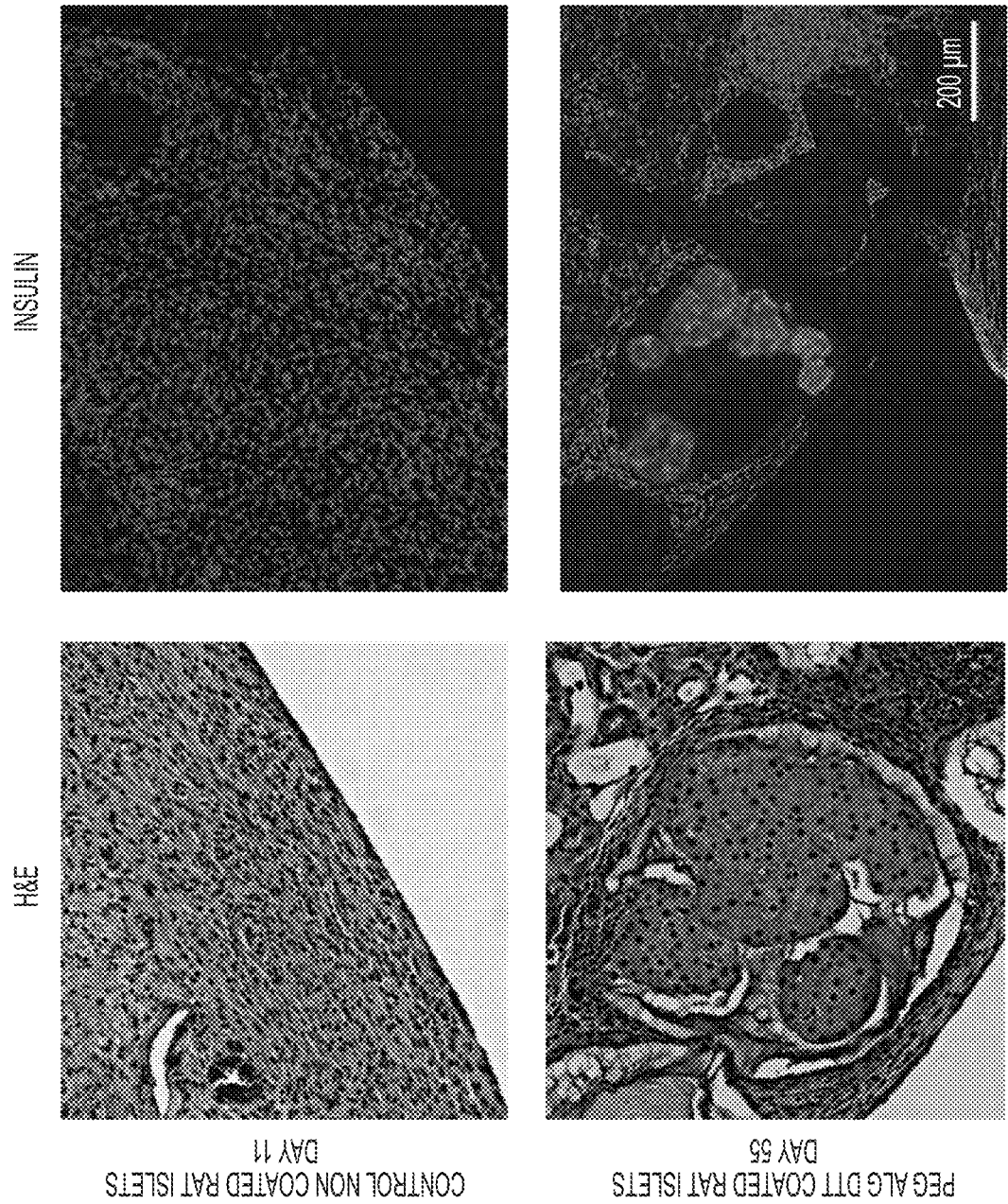
FIG. 23: Histological (H&E, left) and immunohistochemical (insulin: right) evaluation at rejection time of naked controls (top, day 11) and conformally coated (bottom, day 55) islets transplanted under the kidney capsule of concordant xenogeneic recipients.

Histological (FIG. 23, left) and immunohistochemical (FIG. 23, right) evaluation at rejection time of naked controls (top, day 11) and conformally coated (bottom, day 55) islets transplanted under the kidney capsule of concordant xenogeneic recipients confirms that conformal coating is able to protect islet xeno-transplants from immune destruction without compromising their viability and metabolic function.

Example 13: Utility of Conformal Coating in Immunoisolation of Islet Allografts

Islets are isolated and conformally coated by the methods described above, then implanted in diabetic allogeneic hosts. The viability and function of the coated islets are assessed by MTT assay, live/dead staining and by static glucose stimulation pre-implantation as described above to guarantee the potential of coated islets to normalize glycaemia in diabetic hosts. Immunoprotection of transplanted islets from rejection by conformal coating is evaluated by monitoring the blood glucose level and weight of the transplanted host and by histological evaluation after sacrifice.

Example 14: Utility of Conformal Coating in Immunoisolation of Islet Xenografts

Islets are isolated and conformally coated by the methods described above, then implanted in diabetic xenogeneic hosts. The viability and function of the coated islets are assessed by MTT assay, live/dead staining and by static glucose stimulation pre-implantation as described above to guarantee the potential of coated islets to normalize glycaemia in diabetic hosts. Immunoprotection of transplanted islets from rejection by conformal coating is evaluated by monitoring the blood glucose level and weight of the transplanted host and by histological evaluation after sacrifice.

Example 15: Scale Up of Conformal Coating Methods

In the flow chambers that we designed, the oil phase is made with polypropylene glycol (PPG) 4000 (Sigma) with 10% Span® 80 (Sigma). The water phase is made with hydrogel solution. The water phase is injected through a needle into the oil phase at 10 μl/min. The oil phase rate is maintained at 3.5 ml/min.

Because the coating device is in a vertical configuration, the procedure can be scaled up to guarantee conformal coating of larger human preparations with no variability between batches of the same preparation. To allow encapsulation of hundreds of thousands of human islets at the same time and with the same experimental parameters, a series of parallel vertical chambers can be assembled in a radial configuration in which radial flow to each chamber feeds the water phase containing the islet prep to each separate chamber with comparable hydrodynamic flow characteristics. In this manner, water jet break-up happens at the same time in each separate chamber, resulting in comparable coatings for islets coming from different channels. Coated islets and secondary empty polymer beads are then collected in the same container and purified at the same time to further reduce any potential batch to batch variability.

All publications and patent applications cited in this specification are incorporated herein by reference as if each individual publication or patent application were specifically and individually indicated to be incorporated by reference.

REFERENCES

[1] Robertson, R. P. Update on transplanting beta cells for reversing type 1 diabetes. *Endocrinol Metab Clin North Am* 39, 655-667, doi:S0889-8529(10)00042-3 [pii] 10.1016/j.ecl.2010.05.010 [doi].

[2] de Vos, P., Spasojevic, M. & Faas, M. M. Treatment of diabetes with encapsulated islets. *Adv Exp Med Biol* 670, 38-53.

[3] Teramura, Y. & Iwata, H. Bioartificialpancreas microencapsulation and conformal coating of islet of Langerhans. *Adv Drug Deliv Rev* 62, 827-840, doi:S0169-409X(10) 00036-0 [pii] 10.1016/j.addr.2010.01.005 [doi].

[4] de Groot, M., Schuurs, T. A. & van Schilfgaarde, R. Causes of limited survival of microencapsulated pancreatic islet grafts. *J Surg Res* 121, 141-150, doi:10.1016/j.jss.2004.02.018 [doi] S0022480404000629 [pii] (2004).

[5] Rabanel, J. M., Banquy, X., Zouaoui, H., Mokhtar, M. & Hildgen, P. Progress technology in microencapsulation methods for cell therapy. *Biotechnol Prog* 25, 946-963, doi:10.1002/btpr.226 [doi] (2009).

[6] Eggleton, C. D., Tsai, T. M. & Stebe, K. J. Tip streaming from a drop in the presence of surfactants. *Phys Rev Lett* 87, 048302 (2001).

[7] Utada, A. S., Fernandez-Nieves, A., Gordillo, J. M. & Weitz, D. A. Absolute instability of a liquid jet in a coflowing stream. *Phys Rev Lett* 100, 014502 (2008).

[8] Loscertales, I. G. et al. Micro/nano encapsulation via electrified coaxial liquid jets. *Science* 295, 1695-1698, doi:10.1126/science.1067595 [doi] 295/5560/1695 [pii] (2002).

[9] Cohen, I., Li, H., Hougland, J. L., Mrksich, M. & Nagel, S. R. Using selective withdrawal to coat microparticles. *Science* 292, 265-267, doi:10.1126/science.1059175 [doi] 292/5515/265 [pii] (2001).

[10] Chabert, M. & Viovy, J. L. Microfluidic high-throughput encapsulation and hydrodynamic self-sorting of single cells. *Proc Natl Acad Sci USA* 105, 3191-3196, doi: 0708321105 [pii] 10.1073/pnas.0708321105 [doi] (2008).

[11] Wyman, J. L. et al. Immunoisolating pancreatic islets by encapsulation with selective withdrawal. *Small* 3, 683-690, doi:10.1002/smll.200600231 [doi] (2007).

What is claimed is:

1. A method of conformally coating a biomaterial with a coating material, comprising the steps of:
   a) injecting a water phase comprising the biomaterial and the coating material within a coaxial oil phase in a coating device that allows for a transition from dripping to jetting and flow elongation of the water phase within the oil phase;
   wherein polymerization of the coating material occurs downstream of breakup of the water phase jet into particles, resulting in the conformal coating of the biomaterial with the coating material, and wherein the thickness of the conformal coating is not dependent on the size or diameter of the coated biomaterial;
   b) purifying the conformally coated biomaterial and biomaterial-free coating material from the oil phase; and
   c) separating the conformally coated biomaterial from the biomaterial-free coating material;
   wherein the biomaterial comprises cells or cell clusters, and wherein the cells or cell clusters are greater than 40 µm and up to 1000 µm in diameter.

2. The method of claim 1, wherein the biomaterial comprises pancreatic islet cells or cell clusters.

3. The method of claim 1, wherein the coating material comprises polyethylene glycol (PEG).

4. The method of claim 1, wherein:
   a) the water phase comprises 75,000 islet cells/ml, and further comprises:
      i) 10% polyethylene glycol (PEG), 2% polyoxyethylene-polyoxypropylene block copolymer, and 0.62% w/v dithiothreitol (DTT) in serum-free media at pH 6-7;
      ii) 5% PEG, 1% polyoxyethylene-polyoxypropylene block copolymer, and 0.31% w/v DTT in Hank's Balanced Salt Solution (HBSS) at pH 6-7;
      iii) 5% PEG, 1% polyoxyethylene-polyoxypropylene block copolymer, 0.8% medium viscosity G-groups alginate (MVG) and 0.31% w/v DTT in HBSS without $Ca^{2+}$ and $Mg^{2+}$ at pH 6-7; or
      iv) 5% PEG, 0.8% medium viscosity G-groups alginate and 0.31% w/v DTT in HBSS without $Ca^{2+}$ and $Mg^{2+}$ at pH 6-7; and
   b) the oil phase comprises polypropylene glycol (PPG) with 10% sorbitan oleate, wherein said oil phase further optionally comprises 0.02% or 0.2% triethanolamine.

5. The method of claim 1, wherein the coating device comprises a flow chamber comprising a flow focusing region and a channel downstream of the flow focusing region; and wherein the flow chamber has at least one of the following properties:
   a) the diameter of the inner channel of the flow focusing region is restricted from 10d to d along its length, wherein d is about 1 mm;
   b) the focusing angle of the flow focusing region is about 60 degrees;
   c) the channel downstream of the flow focusing region is 1 mm in diameter; and
   d) the water phase is injected into the flow chamber through a needle or a catheter whose tip is localized about 0.5 mm upstream of the focusing region.

6. The method of claim 1, wherein the method has at least one of the following properties:
   a) the ratio of the oil phase velocity to the water phase velocity is 350;
   b) the ratio of the oil phase viscosity to the water phase viscosity is 3.5, 130, or 13;
   c) the water phase is injected into the oil phase first at 50 µl/min and then reduced to 10 µl/min, while the oil phase is maintained at 3.5 ml/min; and
   d) air is injected into the oil phase before injection of the water phase.

7. The method of claim 1, wherein the step of purifying the conformally coated biomaterial and biomaterial-free coating material from the oil phase comprises the steps of:
   a) centrifuging the coating device outflow to separate the oil phase from the conformally coated biomaterial and biomaterial-free coating material; and
   b) optionally performing hexane extraction until the oil phase is completely eliminated from the conformally coated biomaterial and biomaterial-free coating material.

8. The method of claim 1, wherein the step of separating the conformally coated biomaterial from the biomaterial-free coating material is performed by gradient centrifugation or by settlement of the conformally coated biomaterial by gravity.

9. The method of claim 1, wherein:
a) said water phase comprises 5% polyethylene glycol (PEG), 0.8% medium viscosity G-groups alginate, 75,000 islet cells/ml, and 0.31% w/v dithiothreitol (DTT) in Hank's Balanced Salt Solution (HBSS) without $Ca^{2+}$ and $Mg^{2+}$ at pH 6-7;
b) said oil phase comprises polypropylene glycol (PPG) with 10% sorbitan oleate, wherein said oil phase optionally comprises 0.02% or 0.2% triethanolamine; and
c) said coating device comprises a flow chamber comprising a flow focusing region with a channel whose inner diameter is reduced from 10 mm to 1 mm with a focusing angle of 60 degrees, and a channel downstream of the flow focusing region that is about 1 mm in diameter.

10. The method of claim 9, wherein:
a) said method comprises the steps of:
  i) applying the oil phase to the flow chamber;
  ii) optionally injecting air into the flow chamber through a catheter whose tip is localized 0.5 mm upstream of the base of the focusing region; and
  iii) injecting the air, if present, and the water phase into the flow chamber through said catheter, wherein the water phase is first injected at 50 µl/min and then reduced to 10 µl/min, while the oil phase is maintained at 3.5 ml/min, such that the surface tension between the water and the oil phase causes the water jet to break up into microliter droplets comprising the conformally coated biomaterial and biomaterial-free coating material; and
b) said method optionally further comprises the steps of:
  iv) collecting the outflow from the flow chamber;
  v) centrifuging the outflow to separate the conformally coated biomaterial and biomaterial-free coating material from the oil phase;
  vi) removing the oil phase supernatant from the conformally coated biomaterial and biomaterial-free coating material;
  vii) resuspending the conformally coated biomaterial and biomaterial-free coating material in a composition comprising hexane;
  viii) centrifuging the mixture of step vii) to separate the conformally coated biomaterial and biomaterial-free coating material from the hexane;
  ix) removing the hexane supernatant;
  x) resuspending the conformally coated biomaterial and biomaterial-free coating material in a composition comprising hexane and a buffer which does not contain $Ca^{2+}$ and $Mg^{2+}$;
  xi) centrifuging the mixture of step x) to separate the conformally coated biomaterial and biomaterial-free coating material from the hexane and buffer which does not contain $Ca^{2+}$ and $Mg^{2+}$;
  xii) removing the hexane/buffer supernatant; and
  xiii) resuspending the conformally coated biomaterial and biomaterial-free coating material in buffer containing $Ca^{2+}$ and $Mg^{2+}$; and
c) said method optionally further comprises the steps of:
  xiv) layering solutions to form a density gradient capable of separating the conformally coated biomaterial and the biomaterial-free coating material;
  xv) applying the conformally coated biomaterial and biomaterial-free coating material to the density gradient;
  xvi) centrifuging the density gradient to separate the conformally coated biomaterial from the biomaterial-free coating material; and
  xvii) removing the supernatant containing the biomaterial-free coating material.

11. The method of claim 1, wherein the method has at least one of the following properties:
a) greater than 95% of the conformally coated biomaterial is purified from the biomaterial-free coating material;
b) the conformal coating around the biomaterial ranges from 10-20 µm in thickness; and
c) greater than 90% of the biomaterial introduced into the coating device is conformally coated.

* * * * *